(12) United States Patent
Tzahor et al.

(10) Patent No.: US 10,017,574 B2
(45) Date of Patent: Jul. 10, 2018

(54) METHODS, KITS AND DEVICES FOR PROMOTING CARDIAC REGENERATION

(71) Applicants: Yeda Research and Development Co. Ltd., Rehovot (IL); Victor Chang Cardiac Research Institute, Darlinghurst (AU)

(72) Inventors: Eldad Tzahor, Rehovot (IL); Gabriele Matteo D'Uva, Rehovot (IL); Rachel Sarig, Rehovot (IL); Alla Aharonov, Rehovot (IL); Richard Paul Harvey, Darlinghurst (AU); Kfir Baruch Umansky, Rehovot (IL)

(73) Assignees: Yeda Research and Development Co. Ltd., Rehovot (IL); Victor Chang Cardiac Research Institute, Darlinghurst (AU)

( * ) Notice: Subject to any disclaimer, the term of this patent is extended or adjusted under 35 U.S.C. 154(b) by 0 days.

(21) Appl. No.: 15/147,178

(22) Filed: May 5, 2016

(65) Prior Publication Data
US 2016/0326250 A1 Nov. 10, 2016

Related U.S. Application Data

(60) Provisional application No. 62/158,111, filed on May 7, 2015.

(51) Int. Cl.
| | |
|---|---|
| A61K 38/18 | (2006.01) |
| A61K 31/7115 | (2006.01) |
| C07K 16/28 | (2006.01) |
| A61K 39/395 | (2006.01) |
| G01N 33/50 | (2006.01) |
| A61K 38/17 | (2006.01) |
| A61K 9/00 | (2006.01) |

(52) U.S. Cl.
CPC ............ *C07K 16/2863* (2013.01); *A61K 9/00* (2013.01); *A61K 38/1709* (2013.01); *A61K 38/1825* (2013.01); *A61K 38/1883* (2013.01); *A61K 39/3955* (2013.01); *G01N 33/5023* (2013.01); *G01N 33/5061* (2013.01); *A61K 31/7115* (2013.01); *C07K 2317/75* (2013.01)

(58) Field of Classification Search
CPC ............ A61K 31/7115; A61K 38/1883; A61K 39/3955; C07K 16/2863; C07K 2317/75
See application file for complete search history.

(56) References Cited

U.S. PATENT DOCUMENTS

| | | | | |
|---|---|---|---|---|
| 7,795,212 | B2 * | 9/2010 | Zhou ...................... | A61K 45/06 514/16.4 |
| 8,936,806 | B2 * | 1/2015 | Kuhn ................... | C12N 5/0657 424/423 |
| 2006/0281791 | A1 * | 12/2006 | Keating ................. | A61K 31/17 514/355 |
| 2013/0017200 | A1 * | 1/2013 | Scheer ................. | C07K 16/283 424/136.1 |
| 2013/0040879 | A1 | 2/2013 | Marchionni et al. | |
| 2013/0287728 | A1 | 10/2013 | Pecora et al. | |
| 2014/0031284 | A1 | 1/2014 | Zhou | |
| 2014/0227247 | A2 | 8/2014 | Ford | |
| 2015/0065418 | A1 | 3/2015 | Zhou | |

OTHER PUBLICATIONS

D'Uva et al. "ERBB2 Triggers Mammalian Heart Regeneration by Promoting Cardiomyocyte Dedifferentiation and Proliferation", Nature Cell Biology, 17(5): 627-638, Published Online Apr. 6, 2015.

\* cited by examiner

*Primary Examiner* — Daniel C Gamett

(57) ABSTRACT

A method of potentiating cardiac regeneration with neuregulin treatment in a subject in need thereof. The method comprising administering to the subject a therapeutic effective amount of an agent which upregulates activity or expression of ErbB-2, thereby potentiating cardiac regeneration with neuregulin treatment.

10 Claims, 13 Drawing Sheets
(13 of 13 Drawing Sheet(s) Filed in Color)

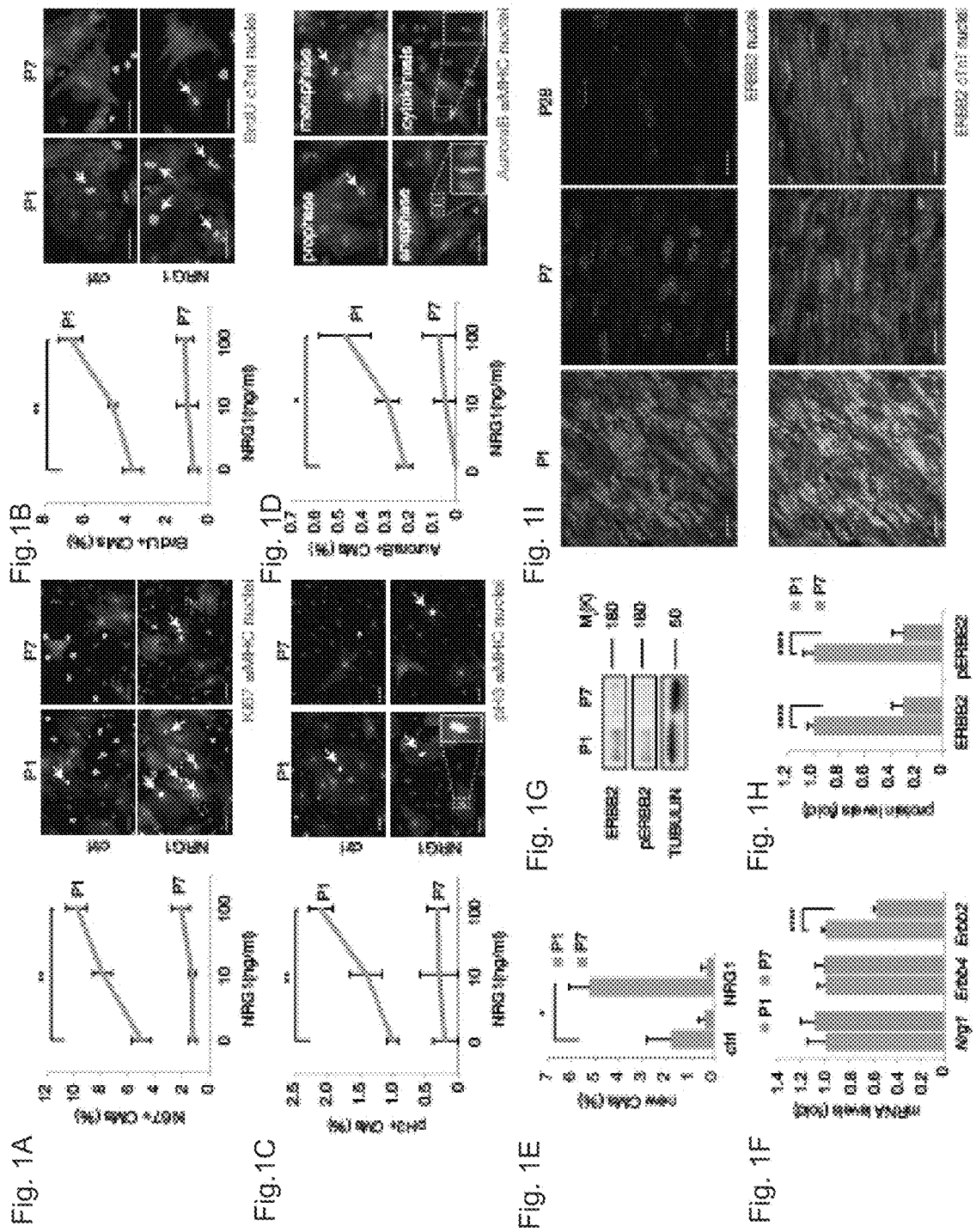

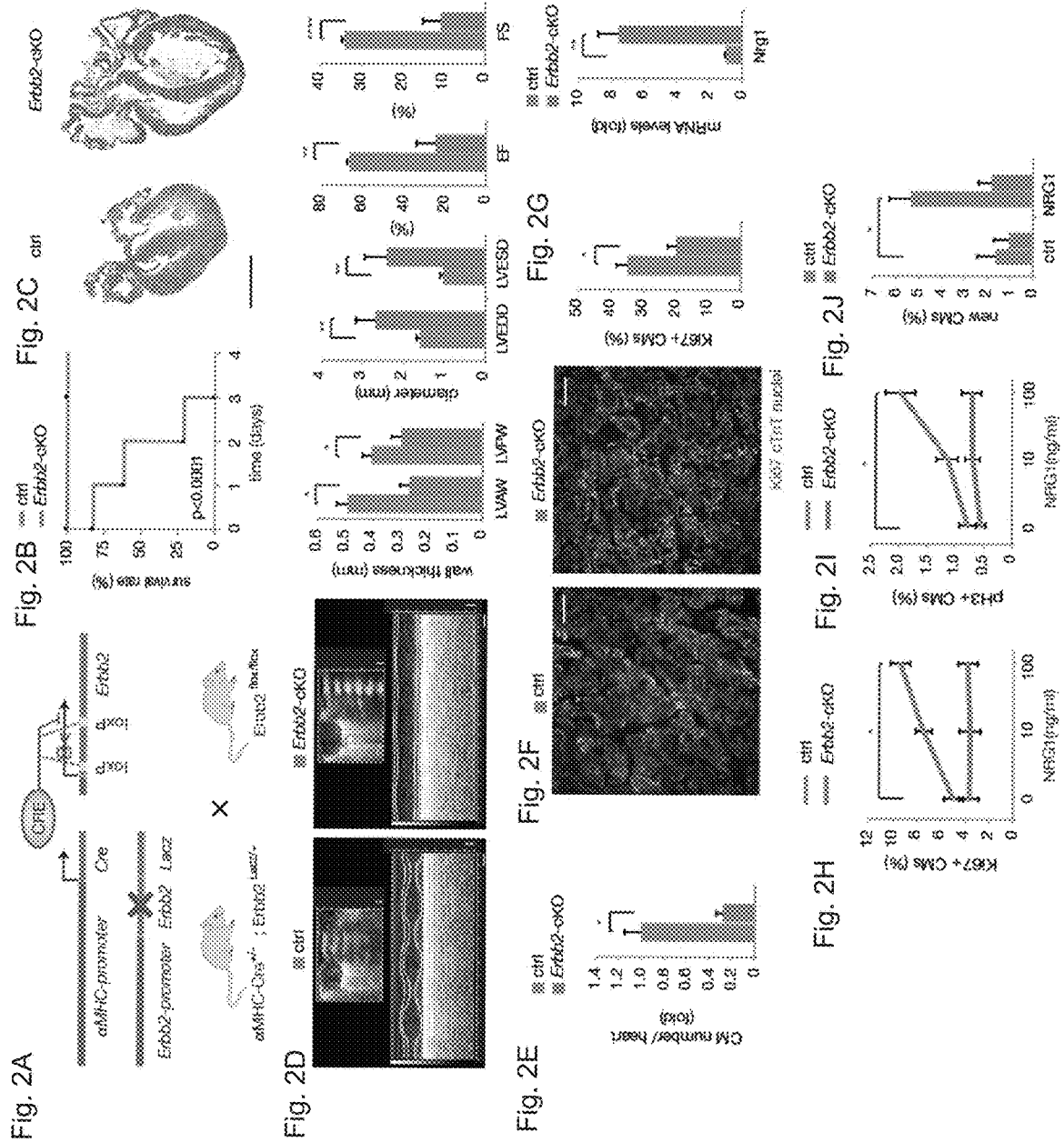

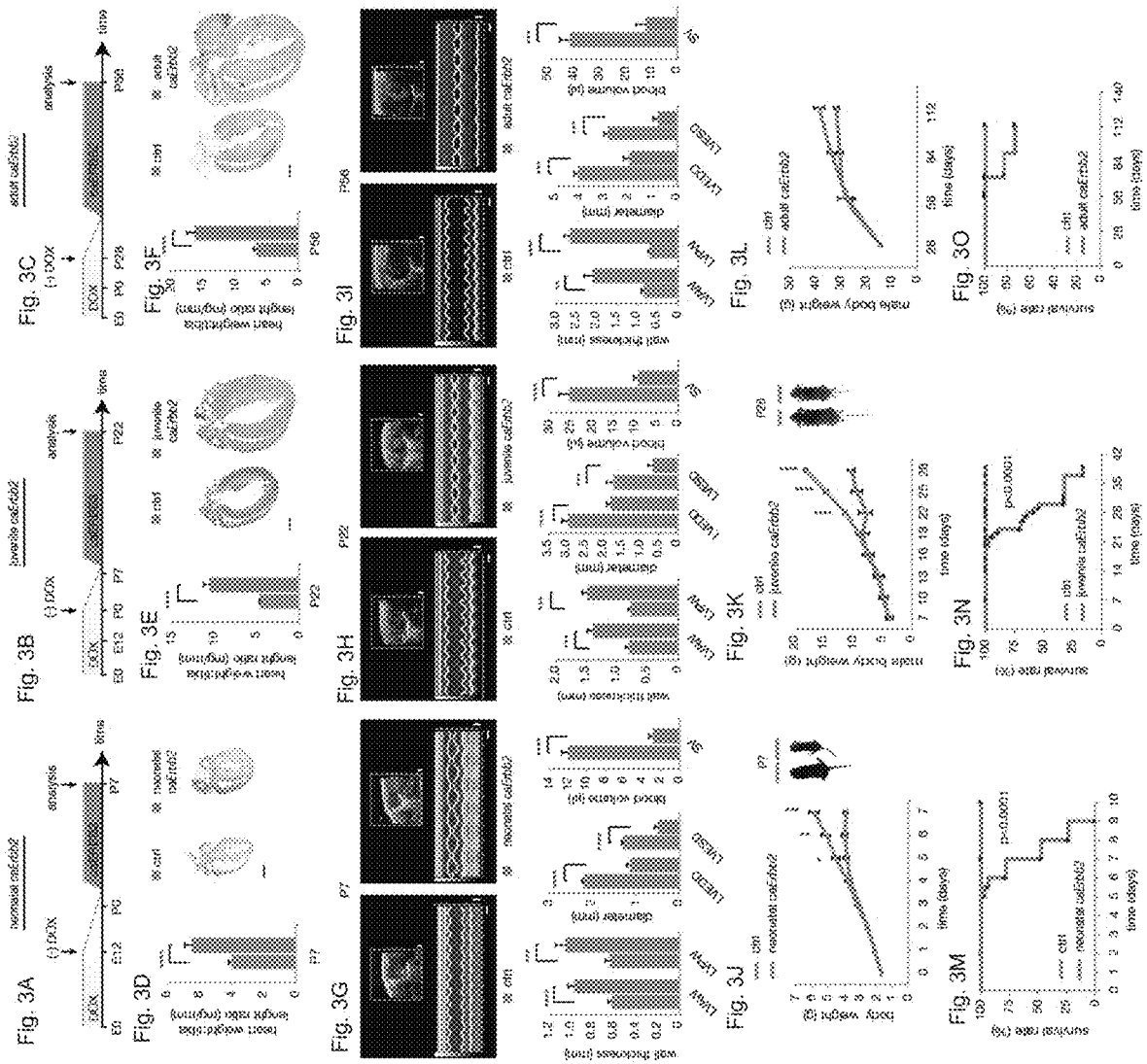

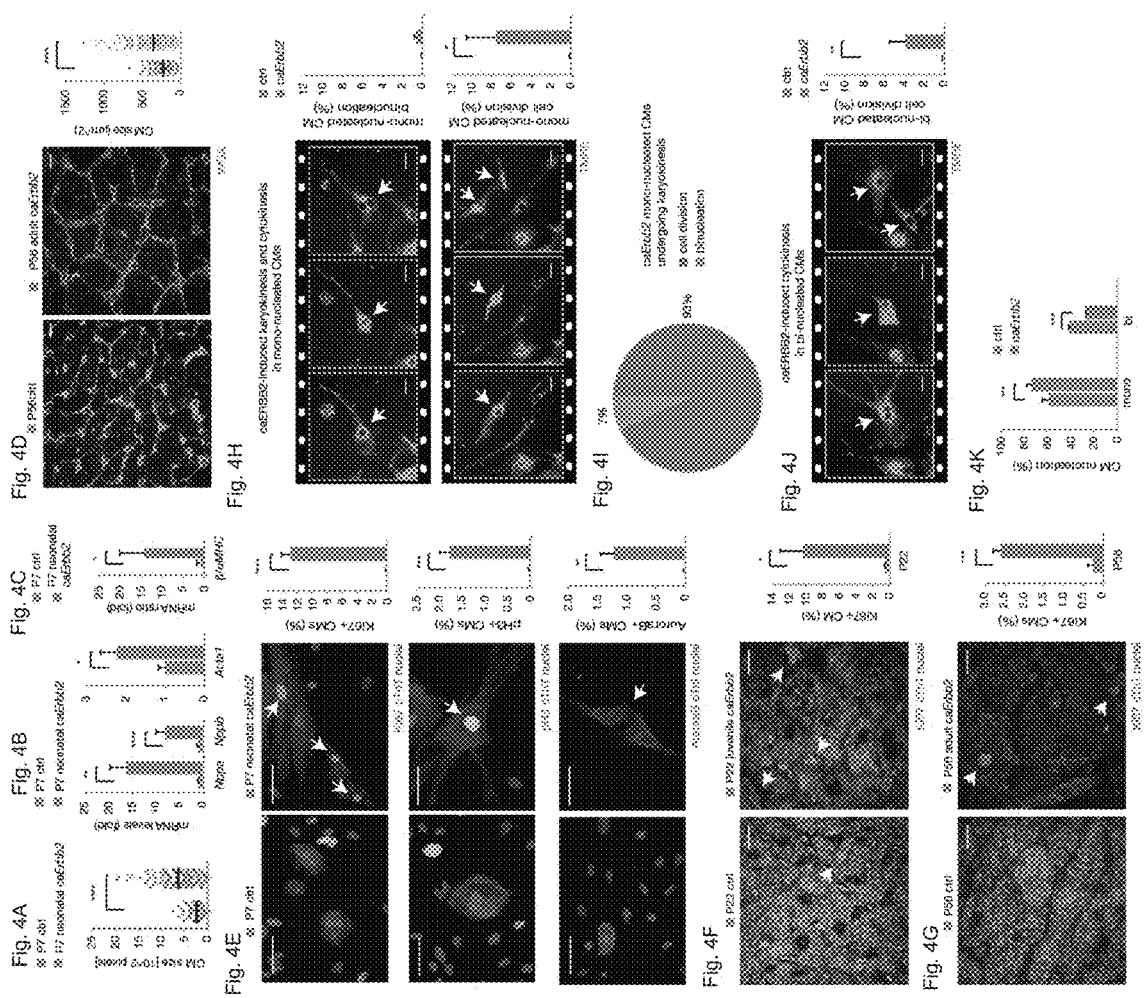

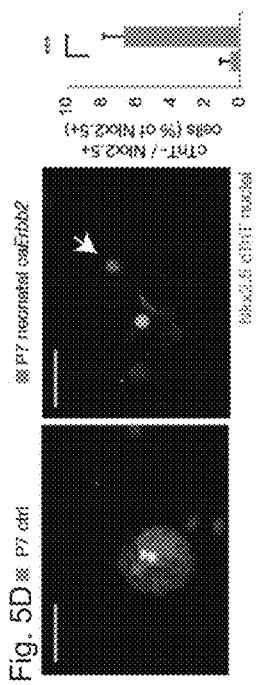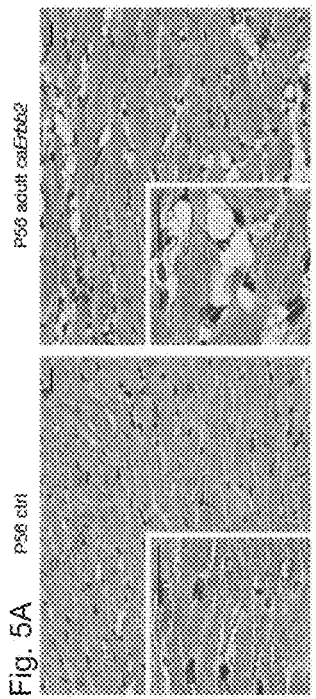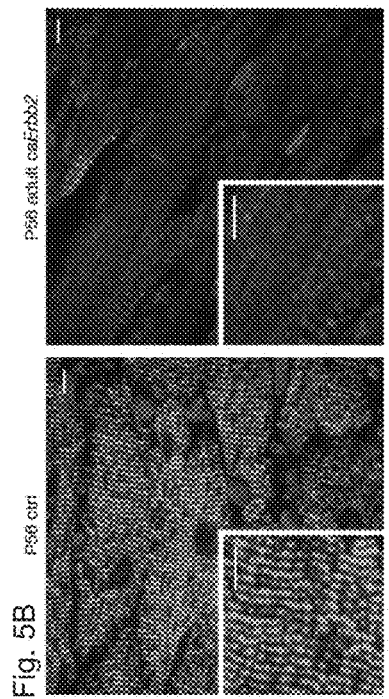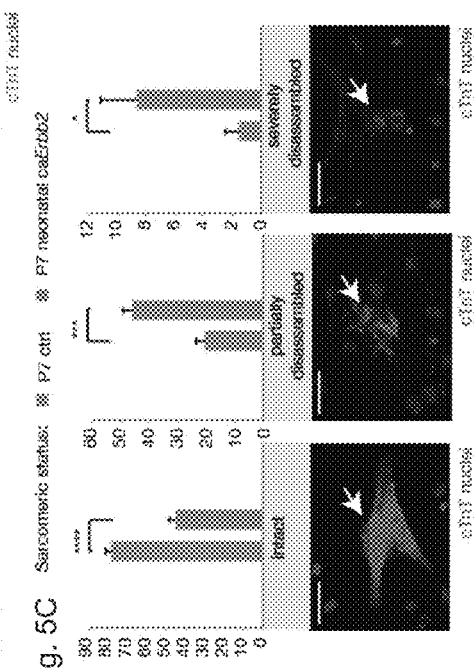
Fig. 5A, Fig. 5B, Fig. 5C, Fig. 5D, Fig. 5E, Fig. 5F, Fig. 5G

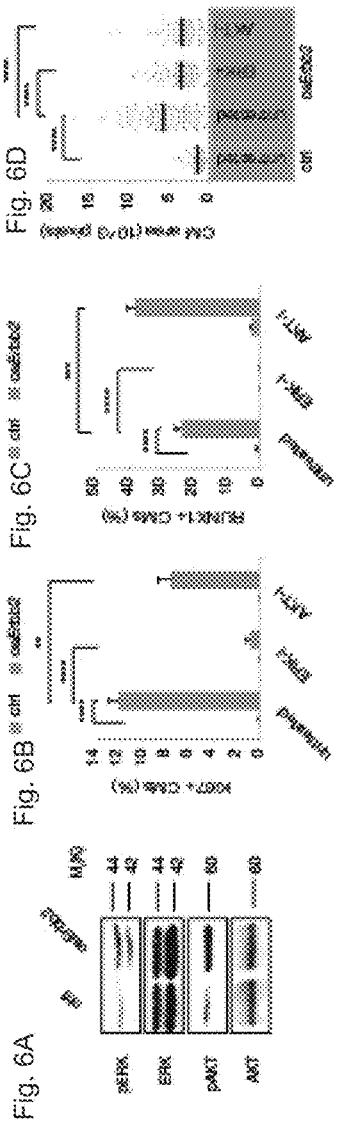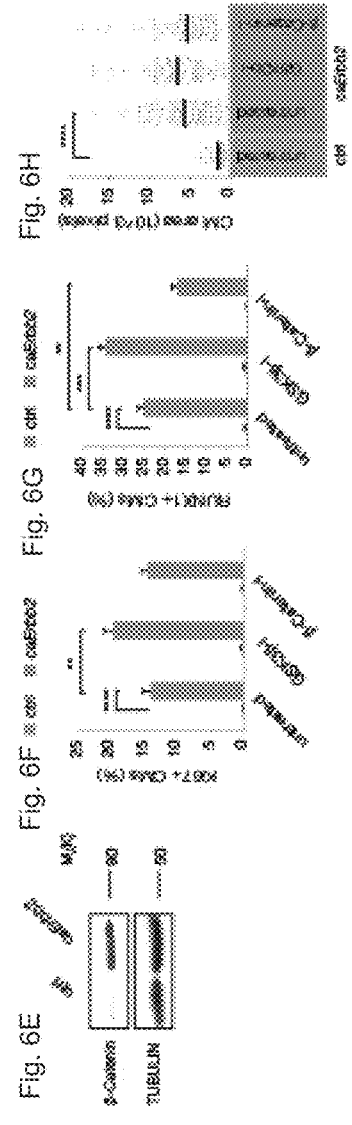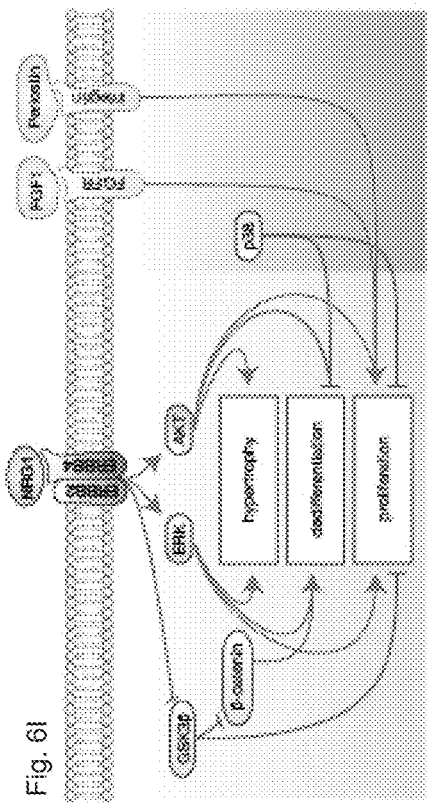

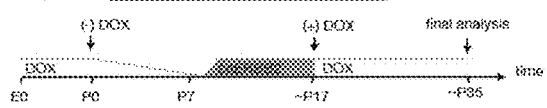
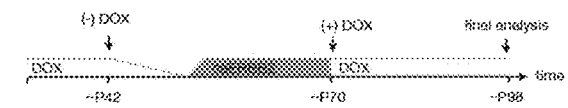
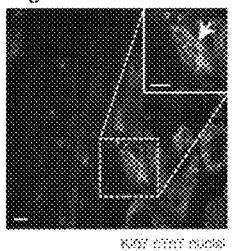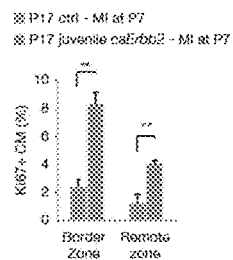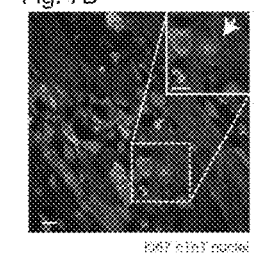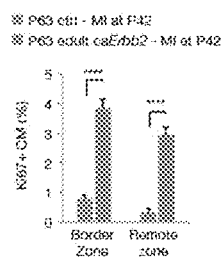
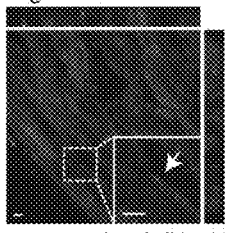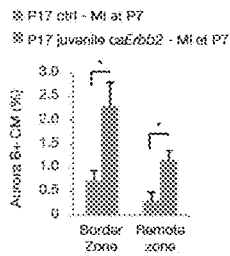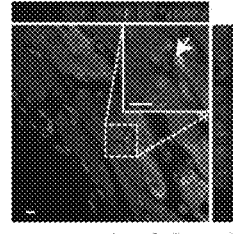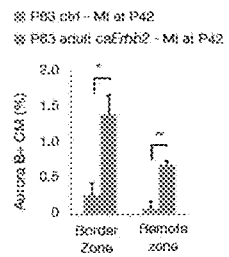
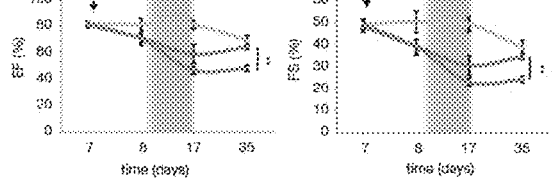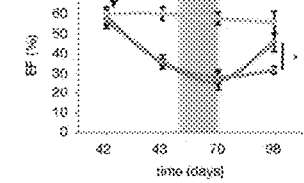
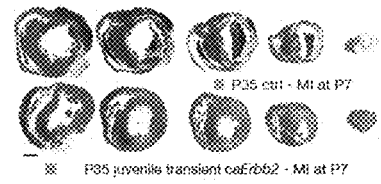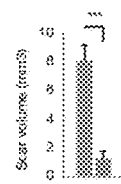
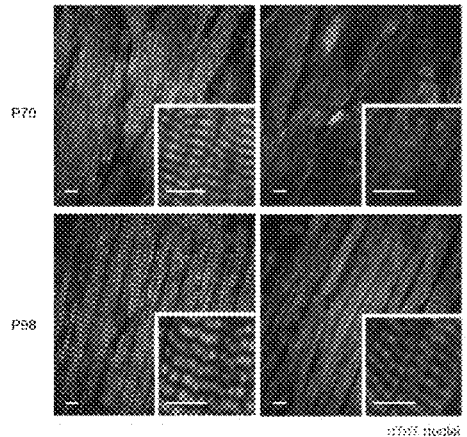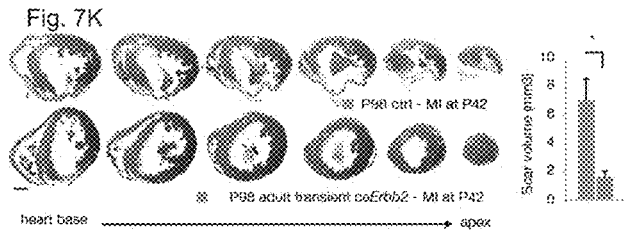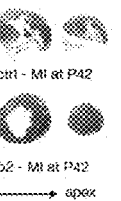

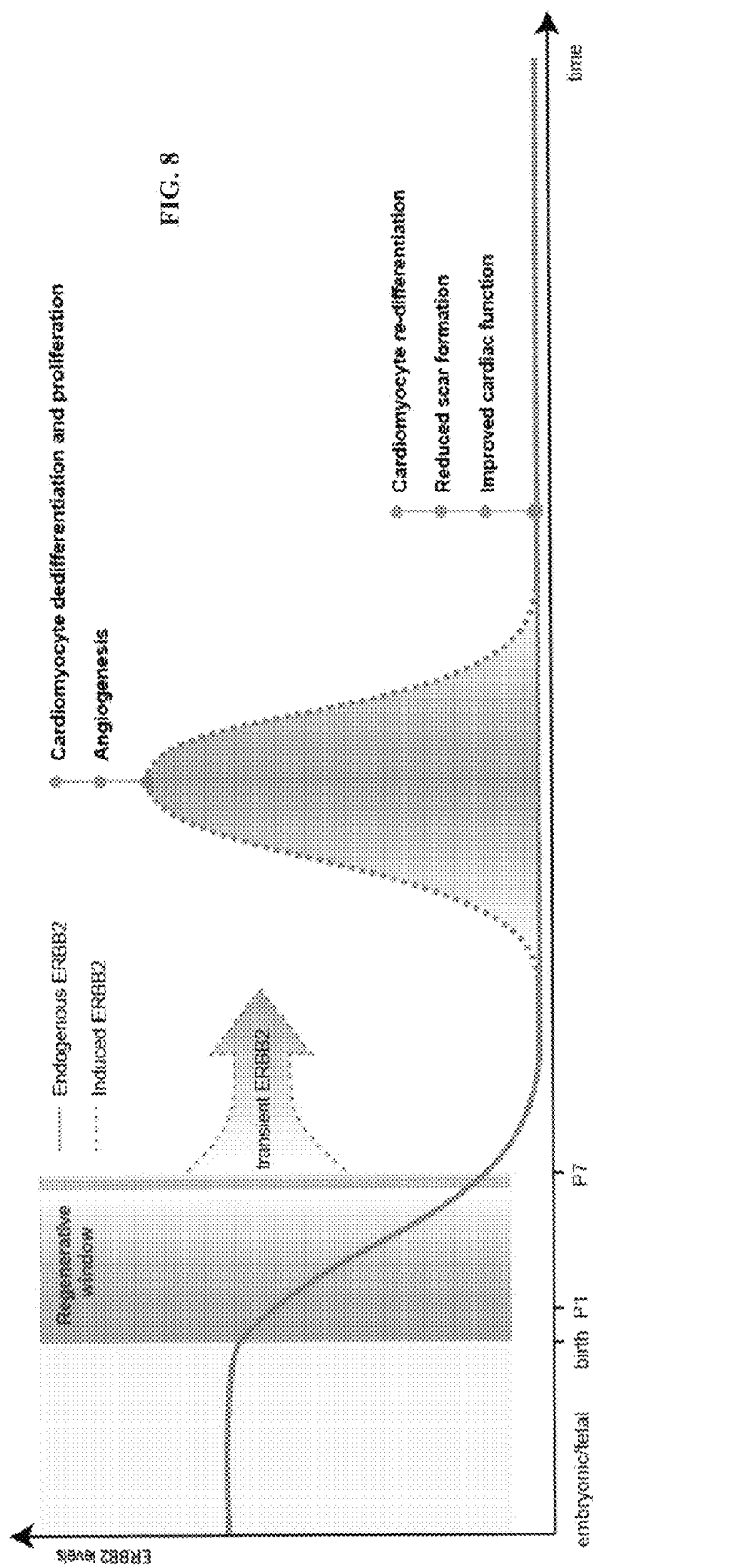

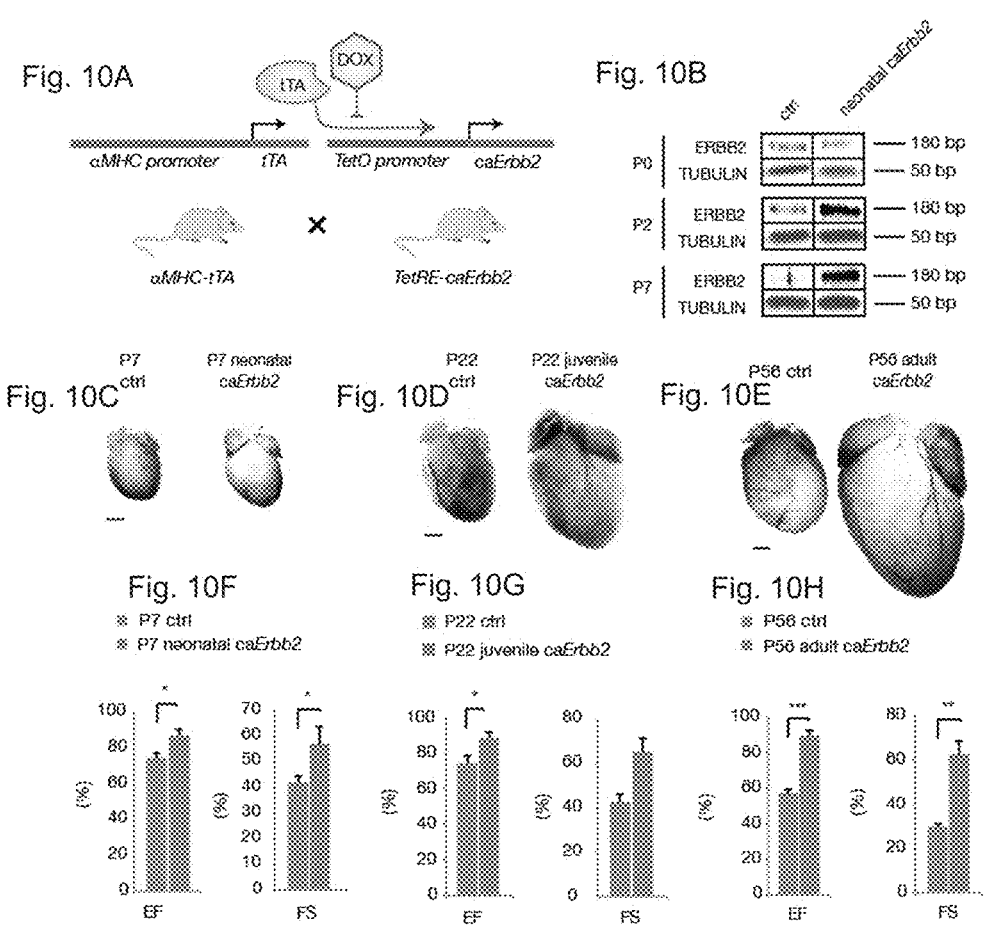

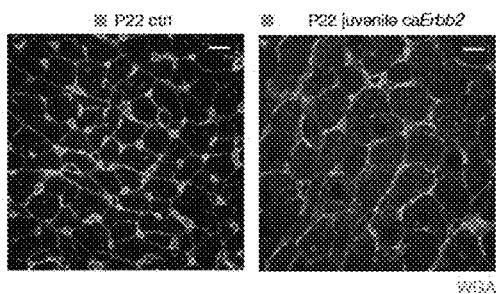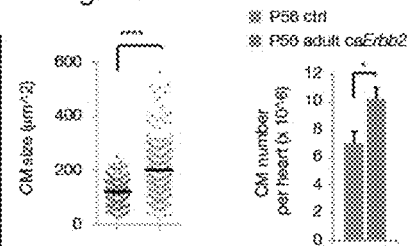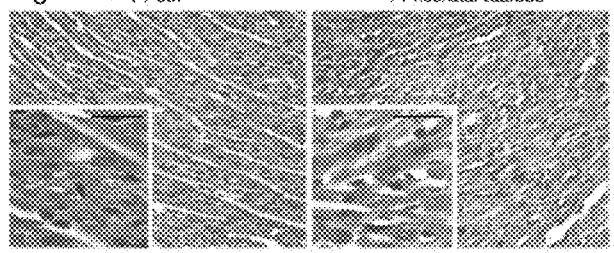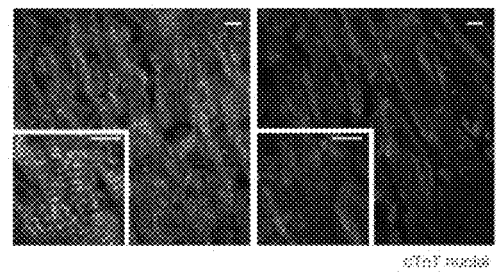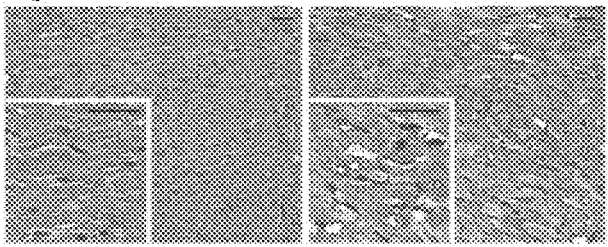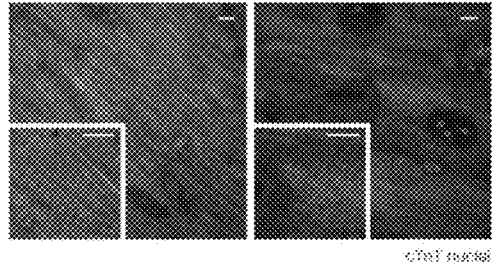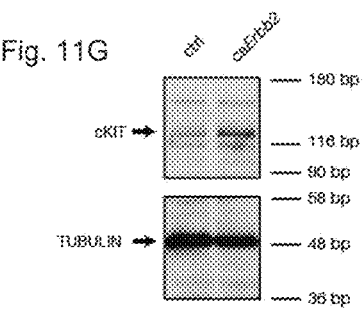

Fig. 13A
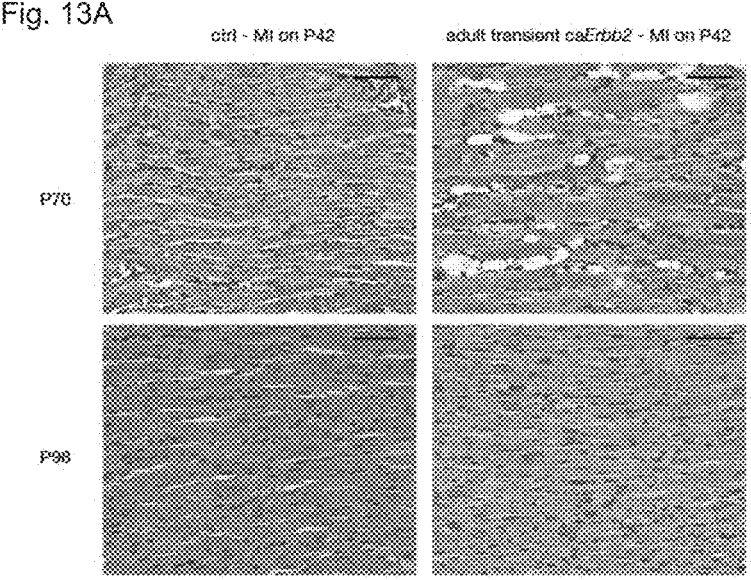
Fig. 13B
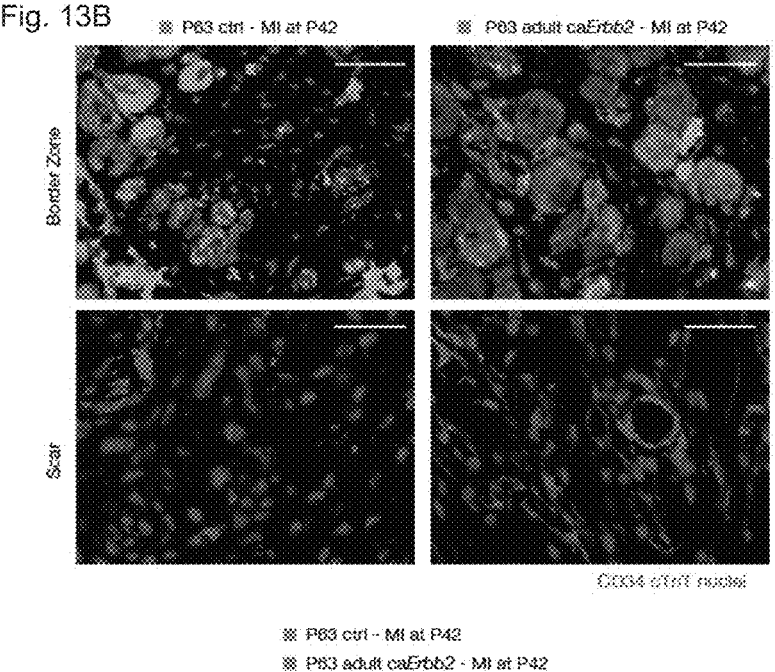
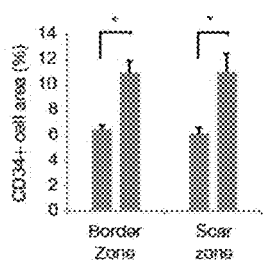

SEQUENCE LISTING

```
<160> NUMBER OF SEQ ID NOS: 34

<210> SEQ ID NO 1
<211> LENGTH: 23
<212> TYPE: PRT
<213> ORGANISM: Artificial sequence
<220> FEATURE:
<223> OTHER INFORMATION: Amino acid sequence of EGF-like domain

<400> SEQUENCE: 1

Ala Glu Lys Glu Lys Thr Phe Cys Val Asn Gly Gly Glu Cys Phe Met
1               5                   10                  15

Val Lys Asp Leu Ser Asn Pro
            20

<210> SEQ ID NO 2
<211> LENGTH: 61
<212> TYPE: PRT
<213> ORGANISM: Artificial sequence
<220> FEATURE:
<223> OTHER INFORMATION: 177-237 residues of NRG-1 betta 2 isoform

<400> SEQUENCE: 2

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln
    50                  55                  60

<210> SEQ ID NO 3
<211> LENGTH: 3678
<212> TYPE: DNA
<213> ORGANISM: homo sapiens
```

```
<400> SEQUENCE: 3
atgaagctgc ggctccctgc cagtcccgag acccacctgg acatgctccg ccacctctac      60
cagggctgcc aggtggtgca gggaaacctg gaactcacct acctgcccac caatgccagc     120
ctgtccttcc tgcaggatat ccaggaggtg cagggctacg tgctcatcgc tcacaaccaa     180
gtgaggcagg tcccactgca gaggctgcgg attgtgcgag gcacccagct ctttgaggac     240
aactatgccc tggccgtgct agacaatgga gacccgctga caataccac ccctgtcaca      300 ggggcctccc caggaggcct gcgggagctg cagcttcgaa gcctcacaga gatcttgaaa     360
ggaggggtct tgatccagcg gaaccccag ctctgctacc aggacacgat tttgtggaag      420
gacatcttcc acaagaacaa ccagctggct ctcacactga tagacaccaa ccgctctcgg     480
gcctgccacc cctgttctcc gatgtgtaag ggctcccgct gctggggaga gagttctgag     540
gattgtcaga gcctgacgcg cactgtctgt gccggtggct gtgcccgctg caaggggcca     600
ctgcccactg actgctgcca tgagcagtgt gctgccggct gcacgggccc caagcactct     660
gactgcctgg cctgcctcca cttcaaccac agtggcatct gtgagctgca ctgcccagcc     720
ctggtcacct acaacacaga cacgtttgag tccatgccca atcccgaggg ccggtataca     780
ttcggcgcca gctgtgtgac tgcctgtccc tacaactacc tttctacgga cgtgggatcc     840 tgcacccteg tctgccccct gcacaaccaa gaggtgacag cagaggatgg aacacagcgg     900
tgtgagaagt gcagcaagcc ctgtgcccga gtgtgctatg gtctgggcat ggagcacttg     960
cgagaggtga gggcagttac cagtgccaat atccaggagt ttgctggctg caagaagatc    1020
tttgggagcc tggcatttct gccggagagc tttgatgggg acccagcctc caacactgcc    1080
ccgctccagc cagagcagct ccaagtgttt gagactctgg aagagatcac aggttaccta    1140
tacatctcag catggccgga cagcctgcct gacctcagcg tcttccagaa cctgcaagta    1200
atccggggac gaattctgca caatggcgcc tactcgctga ccctgcaagg gctgggcatc    1260
agctggctgg ggctgcgctc actgagggaa ctgggcagtg gactggccct catccaccat    1320
aacacccacc tctgcttcgt gcacacggtg ccctgggacc agctctttcg gaacccgcac    1380
caagctctgt ccacactgca caaccggcca gagaacgagt gtgtgggcga gggcctggcc    1440
tgccaccagc tgtgcgcccg agggcactgc tggggtccag ggccacccca gtgtgtcaac    1500
tgcagccagt tccttcgggg ccaggagtgc gtggaggaat gccgagtact gcaggggctc    1560
cccagggagt atgtgaatgc caggcactgt ttgccgtgcc accctgagtg tcagcccag    1620 aatggctcag tgacctgttt tggaccggag gctgaccagt gtgtggcctg tgcccactat    1680
aaggaccctc ccttctgcgt ggcccgctgc cccagcggtg tgaaacctga cctctcctac    1740
atgcccatct ggaagtttcc agatgaggag ggcgcatgcc agccttgccc catcaactgc    1800
acccactcct gtgtggacct ggatgacaag ggctgccccg ccgagcagag agccagccct    1860
ctgacgtcca tcatctctgc ggtggttggc attctgctgg tcgtggtctt ggggtggtc     1920 tttgggatcc tcatcaagcg acggcagcag aagatccgga agtacacgat gcggagactg    1980
ctgcaggaaa cggagctggt ggagccgctg acacctagcg gagcgatgcc aaccaggcg     2040 cagatgcgga tcctgaaaga gacggagctg aggaaggtga aggtgcttgg atctggcgct    2100
tttggcacag tctacaaggg catctggatc cctgatgggg agaatgtgaa aattccagtg    2160
gccatcaaag tgttgaggga aaacacatcc cccaaagcca acaaagaaat cttagacgaa    2220
gcatacgtga tggctggtgt gggctcccca tatgtctccc gccttctggg catctgcctg    2280
acatccacgg tgcagctggt gacacagctt atgcccatg gctgcctctt agaccatgtc    2340
```

```
cgggaaaacc gcggacgcct gggctcccag gacctgctga actggtgtat gcagattgcc    2400
aaggggatga gctacctgga ggatgtgcgg ctcgtacaca gggacttggc cgctcggaac    2460
gtgctggtca agagtcccaa ccatgtcaaa attacagact tcgggctggc tcggctgctg    2520
gacattgacg agacagagta ccatgcagat ggggggcaagg tgcccatcaa gtggatggcg    2580
ctggagtcca ttctccgccg gcggttcacc caccagagtg atgtgtggag ttatggtgtg    2640
actgtgtggg agctgatgac ttttgggggcc aaaccttacg atgggatccc agcccgggag    2700
atccctgacc tgctggaaaa gggggagcgg ctgccccagc ccccatctg caccattgat    2760 gtctacatga tcatggtcaa atgttggatg attgactctg aatgtcggcc aagattccgg    2820
gagttggtgt ctgaattctc ccgcatggcc agggaccccc agcgctttgt ggtcatccag    2880
aatgaggact gggcccagc cagtcccttg acagcacct tctaccgctc actgctggag    2940
gacgatgaca tggggggacct ggtggatgct gaggagtatc tggtacccca gcagggcttc    3000
ttctgtccag accctgcccc gggcgctggg ggcatggtcc accacaggca ccgcagctca    3060
tctaccagga gtggcggtgg ggacctgaca ctagggctgg agccctctga gaggaggcc    3120 cccaggtctc cactggcacc ctccgaaggg gctggctccg atgtatttga tggtgacctg    3180
ggaatggggg cagccaaggg gctgcaaagc ctccccacac atgaccccag ccctctacag    3240
cggtacagtg aggaccccac agtacccctg ccctctgaga ctgatggcta cgttgccccc    3300
ctgacctgca gccccagcc tgaatatgtg aaccagccag atgttcggcc ccagcccct    3360 tcgccccgag agggccctct gcctgctgcc cgacctgctg gtgccactct ggaaaggccc    3420
aagactctct ccccagggaa gaatgggtc gtcaaagacg tttttgcctt tgggggtgcc    3480
gtggagaacc ccgagtactt gacacccag ggaggagctg cccctcagcc ccaccctcct    3540
cctgccttca gcccagcctt cgacaacctc tattactggg accaggaccc accagagcgg    3600
ggggctccac ccagcacctt caaagggaca cctacggcag agaacccaga gtacctgggt    3660
ctggacgtgc cagtgtga                                                3678

<210> SEQ ID NO 4
<211> LENGTH: 1773
<212> TYPE: DNA
<213> ORGANISM: homo sapiens

<400> SEQUENCE: 4
atggggaaag gacgcgcggg ccgagttggc accacagcct tgcctccccg attgaaagag      60
atgaaaagcc aggaatcggc tgcaggttcc aaactagtcc ttcggtgtga aaccagttct     120
gaatactcct ctctcagatt caagtggttc aagaatggga atgagttgaa tcgaaaaaac     180
aaaccacaaa atatcaagat acaaaaaaag ccagggaagt cagaacttcg cattaacaaa     240
gcatcactgg ctgattctgg agagtatatg tgcaaagtga tcagcaaatt aggaaatgac     300
agtgcctctg ccaatatcac catcgtggaa tcaaacgcta catctacatc accactggg     360 acaagccatc ttgtaaaatg tgcggagaag agaaaacttt ctgtgtgaa tggaggggag     420 tgcttcatgg tgaaagacct ttcaaacccc tcgagatact gtgcaagtg cccaaatgag     480 tttactggtg atcgctgcca aaactacgta atggccagct ctacaagca tcttgggatt     540 gaatttatgg aggcggagga gctgtaccag aagagagtgc tgaccataac cggcatctgc     600
atcgccctcc ttgtggtcgg catcatgtgt gtggtggcc actgcaaaac caagaaacag     660
cggaaaaagc tgcatgaccg tcttcggcag agccttcggt ctgaacgaaa caatatgatg     720
```

```
aacattgcca atgggcctca ccatcctaac ccacccccg agaatgtcca gctggtgaat    780
caatacgtat ctaaaaacgt catctccagt gagcatattg ttgagagaga agcagagaca    840
tccttttcca ccagtcacta tacttccaca gcccatcact ccactactgt cacccagact    900
cctagccaca gctggagcaa cggacacact gaaagcatcc tttccgaaag ccactctgta    960
atcgtgatgt catccgtaga aaacagtagg cacagcagcc caactggggg cccaagagga   1020
cgtcttaatg gcacaggagg ccctcgtgaa tgtaacagct tcctcaggca tgccagagaa   1080 accctgatt cctaccgaga ctctcctcat agtgaaaggt atgtgtcagc catgaccacc    1140
ccggctcgta tgtcacctgt agatttccac acgccaagct cccccaaatc gcccccttcg   1200
gaaatgtctc cacccgtgtc cagcatgacg gtgtccatgc cttccatggc ggtcagcccc   1260
ttcatggaag aagagagacc tctacttctc gtgacaccac caaggctgcg ggagaagaag   1320
tttgaccatc accctcagca gttcagctcc ttccaccaca accccgcgca tgacagtaac   1380
agcctccctg ctagccccctt gaggatagtg gaggatgagg agtatgaaac gacccaagag   1440
tacgagccag cccaagagcc tgttaagaaa ctcgccaata gccggcgggc caaaagaacc   1500
aagcccaatg ccacgttgc taacagattg gaagtggaca gcaacacaag ctcccagagc    1560
agtaactcag agagtgaaac agaagatgaa agagtaggtg aagatacgcc tttcctgggc   1620
atacagaacc ccctggcagc cagtcttgag gcaacacctg ccttccgcct ggctgacagc   1680
aggactaacc cagcaggccg cttctcgaca caggaagaaa tccaggccag gctgtctagt   1740
gtaattgcta accaagaccc tattgctgta taa                                1773

<210> SEQ ID NO 5
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 5
ggcattaaag cagcgtatcc                                                 20

<210> SEQ ID NO 6
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 6
ggccagctaa acatgcttca                                                 20

<210> SEQ ID NO 7
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 7
ccaccctctc gctccagctg gtgga                                           25

<210> SEQ ID NO 8
<211> LENGTH: 22
<212> TYPE: DNA
<213> ORGANISM: Artificial sequence
<220> FEATURE:
<223> OTHER INFORMATION: Single strand DNA oligonucleotide
```

```
<400> SEQUENCE: 8
tttatgtggg cacgcttaga ac                                        22

<210> SEQ ID NO 9
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 9
aagaagagcc caagctgga                                            19

<210> SEQ ID NO 10
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 10
cgctgtgggg cattttactt tag                                       23

<210> SEQ ID NO 11
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 11
ctgttcctgt acggcatgg                                            19

<210> SEQ ID NO 12
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 12
acaccagaga cggaaatcca tc                                        22

<210> SEQ ID NO 13
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 13
cgggcctctt cgctattacg ggagc                                     25

<210> SEQ ID NO 14
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 14
ctagaagtct gatttgcggt at                                        22

<210> SEQ ID NO 15
```

```
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 15
gtgtacggtg ggaggcctat                                              20

<210> SEQ ID NO 16
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 16
catgtccaga tcgaaatcgt c                                            21

<210> SEQ ID NO 17
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 17
atcgccctgt tggtggtcgg                                              20

<210> SEQ ID NO 18
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 18
gccccaaagc caacgtggag t                                            21

<210> SEQ ID NO 19
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 19
cgctgcccca gtggtgtgaa g                                            21

<210> SEQ ID NO 20
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 20
gacatcaaag agaagctgtg                                              20

<210> SEQ ID NO 21
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 21
```
gagagaaaga aaccagagtg                           20

<210> SEQ ID NO 22
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 22
aattcaagat gcagaagctg                           20

<210> SEQ ID NO 23
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 23
aatcctaatg caaacaaggg                           20

<210> SEQ ID NO 24
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 24
ttgggaaatt catccgaatc                           20

<210> SEQ ID NO 25
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 25
tggccggcag cgtttctgag                           20

<210> SEQ ID NO 26
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 26
agcttctgcc gctgtttctt ggt                       23

<210> SEQ ID NO 27
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 27
gcggcatcag ctgcgtaacc                           20

<210> SEQ ID NO 28
<211> LENGTH: 20
<212> TYPE: DNA

```
<213> ORGANISM: Artificial sequence
<220> FEATURE:
<223> OTHER INFORMATION: Single strand DNA oligonucleotide

<400> SEQUENCE: 28
gcagcctcgt tcgtccaggt                                              20

<210> SEQ ID NO 29
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 29
actccatacc gataaaggaa g                                            21

<210> SEQ ID NO 30
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 30
gtctagcagg ttcttgaaat c                                            21

<210> SEQ ID NO 31
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 31
gaattttgag gtctctgctg                                              20

<210> SEQ ID NO 32
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 32
cagaaggtag gtctctatgt c                                            21

<210> SEQ ID NO 33
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 33
ccagaaggta ggtctctatg                                              20

<210> SEQ ID NO 34
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 34
gtcggctcgc ggcaaaaagc                                              20
```

METHODS, KITS AND DEVICES FOR PROMOTING CARDIAC REGENERATION

RELATED APPLICATION

This application claims the benefit of priority under 35 USC 119(e) of U.S. Provisional Patent Application No. 62/158,111 filed May 7, 2015, the contents of which are incorporated herein by reference in their entirety.

SEQUENCE LISTING STATEMENT

The ASCII file, entitled 65911SequenceListing.txt, created on May 5, 2016, comprising 14,806 bytes, submitted concurrently with the filing of this application is incorporated herein by reference.

FIELD AND BACKGROUND OF THE INVENTION

The present invention, in some embodiments thereof, relates to methods, kits and devices for promoting cardiac regeneration.

Heart regeneration is a primary biomedical research goal. Myocardial infarction (MI) is a life-threatening injury causing permanent loss of cardiomyocytes (CMs). MI events are experienced by over 900,000 people per year in the United States alone, and about one in four will die. Scars form in MI survivors, increasing susceptibility to compensatory pathology, aneurysm, additional MI events, heart failure, and sudden death. Thus, a major goal of regenerative medicine is to replenish lost CMs, avoid scar-associated pathology, and improve outcomes after MI. Adult mammalian cardiomyocytes (CMs) have limited proliferative capacity[1, 2] with poor ability to replace lost tissue after acute ischemic injury[3-7]. Hence, a scientific and clinical imperative is to find ways of stimulating regenerative capacity in human hearts[3-7]. Cardiac and non-cardiac stem cell populations have been emphasized for use in heart regeneration therapies. However, there is general consensus that the modest benefits seen after stem cell transplantation do not arise from their differentiation into CMs[1,2]. Instead transplanted cells survive only transiently and likely affect endogenous repair mechanisms via paracrine action. The potential use of pluripotent stem cell-derived CMs for heart therapy also faces daunting challenges with cell maturation, arrhythmogenesis, immunosuppression, and the need for scale-up[1,2]. The ability to stimulate robust endogenous cardiac regeneration without adding exogenous cells would avoid these issues, and remains the field's "holy grail".

Over the first week of postnatal life in mice, most CMs exit the cell cycle and continue to grow by hypertrophy (increase in cell size)[8, 9], although they undergo an additional burst of proliferation in the pre-adolescent period[10]. Postnatal CM differentiation is paralleled in mice by binucleation of CMs and in humans by increased ploidy[8, 9]. The molecular mechanisms regulating the transition from CM hyperplastic (increase in cell number) to hypertrophic growth at early postnatal stages, and in particular how CM proliferation capacity might be re-activated in adult life to foster regeneration, are poorly understood.

A robust regenerative response to injury occurs in adult hearts of lower vertebrates such as zebrafish and amphibians[4, 11]. Regeneration has also been demonstrated in mammalian hearts during the first week of postnatal life[12], corresponding to the time window during which CMs continue to proliferate[9], and by post-natal day 7 (P7) fibrotic scar formation predominates over tissue replacement[12]. In adult zebrafish and neonatal mice, the regenerative response involves CM proliferation[4, 11-13].

Signalling networks that drive embryonic heart development may also control aspects of heart regeneration[6, 14]. The ligand-receptor network consisting of Neuregulin-1 (NRG1), and its tyrosine kinase receptors ErbB4, ErbB3 and ErbB2, plays critical roles during heart development[15-20]. ErbB4 and ErbB2 are the NRG1 receptors expressed most prominently in embryonic, fetal and neonatal CMs, and recombinant NRG1 stimulates embryonic/fetal/neonatal CM proliferation, hypertrophic growth, sarcomerogenesis and survival ex vivo[18, 21]. Decreased NRG1 signalling in postnatal hearts is associated with adverse cardiac function and susceptibility to stress[22, 23]. Administration of NRG1 improves cardiac function following injury in adult mice[22-27] and in heart failure patients[22, 23.25, 28-31]. However, recent advanced clinical trials did not reach the expected results, suggesting a missing component in the Nrg-1 signalling pathway. This was suggested to stem from multiple mechanisms, including improved CM survival and contractility[22] as well as induction of adult CM proliferation[26], although the contribution of the latter one is controversial[22, 32]. Nevertheless, how ErbB2 impacts cardiac regeneration is unknown.

The Erbb2 gene was originally identified due to its oncogenic activity and its overexpression is associated with poor prognosis in cancer patients[33-35]. Unlike ErbB4, ErbB2 is unable to bind ligands, yet, it is the preferred heterodimerization partner, stabilizing ligand binding, enhancing and diversifying ligand-induced receptor signalling[34, 36-38]. In the myocardium, ErbB2 forms heterodimers with ErbB4[39].

RELATED ART

U.S. Patent Application Publication Nos.:
20150065418
20140227247
20140031284
20130287728
20130040879
Fukazawa et al. *J Mol Cell Cardiol.* 2003 December; 35(12): 1473-9.

SUMMARY OF THE INVENTION

According to an aspect of some embodiments of the present invention there is provided a method of potentiating cardiac regeneration with neuregulin treatment in a subject in need thereof, the method comprising administering to the subject a therapeutic effective amount of an agent which upregulates activity or expression of ErbB-2, thereby potentiating cardiac regeneration with neuregulin treatment.

According to an aspect of some embodiments of the present invention there is provided a method of regenerating a cardiac tissue in a subject in need thereof, the method comprising administering to the subject a therapeutic effective amount of an agent which upregulates activity or expression of ErbB-2, wherein the agent is not neuregulin, thereby regenerating the cardiac tissue.

According to an aspect of some embodiments of the present invention there is provided a kit for cardiac repair comprising:
(i) an agent which upregulates activity or expression of ErbB-2; and
(ii) neuregulin.

According to an aspect of some embodiments of the present invention there is provided an implantable device for cardiac repair comprising an agent which upregulates activity or expression of ErbB-2.

According to some embodiments of the invention, the implantable device further comprises neuregulin.

According to some embodiments of the invention, the agent which upregulates activity or expression of ErbB-2 is in a sustained release form.

According to an aspect of some embodiments of the present invention there is provided a method of identifying an agent useful in cardiac regeneration, the method comprising:

(a) contacting the agent with post natal cardiomyocytes that do not express ErbB-2;

(b) measuring an activity or expression of the ErbB-2 in the cardiomyocytes, wherein an upregulation in the ErbB-2 activity or expression following the contacting is indicative that the agent is useful cardiac tissue regeneration.

According to some embodiments of the invention, the cardiomyocytes correspond to murine P7.

According to some embodiments of the invention, the agent which upregulates activity or expression of ErbB-2 is an ErbB-2 activating antibody.

According to some embodiments of the invention, the agent which upregulates activity or expression of ErbB-2 activates a signaling effector downstream of the ErbB-2.

According to some embodiments of the invention, the signaling effector comprises is selected from the group consisting of Erk and Akt.

According to some embodiments of the invention, the agent which upregulates activity or expression of ErbB-2 is selected from the group consisting of FGF1 and periostin.

According to some embodiments of the invention, the agent which upregulates activity or expression of ErbB-2 inhibits a signaling molecule downstream of the ErbB-2.

According to some embodiments of the invention, the signaling molecule is selected from the group consisting of GSK3β and p38.

According to some embodiments of the invention, the agent which upregulates activity or expression of the ErbB-2 is selected from the group consisting of a nucleic acid molecule, a small molecule, an antibody, a polypeptide and a peptide.

According to some embodiments of the invention, the method further comprises administering the neuregulin to the subject.

According to some embodiments of the invention, the neuregulin is selected from the group consisting of neuregulin-1, neuregulin-2, neuregulin-3 and neuregulin-4.

According to some embodiments of the invention, the subject has or at risk of a heart failure selected from the group consisting of a congestive heart failure, myocardial infarction, tachyarrhythmia, familial hypertrophic cardiomyopathy, ischemic heart disease, idiopathic dilated cardiomyopathy and myocarditis.

According to some embodiments of the invention, the heart failure is caused by a factor selected from the group consisting of an ischemic factor, a congenital factor, a rheumatic factor, a viral factor, a toxic factor and an idiopathic factor.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 9A:
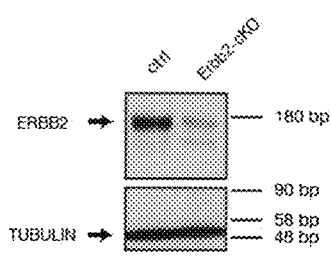
Figure 9B:
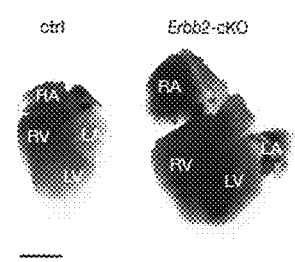
Figure 9C:
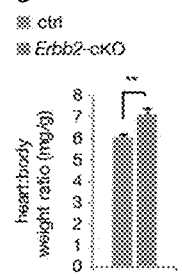
Figure 9D:
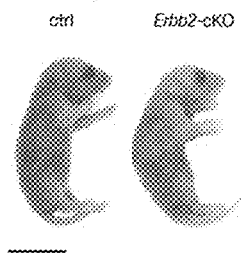
Figure 9E:
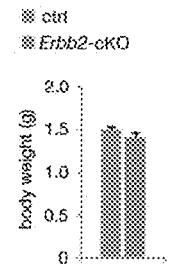

FIGS. 1A-I show that NRG1-induced cardiomyocyte cell cycle progression is diminished during the first week of post-natal life, in correlation with reduced ErbB2 levels. FIGS. 1A-D—1-day-old (P1) and 7-day-old (P7) mouse CMs were cultured in vitro and stimulated with various doses of NRG1; cardiomyocytes (CMs) were identified by RFP-labelling (detailed in the "Examples" section) in FIG. 1A, FIG. 1C and FIG. 1D or by cTnI staining in FIG. 1B and analysed by immunofluorescence analysis for (FIG. 1A) cell-cycle activity (Ki67), (FIG. 1B) DNA synthesis (BrdU), (FIG. 1C) karyokinesis (pH3) and (FIG. 1D) cytokinesis (AuroraB) (n=14615 CMs pooled from the analysis of 36 samples in FIG. 1A; n=9571 CMs pooled from the analysis of 26 samples in FIG. 1B; n=13457 CMs pooled from the analysis of 27 samples in FIG. 1C; n=70092 CMs pooled from the analysis of 39 samples in FIG. 1D); representative pictures are provided; scale bar 30 μm; (FIG. 1E) Quantification of CMs generation in P1 and P7 heart cell culture with/without administration of NRG1 (100 ng/ml) over a period of 3 days (n=1119 CMs pooled from the analysis of 16 samples); (FIG. 1F) mRNA expression levels of Nrg1, NRG receptor Erbb4 and co-receptor Erbb2 in P1 and P7 heart lysates, measured by real-time (RT)-PCR analysis (n=14 mice) (FIGS. 1G-H) Western blot analysis of ErbB2 and phospho-ErbB2 (pErbB2) protein levels in P1 and P7 heart lysates; representative pictures and quantifications are provided (n=10 mice); Immunofluorescence analysis of ErbB2 and cardiac Troponin T (cTnT) in P1, P7 and P28 heart sections. Representative images were obtained using a spinning-disk confocal microscope; scale bar 10 μm.

In all panels numerical data are presented as mean+s.e.m; statistical significance was calculated using one-way ANOVA followed by Tukey's test in FIGS. 1A-D and two-tailed unpaired Student's t-test in FIGS. 1E, 1F and 1H; results are marked with one asterisk (*) if $p<0.05$, two () if $p<0.01$, three (*) if $p<0.001$ and four (****) if $p<0.0001$; statistics source data can be found in Table 3.

FIGS. 2A-J show that ErbB2 is required for NRG1-induced cardiomyocyte proliferation. (FIG. 2A) A schematic diagram depicting the generation of CM restricted Erbb2 Knock-Out (Erbb2-cKO) mice; (FIG. 2B) Kaplan-Meier survival curves of Erbb2-cKO compared to control (ctrl) mice (n=89 mice); (FIG. 2C) Hematoxylin-Eosin (H&E) histological analysis showing dilated cardiomyopathy with reduced wall thickness in Erbb2-cKO compared ctrl mice at birth; Erbb2-cKO hearts had intact inter-ventricular septum (IVS) and mature valve leaflets; scale bar 1 mm; (FIG. 2D) Echocardiographic analysis of ctrl and Erbb2-cKO mice at birth showing decreased left ventricle (LV) anterior and posterior-wall (LVAW and LVPW) thickness, increased LV end-diastolic and end-systolic dimensions (LVEDD and LVESD), and decreased ejection fraction (EF) and fractional shortening (FS) in Erbb2-cKO mice (n=6 mice); representative images are provided; scale bar 1 mm (vertical axis) and 50 ms (horizontal axis); (FIG. 2E) CM cell number following isolation of RFP-labelled-CMs (see "Methods" section for details) in ctrl and Erbb2-cKO mice at birth (n=7 mice); (FIG. 2F) Evaluation of CM cell cycle activity by immunofluorescence analysis of Ki67 and cardiac Troponin T (cTnT) in LV P0 heart sections (n=1518 CMs pooled from the analysis of 6 mice); representative images obtained using a spinning-disk confocal microscope are provided; scale bar 10 μm; (FIG. 2G) Erbb2-cKO hearts display a compensatory increase in Nrg1 expression levels at birth, as shown by RT-PCR analysis (n=6 mice); (FIGS. 2H-I) Quantification of immunofluorescence analysis of cell cycle activity (Ki67) and karyokinesis (pH3) in response to NRG1 administration in vitro in RFP-labelled-CMs isolated from P1 Erbb2-cKO and ctrl mice (n=25036 CMs pooled from the analysis of 36 samples in h; n=21423 CMs pooled from the analysis of 36 samples in FIG. 2I); (FIG. 2J) Quantification of newly formed CMs in response to administration of NRG1 (100 ng/ml) over a period of 3 days in heart cell culture isolated from P1 ctrl and Erbb2-cKO mice (n=859 CMs pooled from the analysis of 12 samples).

In all panels numerical data are presented as mean+s.e.m; statistical significance was calculated using log-rank (Mantel-Cox) test for lifespan in FIG. 2B, two-tailed unpaired t-test in FIGS. 2D-G and FIG. 2J and one-way ANOVA followed by Tukey's test in FIG. 2H, FIG. 2I; results are marked with one asterisk (*) if $p<0.05$, two () if $p<0.01$, three (*) if $p<0.001$ and four (****) if $p<0.0001$; statistics source data can be found in Table 3.

FIGS. 3A-O show that post-natal activation of ErbB2 signalling leads to cardiomegaly. (FIGS. 3A-C) Experimental designs for CM specific overexpression of a constitutively active Erbb2 (caErbb2) starting at various post-natal stages: neonatal (~P1-P2), juvenile (~P8-P9) and adult (~5-weeks). Overexpression begins ~8-9 days after DOX removal due to gradual clearance from tissues; (FIGS. 3D-F) Heart weight:tibia length ratio in ctrl and caErbb2 mice (n=14 mice in FIG. 3D; n=14 mice in FIG. 3E; n=20 mice in FIG. 3F); representative images of H&E histological analysis of hearts are provided; scale bar 1 mm; (FIGS. 3G-I) Left ventricular morphology and function quantified by echocardiographic analysis of left ventricular anterior and posterior wall thickness (LVAW and LVPW), left ventricular end-diastolic and end-systolic dimensions (LVEDD and LVESD) and stroke volume (SV) in ctrl and caErbb2 mice (n=15 mice in FIG. 3G, 16 mice in FIG. 3H; n=11 mice in FIG. 3I); representative images are provided; scale bar 1 mm (vertical axis) and 200 ms (horizontal axis); (FIGS. 3J-L) Body growth rate of ctrl and caErbb2 mice (n=21 in FIG. 3J; n=25 mice in FIG. 3K; n=10 mice in FIG. 3L); (FIGS. 3M-O) Survival rate of ctrl and caErbb2 mice (n=72 mice in FIG. 3M; n=171 in FIG. 3N; n=65 mice in FIG. 3O).

In all panels numerical data are presented as mean+s.e.m; statistical significance was calculated using two-tailed unpaired Student's t-test in FIGS. 3D-I, two-way ANOVA followed by Sidak's test in FIGS. 3J-L and log-rank (Mantel-Cox) test for lifespan in FIGS. 3M-O; results are marked with one asterisk (*) if $p<0.05$, two () if $p<0.01$, three (*) if $p<0.001$ and four (****) if $p<0.0001$; statistics source data can be found in Table 3.

FIGS. 4A-K show that post-natal activation of ErbB2 signalling promotes extensive cardiomyocyte proliferation and hypertrophy in vitro and in vivo.

(FIG. 4A) CM size (area) quantification based on cardiac Troponin T (cTnT) staining in P7 ctrl and caErbb2 heart cell culture (n=286 CMs pooled from the analysis of 7 mice); (FIGS. 4B-C) RT-PCR analysis of pathological hypertrophic markers (Nppa, Nppb, Acta1 and β/αMHC ratio) in P7 ctrl and caErbb2 heart lysates (n=7 mice); (FIG. 4D) CM cross-section area evaluation by WGA immunofluorescence analysis of P56 ctrl and adult caErbb2 LV heart sections (n=392 CMs pooled from the analysis of 6 mice); representative images are provided; scale bar 10 μm; (FIG. 4E) In vitro evaluation of CM proliferation by immunofluorescence analysis of cell-cycle re-entry (Ki67, n=4192 CMs pooled from the analysis of 41 samples), karyokinesis (pH3, n=1849 CMs pooled from the analysis of 41 samples) and cytokinesis (AuroraB, n=2946 CMs pooled from the analysis of 41 samples) in P7 ctrl and caErbb2 CMs cultured for 2 days; representative images are provided; scale bar 60 μm; (FIGS. 4F-G) In vivo evaluation of CM cell-cycle re-entry by Ki67 immunofluorescence analysis in ctrl and caErbb2 LV heart sections (n=1574 CMs pooled from the analysis of 6 mice in FIG. 4F, n=2410 CMs pooled from the analysis of 6 mice in FIG. 4G); Representative images obtained using a spinning-disk confocal microscope are provided; scale bar 10 μm; (FIGS. 4H-J) Quantification and representative images taken from a 12-hour time-lapse movie of (FIG. 4H) mono-nucleated CM cell division and binucleation events (n=698 mono-nucleated CMs pooled from the analysis of 7 mice) or (FIG. 4J) bi-nucleated CM cell divisions (n=249 bi-nucleated CMs pooled from the analysis of 7 mice) in P7 ctrl and neonatal caErbb2 TMRE-labelled CMs (see "Methods" section in the Examples section for details); scale bar 30 μm; Percentage of caErbb2 mono-nucleated CMs undergoing karyokinesis and proceeding to cell division or binucleation is provided in FIG. 4I; (FIG. 4K) CM cell nucleation analysis in P7 ctrl and caErbb2 heart cells cultured in vitro for 2 days (n=1965 CMs pooled from the analysis of 9 mice).

In all panels numerical data are presented as mean+s.e.m; statistical significance was calculated using two-tailed unpaired t-test in FIGS. 4A-K; results are marked with one asterisk (*) if $p<0.05$, two () if $p<0.01$, three (*) if $p<0.001$ and four (****) if $p<0.0001$; statistics source data can be found in Table 3.

FIGS. 5A-G show post-natal activation of ErbB2 signalling promotes cardiomyocyte dedifferentiation.

(FIG. 5A) H&E histological analysis of LV heart sections; scale bar 25 μm; (FIG. 5B) In vivo CM sarcomeric status evaluation by immunofluorescence analysis of cardiac Troponin T (cTnT) in P56 ctrl and caErbb2 heart sections; Images were obtained using a spinning-disk confocal microscope; scale bar 5 μm; (FIG. 5C) CM sarcomeric status quantification by cTnT immunofluorescence analysis of P7 ctrl and neonatal caErbb2 CMs cultured in vitro for 2 days (n=245 CMs pooled from the analysis of 11 mice); representative pictures of CMs with intact, partially disassembly and severely assembly sarcomere is provided; scale bar 60 μm; (FIG. 5D) CM dedifferentiation analysis by immunofluorescence staining of the cardiac muscle lineage marker Nkx2.5 and sarcomeric cTnT (n=924 Nkx2.5+ cells pooled from the analysis of 11 mice); (FIGS. 5E-G) CM dedifferentiation analysis by immunofluorescence staining for αSMA/cTnI (n=598 CMs pooled from the analysis of 8 mice), RUNX1/cTnT (n=1919 CMs pooled from the analysis of 11 mice), and DAB2/cTnT (n=577 CMs pooled from the analysis of 6 mice) of P7 ctrl and neonatal caErbb2 heart cells cultured in vitro for 2 days; representative images are provided; scale bar 60 μm.

In all panels numerical data are presented as mean+s.e.m; statistical significance was calculated using two-tailed unpaired Student's t-test in FIGS. 5C-G; results are marked with one asterisk (*) if p<0.05, two () if p<0.01, three (*) if p<0.001 and four (****) if p<0.0001; statistics source data can be found in Table 3.

FIGS. 6A-I show that ERK, AKT and GSK3β/β-Catenin differentially mediate ErbB2-induced cardiomyocyte proliferation, dedifferentiation and hypertrophy.

(FIG. 6A) Western blot analysis of phospho-ERK (pERK), ERK, phospho-AKT(pAKT) and AKT in P7 ctrl and neonatal caErbb2 heart lysates; (FIGS. 6B-D) P7 ctrl and neonatal caErbb2 heart cells were treated with pharmacological inhibitors of ERK and AKT (ERK-i and AKT-i) in vitro for 2 days; CMs were identified by Troponin T (cTnT) staining and analysed by immunofluorescence analysis for (FIG. 6B) cell-cycle re-entry (Ki67), (FIG. 6C) dedifferentiation marker (RUNX1) and (D) cell area (n=5332 CMs pooled from the analysis of 54 samples in FIG. 6B; n=3634 CMs pooled from the analysis of 37 samples in C; n=338 CMs pooled from the analysis of 15 samples in FIG. 6D); (FIG. 6E) Western blot analysis of β-Catenin in P7 ctrl and neonatal caErbb2 heart lysates; (FIGS. 6F-H) Immunofluorescence analysis of (FIG. 6F) cell-cycle re-entry (Ki67), (FIG. 6G) dedifferentiation (RUNX1) and (FIG. 6H) cell area of P7 ctrl and caErbb2 CMs following administration of inhibitors of GSK3β and β-Catenin (GSK3β-i and β-Catenin-i) for 2 days in vitro (n=5807 CMs pooled from the analysis of 46 samples in FIG. 6F, n=4778 CMs pooled from the analysis of 44 samples in FIG. 6G, n=367 CMs pooled from the analysis of 14 samples in FIG. 6H); (FIG. 6I) Schematic diagram of ErbB2 downstream signalling pathways and modulators regulating CM dedifferentiation, proliferation and hypertrophic growth.

In all panels numerical data are presented as mean+s.e.m; statistical significance was calculated using one-way ANOVA followed by Tukey's test in FIGS. 6B-D and FIGS. 6F-H; results are marked with one asterisk (*) if p<0.05, two () if p<0.01, three (*) if p<0.001 and four (****) if p<0.0001; statistics source data can be found in Table 3.

FIGS. 7A-K show that transient ErbB2 induction triggers CM dedifferentiation, proliferation and cardiac regeneration following injury in juvenile and adult stages. (FIGS. 7A-B) Experimental design for cardiac regeneration analysis following injury in mice transiently overexpressing caErbb2 at juvenile (~P8-9 to P17) or adult (~5 weeks to ~2-months) stage; (FIGS. 7C-F) In vivo evaluation of CM cell-cycle re-entry and cytokinesis by immunofluorescence analysis of Ki67 and AuroraB in heart sections of (FIGS. 7C, 7E) ~10-days post-MI (~P17) ctrl and juvenile caErbb2 and (FIGS. 7D, 7F) ~3-weeks post-MI (~P63) ctrl and adult caErbb2 following myocardial infarction according to the scheme in FIGS. 7A and 7B (n=4237 CMs pooled from the analysis of 7 mice in FIG. 7C; n=5617 CMs pooled from the analysis of 6 mice in FIG. 7D; n=3789 CMs pooled from the analysis of 7 mice in FIG. 7E; n=2629 CMs pooled from the analysis of 6 mice in FIG. 7F); CMs were identified by staining with antibodies for cardiac Troponin T or I (cTnT, cTnI); representative pictures obtained using a spinning-disk confocal microscope of cell-cycle activity or cytokinesis of caErbb2 CMs in the border zone are provided; scale bar 5 μm; (FIGS. 7G-H) Serial echocardiographic measurements of ejection fraction (EF) and fractional shortening (FS) of uninjured and injured ctrl and caErbb2 mice following myocardial infarction according to the schema in FIGS. 7A and 7B (n=18 mice in FIG. 7G; n=13 mice in FIG. 7H); (FIG. 7I) In vivo CM sarcomeric status evaluation by immunofluorescence analysis of sarcomeric Troponin T (cTnT) in remote zone of ctrl and adult transient caErbb2 heart sections ~1-month-post-MI (~P70) and ~2-months-post-MI (~P98, ~one-month after caErbB2 signal termination); representative images obtained using a spinning-disk confocal microscope are provided; scale bar 5 μm; (FIGS. 7J-K) Scar quantification based on masson trichrome staining of heart sections of (J) ~1-month post-MI (~P35) ctrl and juvenile transient caErbb2 mice and (FIG. 7K) ~2-months post-MI (~P98) ctrl and transient adult caErbb2 mice (n=17 mice in FIG. 7J; n=9 mice in FIG. 7K); representative pictures are provided; scale bar 1 mm.

In all panels numerical data are presented as mean+s.e.m; statistical significance was calculated using two-tailed unpaired t-test in FIGS. 7C-F, 7J, 7K, two-way ANOVA followed by Sidak's test in FIGS. 7G, 7H; results are marked with one asterisk (*) if p<0.05, two () if p<0.01, three (*) if p<0.001 and four (****) if p<0.0001; Statistics source data can be found in Table 3.

FIG. 8 is a model illustration depicting that ErbB2 signalling triggers robust CM dedifferentiation and proliferation and re-activates a dormant postnatal regenerative window in mice. A schematic diagram of the role of ErbB2 in controlling post-natal CM proliferation and heart regenerative ability. A physiological reduction of ErbB2 levels (red line) during the first week of post-natal life reduces CM proliferative ability; Transient augmentation of ErbB2 signalling (red dashed line) triggers CM dedifferentiation and proliferation and increased angiogenesis. Termination ErbB2 signalling facilitates CM re-differentiation leading to reduced scar formation and improved cardiac function. It is therefore suggested that transient activation of ErbB2 signalling re-opens the cardiac regenerative window during post-natal life (green).

FIGS. 9A-H show that Erbb2-cKO mice display enlarged heart with compensatory hypertrophy. (FIG. 9A) Western Blot analysis of ErbB2 protein levels in P0 ctrl and Erbb2-cKO heart lysates; (FIG. 9B) Pictures of P0 ctrl and Erbb2-cKO hearts obtained by binocular microscope (LV, left ventricle; RV, right ventricle, LA, left atrium, RA, right atrium); scale bar 1 mm; (FIG. 9C) Heart weight to body weight ratio in P0 ctrl and Erbb2-cKO mice (n=22 mice); (FIG. 9D) Picture of P0 ctrl and Erbb2-cKO mice, displaying a pale skin colour prior to death; scale bar 1 cm; (FIG. 9E) Body weight of P0 ctrl and Erbb2-cKO mice (n=51 mice); (FIG. 9F) CM size (area) quantification based on immunofluorescence analysis of cardiac Troponin T (cTnT) of P0 ctrl and Erbb2-cKO cells cultured in vitro for 5 days (n=836 CMs pooled from the analysis of 6 mice); (FIGS. 9G-H) RT-PCR analysis of hypertrophic markers Nppa, Nppb, Acta1 and β/α-MHC in P0 ctrl and Erbb2-cKO heart lysates (n=8 mice in g; n=15 in h). In all panels numerical data are presented as mean+s.e.m; statistical significance was calculated using two-tailed unpaired Student's t-test in c and e-h; results are marked with one asterisk (*) if p<0.05, two () if p<0.01, three (*) if p<0.001 and four (****) if p<0.0001; statistics source data can be found in Table 1.

FIGS. 10A-H show generation and analysis of CM restricted overexpression of a constitutively active Erbb2. (FIG. 10A) Schematic diagram of the cross-breeding to generate CM restricted overexpression of a constitutively active Erbb2 (caErbb2); (FIG. 10B) Kinetics of ErbB2 protein levels in ctrl and neonatal caErbb2 heart lysates following DOX withdrawal according to scheme in FIG. 3A; (FIGS. 10C-E) Pictures of hearts isolated from ctrl and caErbb2 mice; images were obtained by binocular microscope; Scale bar 1 mm; (FIGS. 10F-H) Echocardiographic measurements of cardiac ejection fraction (EF) and fractional shortening (FS) in ctrl and caErbb2 mice (n=14 mice in FIG. 10F; n=14 mice in FIG. 10G; n=20 mice in FIG. 10H). In all panels neonatal, juvenile and adult caErbb2 mice were generated according to the schema in FIGS. 3A-B. Numerical data are presented as mean+s.e.m; statistical significance was calculated using two-tailed unpaired Student's t-test in f-h; results are marked with one asterisk (*) if p<0.05, two () if p<0.01, three (*) if p<0.001 and four (****) if p<0.0001; statistics source data can be found in Table 1.

FIGS. 11A-G show in vivo induction of ErbB2 signalling promotes CM dedifferentiation, proliferation and hypertrophy. (FIG. 11A) CM cross-sectional area evaluation by WGA immunofluorescence analysis of P56 ctrl and adult caErbb2 left ventricular (LV) heart sections (n=306 CMs pooled from the analysis of 6 mice); representative pictures are provided; Scale bar 10 µm; (FIG. 11B) Calculation of CM number in P56 ctrl and adult caErbb2 hearts (n=6 mice); (FIGS. 11C-D) Hematoxilin and Eosin (H&E) histological analysis of LV heart sections in ctrl and caErbb2 mice; Scale bar 25 µm; (FIGS. 11E-F) in vivo CM sarcomeric status evaluation by immunofluorescence analysis of cardiac Troponin T (cTnT) in ctrl and caErbb2 LV heart sections; Images were obtained using a spinning-disk confocal microscope; Scale bar 5 µm (FIG. 11G) WB analysis of cKIT protein levels in P7 ctrl and neonatal caErbb2 heart lysates. In all panels neonatal, juvenile and adult caErbb2 mice were generated according to the schema in FIGS. 3A-B. Numerical data are presented as mean+s.e.m; statistical significance was calculated using two-tailed unpaired Student's t-test in FIGS. 11A-B; results are marked with one asterisk (*) if p<0.05, two () if p<0.01, three (*) if p<0.001 and four (****) if p<0.0001; statistics source data can be found in Table 1.

FIGS. 12A-F show analysis of mediators and modulators of caErbB2-induced CM dedifferentiation, proliferation and hypertrophy. (FIG. 12A) CM sarcomeric status evaluation based on cardiac Troponin T (cTnT) immunofluorescence analysis in P7 ctrl and neonatal caErbb2 heart cells treated in vitro for 2 days with pharmacological inhibitors of ERK and AKT (ERK-i and AKT-i); sarcomeric status was scored according to the criteria presented in FIG. 5C (n=466 CMs pooled from the analysis of 24 samples); (FIG. 12B) in vivo immunofluorescence analysis of β-Catenin and sarcomeric Troponin T (cTnT) in LV heart sections of P7 ctrl and neonatal caErbb2 mice; images were obtained using a spinning-disk confocal microscope; Scale bar 10 µm (FIG. 12C) in vitro immunofluorescence analysis of β-Catenin and Troponin T (cTnT) in P7 neonatal caErbb2 heart cells treated with pharmacological inhibitors of GSK3β or β-Catenin (GSK3β-i and β-Catenin-i); Scale bar 60 µm; (FIGS. 12D-F) P7 ctrl and neonatal caErbb2 heart cells were treated with p38 inhibitor (p38-i), FGF1 or Periostin in vitro for 2 days; CM were identified by Troponin T (cTnT) staining and analysed for (FIG. 12D) cell-cycle re-entry (Ki67), (FIG. 12E) dedifferentiation marker RUNX1 and (FIG. 12F) size by immunofluorescence analysis (n=6013 CMs pooled from the analysis of 48 samples in FIG. 12D; n=4217 CMs pooled from the analysis of 43 samples in FIG. 12E; n=484 CMs pooled from the analysis of 17 samples in FIG. 12F). In all panels numerical data are presented as mean+s.e.m; statistical significance was calculated using one-way ANOVA followed by Tukey's test in FIG. 12A and FIGS. 12D-F; results are marked with one asterisk (*) if p<0.05, two () if p<0.01, three (*) if p<0.001 and four (****) if p<0.0001; Statistics source data can be found in Table 1.

FIGS. 13A-B show that transient caErbb2 induces transient CM dedifferentiation and neovascularization following heart injury. (FIG. 13A) Hematoxylin and eosin (H&E) histological analysis of remote zone of LV heart sections of ctrl and adult transient caErbb2 mice ~1-month-post-MI (~P70) and ~2-months-post-MI (~P98, ~one-month after caErbb2 signal termination) following myocardial infarction at ~P42 according to the schema in FIG. 7B; Scale bar 50 µm; (FIG. 13B) Angiogenesis evaluation by immunofluorescence analysis of CD34 in heart sections of ~3-weeks-post-MI (~P63) ctrl and adult caErbb2 following myocardial infarction at ~P42 according to the scheme in FIG. 7B; heart sections were co-stained with antibodies to cardiac Troponin T (cTnT) for identification of CMs (n=50 fields pooled form the analysis of 6 mice); numerical data are presented as mean+s.e.m; statistical significance was calculated using two-tailed unpaired Student's t-test; results are marked with one asterisk (*) if p<0.05; Representative pictures are provided; Scale bar 30 µm. statistics source data can be found in Table 1.

DESCRIPTION OF SPECIFIC EMBODIMENTS OF THE INVENTION

The present invention, in some embodiments thereof, relates to methods, kits and devices for promoting cardiac regeneration.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The murine heart loses its regenerative potential within the first week of postnatal life, which coincides with cardiomyocyte (CM) terminal differentiation and cell cycle withdrawal. The NRG1/ErbB4/ErbB2 signaling pathway plays an essential role during heart development and improves heart function following ischemic injury.

Whilst conceiving the present invention, the inventors have realized that upregulating the ErbB-2 pathway may be used in order to drive CM dedifferentiation and proliferation.

Whilst reducing the present invention to practice, the present inventors have explored, using loss- and gain-of-function genetic tools, the role of the NRG1 co-receptor ErbB2 in cardiac regeneration.

As is illustrated herein below and in the Examples section which follows, NRG1-induced CM proliferation diminished one week after birth owing to a reduction in ErbB2 expression. CM-specific Erbb2 knockout revealed that ErbB2 is required for CM proliferation at embryonic/neonatal stages. Induction of a constitutively active ErbB2 (caErbB2) in neonatal, juvenile and adult CMs resulted in cardiomegaly, characterized by extensive CM hypertrophy, dedifferentiation and proliferation, differentially mediated by ERK, AKT and GSK3β/β-catenin signaling pathways. Transient induction of caErbB2 following myocardial infarction triggered CM dedifferentiation and proliferation followed by redifferentiation and regeneration.

Thus, ErbB-2 activity or expression is both necessary for CM proliferation and sufficient to reactivate postnatal CM proliferative and regenerative potentials.

Thus, according to an aspect of the invention there is provided a method of potentiating cardiac regeneration with neuregulin treatment in a subject in need thereof, the method comprising administering to the subject a therapeutic effective amount of an agent which upregulates activity or expression of ErbB-2, thereby potentiating cardiac regeneration with neuregulin treatment.

According to an additional or an alternative embodiment, there is provide a method of regenerating a cardiac tissue in a subject in need thereof, the method comprising administering to the subject a therapeutic effective amount of an agent which upregulates activity or expression of ErbB-2, wherein the agent is not neuregulin, thereby regenerating the cardiac tissue.

As used herein the phrase "cardiac regeneration" refers to the ability to trigger regeneration of heart muscle e.g., in a pathologic state (traumatic, chronic or acute). In other words, cardiac regeneration much depends on the induction of proliferation of cardiomyocytes.

As used herein "a cardiomyocyte" or "cardiomyocytes" (abbreviated as, CM, CMs, respectively), also known as myocardiocytes or cardiac myocytes, are the muscle cells (myocytes) that make up the cardiac muscle. The term refers to cardiomyocytes of any species including mammalian, e.g., human at any stage of development. According to a specific embodiment, the cardiomyocyte is a neonatal CM (e.g., for human up 6 months after birth). According to a specific embodiment, the cardiomyocyte is an adult cardiomyocyte (e.g., for human at least 16-18 years after birth).

Thus, according to a specific embodiment, the cardiomyocytes are of a subject having a heart disease.

According to a specific embodiment, the cardiomyocytes are of a donor healthy subject.

According to a specific embodiment, the cardiomyocytes may be naturally occurring.

According to a specific embodiment, the CMs have been ex-vivo differentiated into cardiomyocytes (e.g., from pluripotent stem cells e.g., embryonic stem cells (hESCs) and induced pluripotent stem cells (iPSCs)). Methods of differentiating stem cells into CMs are well known in the art. For example, an iPSC can be co-cultured with visceral endoderm-like cells (see, e.g., Mummery et al. (2003) Circulation 107:2733). An iPS cell can also be induced to undergo cardiomyogenesis without co-culture with a feeder cell or other cell. For example, as described in U.S. Pat. No. 7,297,539. The CMs may be fully differentiated when contacted with the agent. According to another embodiment, the cells are committed to the cardiac lineage and the agent is added to the culture during or following the differentiation process.

According to a specific embodiment, the cardiomyocytes are human CMs.

According to a specific embodiment, the CMs are a cell-line.

According to a specific embodiment, the CMs are primary CMs.

As used herein the term "inducing proliferation" refers to an increase in CM proliferation which is statistically significant (as compared to untreated cells of the same origin and developmental stage) and is a result of contacting the cardiomyocytes with the agent.

As used herein the term "potentiating" refers to increasing the effect of a drug (e.g., neuregulin) as compared to its effect when administered alone.

As used herein the term "ErbB-2" or "ErbB2" or "erbb-2" or "HER2" (P04626) refers to the expression product (RNA or protein) of the ERBB2 gene, which is also frequently called HER2 (from human epidermal growth factor receptor 2) or HER2/neu.

HER2 is a member of the human epidermal growth factor receptor (HER/EGFR/ErbB) family. Amplification or overexpression of this oncogene has been shown to play an important role in the development and progression of certain aggressive types of breast cancer.

The ErbB-2 protein of the invention may be wild-type ErbB-2, or constitutively active ErbB-2, though for therapeutic goals the first is preferred. Also contemplated are functional homologues of the protein that maintain its function in CM proliferation. Suitable conservative substitutions of amino acids are known to those of skill in the art and may be made generally without altering the biological activity of the resulting molecule. Those of skill in this art recognize that, in general, single amino acid substitutions in non-essential regions of a polypeptide do not substantially alter biological activity (see, e.g., Watson et al., Molecular Biology of the Gene, 4.sup.th Edition, 1987, The Bejacmin/Cummings Pub. co., p. 224).

As used herein the term "neuregulin" (PF02158) refers to a member of a family of structurally related proteins that are part of the EGF family of proteins. These proteins have been shown to have diverse functions in the development of the nervous system and play multiple essential roles in vertebrate embryogenesis including: cardiac development, Schwann cell and oligodendrocyte differentiation, some aspects of neuronal development, as well as the formation of neuromuscular synapses [Yarden Y, Burden S (1997). "Neuregulins and their receptors: a versatile signaling module in organogenesis and oncogenesis". Neuron 18 (6): 847-55].

Multiple family members are generated by alternate splicing or by use of several cell type-specific transcription initiation sites. In general, they bind to and activate the erbB family of receptor tyrosine kinases (ErbB-2 (HER2), ErbB-3 (HER3), and ErbB-4 (HER4)), functioning both as heterodimers and homodimers.

According to a specific embodiment, the neuregulin is selected from the group consisting of:

Neuregulin-1 (NRG1), with numerous discovered isoforms stemming from alternative splicing: Type I NRG1; alternative names: Heregulin, NEU differentiation factor (NDF), or acetylcholine receptor inducing activity (ARIA); Type II NRG1; alternative name: Glial Growth Factor-2 (GGF2); Type III NRG1; alternative name: Sensory and motor neuron-derived factor (SMDF); Type IV NRG1; Type V NRG1; Type VI NRG1; Types IV-VI are proteins with 3 novel N-terminal domains.

Neuregulin-2 (NRG2);
Neuregulin-3 (NRG3); and
Neuregulin-4 (NRG4).

Thus according to an embodiment of the invention, the neuregulin can bind and activate ErbB-2 (as part of a heterodimer with ErbB-3, ErbB-4) to induce CM proliferation, including but not limited to all neuregulin isoforms, neuregulin EGF domain alone, polypeptides comprising neuregulin EGF-like domain, neuregulin mutants or derivatives, and any kind of neuregulin-like gene expression products that also activate erbb-2. Neuregulin also includes NRG-1, NRG-2, NRG-3 and NRG-4 proteins, peptides, fragments and compounds that mimic the activities of neuregulin including nucleic acid sequences encoding same.

Neuregulin also includes those variants with conservative amino acid substitutions that do not substantially alter their biological activity (i.e., binding erbb-2 and induce proliferation of CMs). Suitable conservative substitutions of amino acids are known to those of skill in the art and may be made generally without altering the biological activity of the resulting molecule. Those of skill in this art recognize that, in general, single amino acid substitutions in non-essential regions of a polypeptide do not substantially alter biological activity (see, e.g., Watson et al., Molecular Biology of the Gene, 4.sup.th Edition, 1987, The Bejacmin/Cummings Pub. co., p. 224).

As used herein, "epidermal growth factor-like domain" or "EGF-like domain" refers to a polypeptide motif encoded by the neuregulin gene that binds to and activates ErbB-2, ErbB3, ErbB4, or combinations thereof, and bears a structural similarity to the EGF receptor-binding domain as disclosed in WO 00/64400, Holmes et al., Science, 256: 1205-1210 (1992); U.S. Pat. Nos. 5,530,109 and 5,716,930; Hijazi et al., Int. J. Oncol., 13:1061-1067 (1998); Chang et al., Nature, 387:509-512 (1997); Carraway et al., Nature, 387:512-516 (1997); Higashiyama et al., J. Biochem., 122: 675-680 (1997); and WO 97/09425, the contents of which are all incorporated herein by reference. In certain embodiments, EGF-like domain binds to and activates ErbB-2/ErbB4 or ErbB-2/ErbB3 heterodimers. In certain embodiments, EGF-like domain comprises the amino acid sequence of the receptor binding domain of NRG-1. In some embodiments, EGF-like domain comprises the amino acid sequence corresponding to amino acid residues 177-226, 177-237, or 177-240 of NRG-1. In certain embodiments, EGF-like domain comprises the amino acid sequence of the receptor binding domain of NRG-2. In certain embodiments, EGF-like domain comprises the amino acid sequence of the receptor binding domain of NRG-3. In certain embodiments, EGF-like domain comprises the amino acid sequence of the receptor binding domain of NRG-4. In certain embodiments, EGF-like domain comprises the amino acid sequence of Ala Glu Lys Glu Lys Thr Phe Cys Val Asn Gly Gly Glu Cys Phe Met Val Lys Asp Leu Ser Asn Pro (SEQ ID NO: 1), as described in U.S. Pat. No. 5,834,229. In a specific embodiment, neuregulin used in the present invention binds to and activates ErbB-2/ErbB4 or ErbB-2/ErbB3 heterodimers, for example, but not for the purpose of restriction, peptides including the 177-237 residues of NRG-1 β2 isoform containing the amino acid sequence:

```
                                          (SEQ ID NO: 2)
SHLVKCAEKEKTFCVNGGECFMVKDLSNPSRYLCKC
PNEFTGDRCQNYVMASFYKAEELYQ.
```

According to a specific embodiment, the neuregulin is human NRG1 e.g., NP_001153467.

According to a specific embodiment, the neuregulin is commercially available.

According to a specific embodiment, the neuregulin is human neuregulin.

According to a specific embodiment, the neuregulin is soluble neuregulin.

According to a specific embodiment, the neuregulin is NRG1 (e.g., NRG-b1).

As used herein neuregulin refers to polynucleotide expressing neuregulin or neuregulin protein, which may be naturally occurring (purified from cells naturally expressing same) or synthetic e.g., recombinantly produced (e.g., soluble portion of the neuregulin protein with or without nucleic acid/backbone modifications) or produced by peptide synthesis means e.g., solid-phase.

According to a specific embodiment, the neuregulin is an RNA e.g., modified RNA (mod-RNA), the technology details of which are described hereinbelow. SEQ ID NOs: 3 and 4 for ErbB-2 and neuregulin MOD_RNA, respectively, Briefly, mod-RNAs are changed in the G-Cap at the 5' to improve translation efficiency, and further comprise a ligation of 5'UTR containing a strong Kozak to improve translation initiation and alpha globin 3'UTR, to ensure mRNA stability. These procedures are described in Warren, L. et al, 2010 Cell stem cells, 5; 7(5):618-30.

As used herein, the term "agent" refers to a substance which can be of a biological nature e.g., proteinacious substance e.g., polypeptide/peptide or an antibody, nucleic acid molecule e.g., a polynucleotide or an oligonucleotide, or a chemical e.g., small molecule.

Upregulation of ErbB-2 can be effected at the activity or expression level of same at the genomic level, at the transcript level or at the protein level.

The upregulation can be effected by upregulation of ErbB-2 per se, or upregulating an activator of ErbB-2 (e.g., neuregulin, e.g., as described above), upregulating a downstream effector of ErbB-2, or down-regulating a negative regulator of ErbB-2.

As used herein the term "polynucleotide" refers to a single or double stranded nucleic acid sequence which is isolated and provided in the form of an RNA sequence, a complementary polynucleotide sequence (cDNA), a genomic polynucleotide sequence, a synthetically modified DNA or RNA and/or a composite polynucleotide sequences (e.g., a combination of the above).

The term "isolated" refers to at least partially separated from the natural environment e.g., from a recombinant host cell.

According to a specific embodiment, the agent which upregulates activity or expression of ErbB-2 is an ErbB-2 activating antibody.

As used herein "an activating antibody" or "an agonistic antibody", which may be interchangeably used herein, refers to an antibody or an antibody fragment which binds to ErbB-2 and activates proliferative signaling therefrom, causing CM proliferation.

Methods of selecting such antibodies are well known in the art. Selection methods include, but are not limited to monitoring CM proliferation, binding assays, and signaling assays.

A non-limiting example of an ErbB-2 activating antibody includes, but is not limited to, that described in Fukazawa et al. J Mol Cell Cardiol. 2003 December; 35(12):1473-9.

According to a specific embodiment, an agent which upregulates activity or expression of ErbB-2 activates a signaling effector downstream of the ErbB-2.

According to a specific embodiment, the signaling effector is selected from the group consisting of Erk and Akt.

The activation of signal transduction pathways by growth factors, hormones and neurotransmitters is mediated through two closely related MAP kinases, p44 and p42, designated extracellular-signal related kinase 1 (ERK 1) and ERK 2, respectively. Biochemicals that activate ERK have many applications in biochemical and physiological research and are well known in the art. Examples include, but are not limited to, ceramaide C6, Fisetin, Resveratrol, Isoproterenol Hydrochloride and KU-0058948.

The serine/threonine kinase Akt family contains several members, including Akt1 (also designated PKB or RacPK), Akt2 (also designated PKBβ or RacPK-β) and Akt 3 (also designated $PKB_1$ or thyoma viral proto-oncogene 3). Akt1 and Akt2 are activated by PDGF stimulation. The activation of Akt1 and Akt2 is inhibited by the PI kinase inhibitor Wortmannin, suggesting that the protein signals downstream of the PI kinases. A non-limiting example of Akt activator is SC79 (available commercially), As mentioned, the upregulation of ErbB-2 activity or expression can also be effected by activators of ErbB-2.

According to a specific embodiment the agent is neuregulin (as described hereinabove).

According to another embodiment (or an additional embodiment), the activator of ErbB-2 is selected from the group consisting of FGF1 and periostin.

As used herein "periostin" (POSTN, PN, or osteoblast-specific factor OSF-2, e.g., Q15063 (POSTN_HUMAN)) is a protein that in humans is encoded by the POSTN gene. Periostin functions as a ligand for alpha-V/beta-3 and alpha-V/beta-5 integrins to support adhesion and migration of epithelial cells. Periostin is a gla domain vitamin K dependent factor. Periostin also includes those variants with conservative amino acid substitutions that do not substantially alter their biological activity (i.e., induce proliferation of CMs). Suitable conservative substitutions of amino acids are known to those of skill in the art and may be made generally without altering the biological activity of the resulting molecule. Those of skill in this art recognize that, in general, single amino acid substitutions in non-essential regions of a polypeptide do not substantially alter biological activity (see, e.g., Watson et al., Molecular Biology of the Gene, 4.sup.th Edition, 1987, The Bejacmin/Cummings Pub. co., p. 224).

As used herein "FGF-1" or "fibroblast growth factor-1" or "Heparin-binding growth factor 1" or "acidic fibroblast growth factor-1" (P05230) refers to the RNA or protein that in humans is encoded by the FGF1 gene. The protein encoded by this gene is a member of the fibroblast growth factor (FGF) family. This protein functions as a modifier of endothelial cell migration and proliferation, as well as an angiogenic factor. It acts as a mitogen for a variety of mesoderm- and neuroectoderm-derived cells in vitro, thus is thought to be involved in organogenesis. Three alternatively spliced variants encoding different isoforms have been described. FGF-1 also includes those variants with conservative amino acid substitutions that do not substantially alter their biological activity (i.e., induce proliferation of CMs). Suitable conservative substitutions of amino acids are known to those of skill in the art and may be made generally without altering the biological activity of the resulting molecule. Those of skill in this art recognize that, in general, single amino acid substitutions in non-essential regions of a polypeptide do not substantially alter biological activity (see, e.g., Watson et al., Molecular Biology of the Gene, 4.sup.th Edition, 1987, The Bejacmin/Cummings Pub. co., p. 224).

According to another embodiment, the agent down-regulates a negative regulator of ErbB-2, e.g., a signaling molecule downstream of said ErbB-2.

According to a specific embodiment, the signaling molecule is selected from the group consisting of GSK3β and p38.

Glycogen synthase kinase 3 beta, also known as GSK3B (P49841), is an enzyme that in humans is encoded by the GSK3B gene. Glycogen synthase kinase-3 (GSK-3) is a proline-directed serine-threonine kinase that was initially identified as a phosphorylating and an inactivating agent of glycogen synthase. Two isoforms, alpha (GSK3A) and beta, show a high degree of amino acid homology. GSK3B is involved in energy metabolism, neuronal cell development, and body pattern formation.[1]

Examples of GSK3B inhibitors include, but are not limited to, valproic acid, Chir 99021, BIO(6-bromoindirubin-3'-oxime), IM-12.

P38 mitogen-activated protein kinases (e.g., 015264) are a class of mitogen-activated protein kinases that are responsive to stress stimuli, such as cytokines, ultraviolet irradiation, heat shock, and osmotic shock, and are involved in cell differentiation, apoptosis and autophagy.

p38 MAP Kinase (MAPK), also called RK or CSBP (Cytokinin Specific Binding Protein), is the mammalian orthologue of the yeast Hog1p MAP kinase, which participates in a signaling cascade controlling cellular responses to cytokines and stress.

Four p38 MAP kinases, p38-α (MAPK14), -β (MAPK11), -γ (MAPK12/ERK6), and -δ (MAPK13/SAPK4), have been identified.

Examples of inhibitors of p38 include, but are not limited to, BIRB 796, VX-702, SB 239063, SB202190, SCIO 469, and BMS 582949.

Following is a description of platform technologies that can be used to upregulate or down-regulate targets as described herein.

The term "antibody" as used in this invention includes intact molecules as well as functional fragments thereof (such as Fab, F(ab')2, Fv, scFv, dsFv, or single domain molecules such as VH and VL) that are capable of binding to an epitope of an antigen. It will be appreciated that the antibody can be an activating antoibody e.g., in the case of ErbB-2, or an inhibitory antibody (intracellular) in the case of GSK3B or p38. Selection of activating antibodies or inhibitory antibodies are well known in the art. Some are described hereinabove and generally assay the activity of the antibodies on the target or a downstream proxy of same.

Suitable antibody fragments for practicing some embodiments of the invention include a complementarity-determining region (CDR) of an immunoglobulin light chain (referred to herein as "light chain"), a complementarity-determining region of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single chain Fv Fv (scFv), a disulfide-stabilized Fv (dsFv), an Fab, an Fab', and an F(ab')2.

As used herein, the terms "complementarity-determining region" or "CDR" are used interchangeably to refer to the antigen binding regions found within the variable region of the heavy and light chain polypeptides. Generally, antibodies comprise three CDRs in each of the VH (CDR HI or HI; CDR H2 or H2; and CDR H3 or H3) and three in each of the VL (CDR LI or LI; CDR L2 or L2; and CDR L3 or L3).

The identity of the amino acid residues in a particular antibody that make up a variable region or a CDR can be determined using methods well known in the art and include methods such as sequence variability as defined by Kabat et al. (See, e.g., Kabat et al., 1992, Sequences of Proteins of Immunological Interest, 5th ed., Public Health Service, NIH, Washington D.C.), location of the structural loop regions as defined by Chothia et al. (see, e.g., Chothia et al., Nature 342:877-883, 1989.), a compromise between Kabat and Chothia using Oxford Molecular's AbM antibody modeling software (now Accelrys®, see, Martin et al., 1989, Proc. Natl Acad Sci USA. 86:9268; and world wide web site www(dot)bioinf-orgdotuk/abs), available complex crystal structures as defined by the contact definition (see MacCallum et al., J. Mol. Biol. 262:732-745, 1996) and the "conformational definition" (see, e.g., Makabe et al., Journal of Biological Chemistry, 283:1156-1166, 2008).

As used herein, the "variable regions" and "CDRs" may refer to variable regions and CDRs defined by any approach known in the art, including combinations of approaches.

Functional antibody fragments comprising whole or essentially whole variable regions of both light and heavy chains are defined as follows:

(i) Fv, defined as a genetically engineered fragment consisting of the variable region of the light chain (VL) and the variable region of the heavy chain (VH) expressed as two chains;

(ii) single chain Fv ("scFv"), a genetically engineered single chain molecule including the variable region of the light chain and the variable region of the heavy chain, linked by a suitable polypeptide linker as a genetically fused single chain molecule.

(iii) disulfide-stabilized Fv ("dsFv"), a genetically engineered antibody including the variable region of the light chain and the variable region of the heavy chain, linked by a genetically engineered disulfide bond.

(iv) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and CH1 domains thereof;

(v) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule);

(vi) F(ab') 2, a fragment of an antibody molecule containing a monovalent antigen-binding portion of an antibody molecule which can be obtained by treating whole antibody with the enzyme pepsin (i.e., a dimer of Fab' fragments held together by two disulfide bonds); and (vii) Single domain antibodies or nanobodies are composed of a single VH or VL domains which exhibit sufficient affinity to the antigen.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to some embodiments of the invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Following is a list of agents capable of upregulating the expression level and/or activity of targets of interest e.g., ErbB-2, Erk, Akt, FGF-1, neuregulin, periostin or a combination of same.

An agent capable of upregulating expression of the target may be an exogenous polynucleotide sequence designed and constructed to express at least a functional portion of the target. Accordingly, the exogenous polynucleotide sequence may be a DNA or RNA sequence encoding the target molecule, capable of inducing CM proliferation.

The phrase "functional portion" as used herein refers to part of the target protein (i.e., a polypeptide) which exhibits functional properties of the enzyme such as binding to a substrate. According to preferred embodiments of some embodiments of the invention the functional portion of the target is a polypeptide sequence e.g., EGF-domain of naeuregulin.

To express an exogenous target in mammalian cells, a polynucleotide sequence encoding the target is preferably ligated into a nucleic acid construct suitable for mammalian cell expression. Such a nucleic acid construct includes a promoter sequence for directing transcription of the polynucleotide sequence in the cell in a constitutive or inducible manner.

It will be appreciated that the nucleic acid construct of some embodiments of the invention can also utilize homologues which exhibit the desired activity (i.e., CM proliferation). Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the naturally occurring target, as determined using the BestFit software of the Wisconsin sequence analysis package, utilizing the Smith and Waterman algorithm, where gap weight equals 50, length weight equals 3, average match equals 10 and average mismatch equals −9.

Constitutive promoters suitable for use with some embodiments of the invention are promoter sequences which are active under most environmental conditions and most types of cells such as the cytomegalovirus (CMV) and Rous sarcoma virus (RSV). Inducible promoters suitable for use with some embodiments of the invention include for example the tetracycline-inducible promoter (Zabala M, et al., Cancer Res. 2004, 64(8): 2799-804).

An agent capable of upregulating the target may also be any compound which is capable of increasing the transcription and/or translation of an endogenous DNA or mRNA encoding the target and thus increasing endogenous activity.

An agent capable of upregulating a target may also be an exogenous polypeptide including at least a functional portion (as described hereinabove) of the target e.g., as described in details for neuregulin above.

An agent which upregulates a target can also be a modified RNA (modRNA). These have been proven successful in cardiac therapy. See for instance Chien et al. 2014 Oct. 9; 5(1):a014035. Recently, it has been reported that synthetic, modified RNA (herein referred to as "MOD-RNA" or "modRNA") can be used for over-expression of a gene of interest in mammalian cells in vitro/vivo. The chemical and sequence modifications made in the synthetic mRNA stabilize the molecule and enhance transcription. Expression of polypeptides from MOD-RNA allows for highly efficient, transient expression of a gene of interest in vitro without requiring introduction of DNA or viral sequences that may be integrated into the host cell. Use of MOD-RNAs to express a protein in vivo occurs rapidly, and is much more efficient and less toxic to cells than introducing non-MOD RNAs (e.g., normal RNA sequences), or direct intracellular introduction of proteins, which can activate the innate immune system. According to a specific embodiment the mod-RNA comprises a 5' cap or a 5' cap analog and/or does not comprise a 5' triphosphate. According to a specific embodiment the mod-RNA molecule further comprises a poly(A) tail, a Kozak sequence, a 3' untranslated region, a 5' untranslated region, or any combination thereof, and wherein the poly(A) tail, Kozak sequence, 3' untranslated region, 5' untranslated region can optionally comprise one or modified nucleosides selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2' deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m-2,7G), N2,N2,7-trimethylguanosine (m-2,2,7G), and inosine (I).

According to a specific embodiment, the MOD-RNA comprises at least two nucleosides in the coding sequence. These modified nucleosides may be selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Urn), 2' deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m-2,7G)

and N2,N2,7-trimethylguanosine (m-2,2,7G), and inosine. More details to the use of modRNA can be found in U.S. Patent Application 20140073687, which is hereby incorporated by reference in its entirety.

It will be appreciated that genome editing technology (e.g., CRISPR-Cas9) can also be used to upregulate expression of a target of interest (e.g., introducing mutations which increase the activity of the endogenous genes or introducing an additional copy of the gene or a homologue thereof so as to cause over-expression). Such genome editing technologies are described in details hereinbelow.

As used herein the phrase "downregulates expression" refers to downregulating the expression of a protein (e.g. p38. GSK3B) at the genomic (e.g. homologous recombination and site specific endonucleases) and/or the transcript level using a variety of molecules which interfere with transcription and/or translation (e.g., RNA silencing agents) or on the protein level (e.g., aptamers, small molecules and inhibitory peptides, antagonists, enzymes that cleave the polypeptide, antibodies and the like).

For the same culture conditions the expression is generally expressed in comparison to the expression in a cell of the same species but not contacted with the agent or contacted with a vehicle control, also referred to as control.

Down regulation of expression may be either transient or permanent.

According to specific embodiments, down regulating expression refers to the absence of mRNA and/or protein, as detected by RT-PCR or Western blot, respectively.

According to other specific embodiments down regulating expression refers to a decrease in the level of mRNA and/or protein, as detected by RT-PCR or Western blot, respectively. The reduction may be by at least a 10%, at least 20%, at least 30%, at least 40%, at least 50%, at least 60%, at least 70%, at least 80%, at least 90%, at least 95% or at least 99% reduction.

Non-limiting examples of agents capable of down regulating target expression are described in details hereinbelow.

Down-Regulation at the Nucleic Acid Level

Down-regulation at the nucleic acid level is typically effected using a nucleic acid agent, having a nucleic acid backbone, DNA, RNA, mimetics thereof or a combination of same. The nucleic acid agent may be encoded from a DNA molecule or provided to the cell per se.

Thus, downregulation of a target can be achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g., the full translation and/or expression) of an mRNA molecule through a post-transcriptional silencing mechanism. RNA silencing agents include non-coding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs.

In one embodiment, the RNA silencing agent is capable of inducing RNA interference.

In another embodiment, the RNA silencing agent is capable of mediating translational repression.

According to an embodiment of the invention, the RNA silencing agent is specific to the target RNA (e.g., p38, GSK3B) and does not cross inhibit or silence other targets or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene; as determined by PCR, Western blot, Immunohistochemistry and/or flow cytometry.

RNA interference refers to the process of sequence-specific post-transcriptional gene silencing in animals mediated by short interfering RNAs (siRNAs).

Following is a detailed description on RNA silencing agents that can be used according to specific embodiments of the present invention.

DsRNA, siRNA and shRNA—

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplate use of dsRNA to downregulate protein expression from mRNA.

According to one embodiment dsRNA longer than 30 bp are used. Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

According to some embodiments of the invention, dsRNA is provided in cells where the interferon pathway is not activated, see for example Billy et al., PNAS 2001, Vol 98, pages 14428-14433. and Diallo et al, Oligonucleotides, Oct. 1, 2003, 13(5): 381-392. doi: 10.1089/154545703322617069.

According to an embodiment of the invention, the long dsRNA are specifically designed not to induce the interferon and PKR pathways for down-regulating gene expression. For example, Shinagwa and Ishii [Genes & Dev. 17 (11): 1340-1345, 2003] have developed a vector, named pDE-CAP, to express long double-strand RNA from an RNA polymerase II (Pol II) promoter. Because the transcripts from pDECAP lack both the 5'-cap structure and the 3'-poly (A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 base pairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is suggested to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned, the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-CAAGAGA-3' and 5'-UUACAA-3' (International Patent Application Nos. WO2013126963 and WO2014107763). It will be recognized by one of skill in the art that the resulting single chain oligonucleotide forms a stem-loop or hairpin structure comprising a double-stranded region capable of interacting with the RNAi machinery.

Synthesis of RNA silencing agents suitable for use with some embodiments of the invention can be effected as follows. First, the target mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl Chem Biochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www(dot)ambion(dot)com/techlib/tn/91/912(dot)html).

Second, potential target sites are compared to an appropriate genomic database (e.g., human, mouse, rat etc.) using any sequence alignment software, such as the BLAST software available from the NCBI server (www(dot)ncbi (dot)nlm(dot)nih(dot)gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

It will be appreciated that, and as mentioned hereinabove, the RNA silencing agent of some embodiments of the invention need not be limited to those molecules containing only RNA, but further encompasses chemically-modified nucleotides and non-nucleotides.

miRNA and miRNA Mimics—

According to another embodiment the RNA silencing agent may be a miRNA.

The term "microRNA", "miRNA", and "miR" are synonymous and refer to a collection of non-coding single-stranded RNA molecules of about 19-28 nucleotides in length, which regulate gene expression. miRNAs are found in a wide range of organisms (viruses(dot)fwdarw(dot) humans) and have been shown to play a role in development, homeostasis, and disease etiology.

Antisense—

Antisense is a single stranded RNA designed to prevent or inhibit expression of a gene by specifically hybridizing to its mRNA. Downregulation of a target can be effected using an antisense polynucleotide capable of specifically hybridizing with an mRNA transcript encoding the target.

Design of antisense molecules which can be used to efficiently downregulate a target must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Jääskelainen et al. Cell Mol Biol Lett. (2002) 7(2):236-7; Gait, Cell Mol Life Sci. (2003) 60(5):844-53; Martino et al. J Biomed Biotechnol. (2009) 2009:410260; Grijalvo et al. Expert Opin Ther Pat. (2014) 24(7):801-19; Falzarano et al, Nucleic Acid Ther. (2014) 24(1):87-100; Shilakari et al. Biomed Res Int. (2014) 2014: 526391; Prakash et al. Nucleic Acids Res. (2014) 42(13):8796-807 and Asselin et al. J Gene Med. (2014) 16(7-8):157-65]

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells.

Nucleic acid agents can also operate at the DNA level as summarized infra.

Downregulation of a target of interest can also be achieved by inactivating the gene (e.g., p38, GSK3B) via introducing targeted mutations involving loss-of function alterations (e.g. point mutations, deletions and insertions) in the gene structure.

As used herein, the phrase "loss-of-function alterations" refers to any mutation in the DNA sequence of a gene which results in downregulation of the expression level and/or activity of the expressed product, i.e., the mRNA transcript and/or the translated protein. Non-limiting examples of such loss-of-function alterations include a missense mutation, i.e., a mutation which changes an amino acid residue in the protein with another amino acid residue and thereby abolishes the enzymatic activity of the protein; a nonsense mutation, i.e., a mutation which introduces a stop codon in a protein, e.g., an early stop codon which results in a shorter protein devoid of the enzymatic activity; a frame-shift mutation, i.e., a mutation, usually, deletion or insertion of nucleic acid(s) which changes the reading frame of the protein, and may result in an early termination by introducing a stop codon into a reading frame (e.g., a truncated protein, devoid of the enzymatic activity), or in a longer amino acid sequence (e.g., a readthrough protein) which affects the secondary or tertiary structure of the protein and results in a non-functional protein, devoid of the enzymatic activity of the non-mutated polypeptide; a readthrough mutation due to a frame-shift mutation or a modified stop codon mutation (i.e., when the stop codon is mutated into an amino acid codon), with an abolished enzymatic activity; a promoter mutation, i.e., a mutation in a promoter sequence, usually 5' to the transcription start site of a gene, which results in down-regulation of a specific gene product; a regulatory mutation, i.e., a mutation in a region upstream or downstream, or within a gene, which affects the expression of the gene product; a deletion mutation, i.e., a mutation which deletes coding nucleic acids in a gene sequence and which may result in a frame-shift mutation or an in-frame mutation (within the coding sequence, deletion of one or more amino acid codons); an insertion mutation, i.e., a mutation which inserts coding or non-coding nucleic acids into a gene sequence, and which may result in a frame-shift mutation or an in-frame insertion of one or more amino acid codons; an inversion, i.e., a mutation which results in an inverted coding or non-coding sequence; a splice mutation i.e., a mutation which results in abnormal splicing or poor splicing; and a duplication mutation, i.e., a mutation which results in a duplicated coding or non-coding sequence, which can be in-frame or can cause a frame-shift.

According to specific embodiments loss-of-function alteration of a gene may comprise at least one allele of the gene.

The term "allele" as used herein, refers to any of one or more alternative forms of a gene locus, all of which alleles relate to a trait or characteristic. In a diploid cell or organism, the two alleles of a given gene occupy corresponding loci on a pair of homologous chromosomes.

Methods of introducing nucleic acid alterations to a gene of interest are well known in the art [see for example Menke D. Genesis (2013) 51:-618; Capecchi, Science (1989) 244: 1288-1292; Santiago et al. Proc Natl Acad Sci USA (2008) 105:5809-5814; International Patent Application Nos. WO 2014085593, WO 2009071334 and WO 2011146121; U.S. Pat. Nos. 8,771,945, 8,586,526, 6,774,279 and UP Patent Application Publication Nos. 20030232410, 20050026157, US20060014264; the contents of which are incorporated by reference in their entireties] and include targeted homologous recombination, site specific recombinases, PB transposases and genome editing by engineered nucleases. Agents for introducing nucleic acid alterations to a gene of interest can be designed publically available sources or obtained commercially from Transposagen, Addgene and Sangamo Biosciences.

Following is a description of various exemplary methods used to introduce nucleic acid alterations to a gene of interest and agents for implementing same that can be used according to specific embodiments of the present invention.

Genome Editing using engineered endonucleases—this approach refers to a reverse genetics method using artificially engineered nucleases to cut and create specific double-stranded breaks at a desired location(s) in the genome, which are then repaired by cellular endogenous processes such as, homology directed repair (HDR) and non-homologous end-joining (NHEJ). NHEJ directly joins the DNA ends in a double-stranded break, while HDR utilizes a homologous sequence as a template for regenerating the missing DNA sequence at the break point. In order to introduce specific nucleotide modifications to the genomic DNA, a DNA repair template containing the desired sequence must be present during HDR. Genome editing cannot be performed using traditional restriction endonucleases since most restriction enzymes recognize a few base pairs on the DNA as their target and the probability is very high that the recognized base pair combination will be found in many locations across the genome resulting in multiple cuts not limited to a desired location. To overcome this challenge and create site-specific single- or double-stranded breaks, several distinct classes of nucleases have been discovered and bioengineered to date. These include the meganucleases, Zinc finger nucleases (ZFNs), transcription-activator like effector nucleases (TALENs) and CRISPR/Cas system.

Meganucleases—

Meganucleases are commonly grouped into four families: the LAGLIDADG family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif. The four families of meganucleases are widely separated from one another with respect to conserved structural elements and, consequently, DNA recognition sequence specificity and catalytic activity. Meganucleases are found commonly in microbial species and have the unique property of having very long recognition sequences (>14 bp) thus making them naturally very specific for cutting at a desired location. This can be exploited to make site-specific double-stranded breaks in genome editing. One of skill in the art can use these naturally occurring meganucleases, however the number of such naturally occurring meganucleases is limited. To overcome this challenge, mutagenesis and high throughput screening methods have been used to create meganuclease variants that recognize unique sequences. For example, various meganucleases have been fused to create hybrid enzymes that recognize a new sequence. Alternatively, DNA interacting amino acids of the meganuclease can be altered to design sequence specific meganucleases (see e.g., U.S. Pat. No. 8,021,867). Meganucleases can be designed using the methods described in e.g., Certo, M T et al. Nature Methods (2012) 9:073-975; U.S. Pat. No. 8,304,222; 8,021, 867; 8,119,381; 8,124,369; 8,129,134; 8,133,697; 8,143, 015; 8,143,016; 8,148,098; or 8,163,514, the contents of each are incorporated herein by reference in their entirety. Alternatively, meganucleases with site specific cutting characteristics can be obtained using commercially available technologies e.g., Precision Biosciences' Directed Nuclease Editor™ genome editing technology.

ZFNs and TALENs—

Two distinct classes of engineered nucleases, zinc-finger nucleases (ZFNs) and transcription activator-like effector nucleases (TALENs), have both proven to be effective at producing targeted double-stranded breaks (Christian et al., 2010; Kim et al., 1996; Li et al., 2011; Mahfouz et al., 2011; Miller et al., 2010). Basically, ZFNs and TALENs restriction endonuclease technology utilizes a non-specific DNA cutting enzyme which is linked to a specific DNA binding domain (either a series of zinc finger domains or TALE repeats, respectively). Typically a restriction enzyme whose DNA recognition site and cleaving site are separate from each other is selected. The cleaving portion is separated and then linked to a DNA binding domain, thereby yielding an endonuclease with very high specificity for a desired sequence. An exemplary restriction enzyme with such properties is Fok1. Additionally Fok1 has the advantage of requiring dimerization to have nuclease activity and this means the specificity increases dramatically as each nuclease partner recognizes a unique DNA sequence. To enhance this effect, Fok1 nucleases have been engineered that can only function as heterodimers and have increased catalytic activity. The heterodimer functioning nucleases avoid the possibility of unwanted homodimer activity and thus increase specificity of the double-stranded break.

Thus, for example to target a specific site, ZFNs and TALENs are constructed as nuclease pairs, with each member of the pair designed to bind adjacent sequences at the targeted site. Upon transient expression in cells, the nucleases bind to their target sites and the Fok1 domains heterodimerize to create a double-stranded break. Repair of these double-stranded breaks through the nonhomologous end-joining (NHEJ) pathway most often results in small deletions or small sequence insertions. Since each repair made by NHEJ is unique, the use of a single nuclease pair can produce an allelic series with a range of different deletions at the target site. The deletions typically range anywhere from a few base pairs to a few hundred base pairs in length, but larger deletions have successfully been generated in cell culture by using two pairs of nucleases simultaneously (Carlson et al., 2012; Lee et al., 2010). In addition, when a fragment of DNA with homology to the targeted region is introduced in conjunction with the nuclease pair, the double-stranded break can be repaired via homology directed repair to generate specific modifications (Li et al., 2011; Miller et al., 2010; Urnov et al., 2005).

Although the nuclease portions of both ZFNs and TALENs have similar properties, the difference between these engineered nucleases is in their DNA recognition peptide. ZFNs rely on Cys2-His2 zinc fingers and TALENs on TALEs. Both of these DNA recognizing peptide domains have the characteristic that they are naturally found in combinations in their proteins. Cys2-His2 Zinc fingers typically found in repeats that are 3 bp apart and are found in diverse combinations in a variety of nucleic acid interacting proteins. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others. ZFNs can also be designed and obtained commercially from e.g., Sangamo Biosciences™ (Richmond, Calif.).

Method for designing and obtaining TALENs are described in e.g. Reyon et al. Nature Biotechnology 2012 May; 30(5):460-5; Miller et al. Nat Biotechnol. (2011) 29: 143-148; Cermak et al. Nucleic Acids Research (2011) 39 (12): e82 and Zhang et al. Nature Biotechnology (2011) 29 (2): 149-53. A recently developed web-based program named Mojo Hand was introduced by Mayo Clinic for designing TAL and TALEN constructs for genome editing applications (can be accessed through http://www(dot)talendesign(dot)org). TALEN can also be designed and obtained commercially from e.g., Sangamo Biosciences™ (Richmond, Calif.).

CRISPR-Cas System

Many bacteria and archea contain endogenous RNA-based adaptive immune systems that can degrade nucleic acids of invading phages and plasmids. These systems consist of clustered regularly interspaced short palindromic repeat (CRISPR) genes that produce RNA components and CRISPR associated (Cas) genes that encode protein components. The CRISPR RNAs (crRNAs) contain short stretches of homology to specific viruses and plasmids and act as guides to direct Cas nucleases to degrade the complementary nucleic acids of the corresponding pathogen. Studies of the type II CRISPR/Cas system of *Streptococcus pyogenes* have shown that three components form an RNA/protein complex and together are sufficient for sequence-specific nuclease activity: the Cas9 nuclease, a crRNA containing 20 base pairs of homology to the target sequence, and a trans-activating crRNA (tracrRNA) (Jinek et al. Science (2012) 337: 816-821.). It was further demonstrated that a synthetic chimeric guide RNA (gRNA) composed of a fusion between crRNA and tracrRNA could direct Cas9 to cleave DNA targets that are complementary to the crRNA in vitro. It was also demonstrated that transient expression of Cas9 in conjunction with synthetic gRNAs can be used to produce targeted double-stranded brakes in a variety of different species (Cho et al., 2013; Cong et al., 2013; DiCarlo et al., 2013; Hwang et al., 2013a,b; Jinek et al., 2013; Mali et al., 2013).

The CRIPSR/Cas system for genome editing contains two distinct components: a gRNA and an endonuclease e.g. Cas9.

The gRNA is typically a 20 nucleotide sequence encoding a combination of the target homologous sequence (crRNA) and the endogenous bacterial RNA that links the crRNA to the Cas9 nuclease (tracrRNA) in a single chimeric transcript. The gRNA/Cas9 complex is recruited to the target sequence by the base-pairing between the gRNA sequence and the complement genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the Cas9 can cut both strands of the DNA causing a double-strand break. Just as with ZFNs and TALENs, the double-stranded brakes produced by CRISPR/Cas can undergo homologous recombination or NHEJ.

The Cas9 nuclease has two functional domains: RuvC and HNH, each cutting a different DNA strand. When both of these domains are active, the Cas9 causes double strand breaks in the genomic DNA.

A significant advantage of CRISPR/Cas is that the high efficiency of this system coupled with the ability to easily create synthetic gRNAs enables multiple genes to be targeted simultaneously. In addition, the majority of cells carrying the mutation present biallelic mutations in the targeted genes.

However, apparent flexibility in the base-pairing interactions between the gRNA sequence and the genomic DNA target sequence allows imperfect matches to the target sequence to be cut by Cas9.

Modified versions of the Cas9 enzyme containing a single inactive catalytic domain, either RuvC- or HNH—, are called 'nickases'. With only one active nuclease domain, the Cas9 nickase cuts only one strand of the target DNA, creating a single-strand break or 'nick'. A single-strand break, or nick, is normally quickly repaired through the HDR pathway, using the intact complementary DNA strand as the template. However, two proximal, opposite strand nicks introduced by a Cas9 nickase are treated as a double-strand break, in what is often referred to as a 'double nick' CRISPR system. A double-nick can be repaired by either NHEJ or HDR depending on the desired effect on the gene target. Thus, if specificity and reduced off-target effects are crucial, using the Cas9 nickase to create a double-nick by designing two gRNAs with target sequences in close proximity and on opposite strands of the genomic DNA would decrease off-target effect as either gRNA alone will result in nicks that will not change the genomic DNA.

Modified versions of the Cas9 enzyme containing two inactive catalytic domains (dead Cas9, or dCas9) have no nuclease activity while still able to bind to DNA based on gRNA specificity. The dCas9 can be utilized as a platform for DNA transcriptional regulators to activate or repress gene expression by fusing the inactive enzyme to known regulatory domains. For example, the binding of dCas9 alone to a target sequence in genomic DNA can interfere with gene transcription.

There are a number of publically available tools available to help choose and/or design target sequences as well as lists of bioinformatically determined unique gRNAs for different genes in different species such as the Feng Zhang lab's Target Finder, the Michael Boutros lab's Target Finder (E-CRISP), the RGEN Tools: Cas-OFFinder, the CasFinder: Flexible algorithm for identifying specific Cas9 targets in genomes and the CRISPR Optimal Target Finder.

In order to use the CRISPR system, both gRNA and Cas9 should be expressed in a target cell. The insertion vector can contain both cassettes on a single plasmid or the cassettes are expressed from two separate plasmids. CRISPR plasmids are commercially available such as the px330 plasmid from Addgene.

"Hit and run" or "in-out"—involves a two-step recombination procedure. In the first step, an insertion-type vector containing a dual positive/negative selectable marker cassette is used to introduce the desired sequence alteration. The insertion vector contains a single continuous region of homology to the targeted locus and is modified to carry the mutation of interest. This targeting construct is linearized with a restriction enzyme at a one site within the region of homology, electroporated into the cells, and positive selection is performed to isolate homologous recombinants. These homologous recombinants contain a local duplication that is separated by intervening vector sequence, including the selection cassette. In the second step, targeted clones are subjected to negative selection to identify cells that have lost the selection cassette via intrachromosomal recombination between the duplicated sequences. The local recombination event removes the duplication and, depending on the site of recombination, the allele either retains the introduced mutation or reverts to wild type. The end result is the introduction of the desired modification without the retention of any exogenous sequences.

The "double-replacement" or "tag and exchange" strategy—involves a two-step selection procedure similar to the hit and run approach, but requires the use of two different targeting constructs. In the first step, a standard targeting vector with 3' and 5' homology arms is used to insert a dual positive/negative selectable cassette near the location where the mutation is to be introduced. After electroporation and positive selection, homologously targeted clones are identified. Next, a second targeting vector that contains a region of homology with the desired mutation is electroporated into targeted clones, and negative selection is applied to remove the selection cassette and introduce the mutation. The final allele contains the desired mutation while eliminating unwanted exogenous sequences.

Site-Specific Recombinases—The Cre recombinase derived from the P1 bacteriophage and Flp recombinase derived from the yeast *Saccharomyces cerevisiae* are site-specific DNA recombinases each recognizing a unique 34 base pair DNA sequence (termed "Lox" and "FRT", respectively) and sequences that are flanked with either Lox sites or FRT sites can be readily removed via site-specific recombination upon expression of Cre or Flp recombinase, respectively. For example, the Lox sequence is composed of an asymmetric eight base pair spacer region flanked by 13 base pair inverted repeats. Cre recombines the 34 base pair lox DNA sequence by binding to the 13 base pair inverted repeats and catalyzing strand cleavage and religation within the spacer region. The staggered DNA cuts made by Cre in the spacer region are separated by 6 base pairs to give an overlap region that acts as a homology sensor to ensure that only recombination sites having the same overlap region recombine.

Basically, the site specific recombinase system offers means for the removal of selection cassettes after homologous recombination. This system also allows for the generation of conditional altered alleles that can be inactivated or activated in a temporal or tissue-specific manner. Of note, the Cre and Flp recombinases leave behind a Lox or FRT "scar" of 34 base pairs. The Lox or FRT sites that remain are typically left behind in an intron or 3' UTR of the modified locus, and current evidence suggests that these sites usually do not interfere significantly with gene function.

Thus, Cre/Lox and Flp/FRT recombination involves introduction of a targeting vector with 3' and 5' homology arms containing the mutation of interest, two Lox or FRT sequences and typically a selectable cassette placed between the two Lox or FRT sequences. Positive selection is applied and homologous recombinants that contain targeted mutation are identified. Transient expression of Cre or Flp in conjunction with negative selection results in the excision of the selection cassette and selects for cells where the cassette has been lost. The final targeted allele contains the Lox or FRT scar of exogenous sequences.

Transposases—As used herein, the term "transposase" refers to an enzyme that binds to the ends of a transposon and catalyzes the movement of the transposon to another part of the genome.

As used herein the term "transposon" refers to a mobile genetic element comprising a nucleotide sequence which can move around to different positions within the genome of a single cell. In the process the transposon can cause mutations and/or change the amount of a DNA in the genome of the cell.

A number of transposon systems that are able to also transpose in cells e.g. vertebrates have been isolated or designed, such as Sleeping Beauty [Izsvák and Ivies Molecular Therapy (2004) 9, 147-156], piggyBac [Wilson et al. Molecular Therapy (2007) 15, 139-145], Tol2 [Kawakami et al. PNAS (2000) 97 (21): 11403-11408] or Frog Prince [Miskey et al. Nucleic Acids Res. December 1, (2003) 31(23): 6873-6881]. Generally, DNA transposons translocate from one DNA site to another in a simple, cut-and-paste manner. Each of these elements has their own advantages, for example, Sleeping Beauty is particularly useful in region-specific mutagenesis, whereas Tol2 has the highest tendency to integrate into expressed genes. Hyperactive systems are available for Sleeping Beauty and piggyBac. Most importantly, these transposons have distinct target site preferences, and can therefore introduce sequence alterations in overlapping, but distinct sets of genes. Therefore, to achieve the best possible coverage of genes, the use of more than one element is particularly preferred. The basic mechanism is shared between the different transposases, therefore we will describe piggyBac (PB) as an example.

PB is a 2.5 kb insect transposon originally isolated from the cabbage looper moth, *Trichoplusia ni*. The PB transposon consists of asymmetric terminal repeat sequences that flank a transposase, PBase. PBase recognizes the terminal repeats and induces transposition via a "cut-and-paste" based mechanism, and preferentially transposes into the host genome at the tetranucleotide sequence TTAA. Upon insertion, the TTAA target site is duplicated such that the PB transposon is flanked by this tetranucleotide sequence. When mobilized, PB typically excises itself precisely to reestablish a single TTAA site, thereby restoring the host sequence to its pretransposon state. After excision, PB can transpose into a new location or be permanently lost from the genome.

Typically, the transposase system offers an alternative means for the removal of selection cassettes after homologous recombination quit similar to the use Cre/Lox or Flp/FRT. Thus, for example, the PB transposase system involves introduction of a targeting vector with 3' and 5' homology arms containing the mutation of interest, two PB terminal repeat sequences at the site of an endogenous TTAA sequence and a selection cassette placed between PB terminal repeat sequences. Positive selection is applied and homologous recombinants that contain targeted mutation are identified. Transient expression of PBase removes in conjunction with negative selection results in the excision of the selection cassette and selects for cells where the cassette has been lost. The final targeted allele contains the introduced mutation with no exogenous sequences.

For PB to be useful for the introduction of sequence alterations, there must be a native TTAA site in relatively close proximity to the location where a particular mutation is to be inserted.

Genome editing using recombinant adeno-associated virus (rAAV) platform—this genome-editing platform is based on rAAV vectors which enable insertion, deletion or substitution of DNA sequences in the genomes of live mammalian cells. The rAAV genome is a single-stranded deoxyribonucleic acid (ssDNA) molecule, either positive- or negative-sensed, which is about 4.7 kb long. These single-stranded DNA viral vectors have high transduction rates and have a unique property of stimulating endogenous homologous recombination in the absence of double-strand DNA breaks in the genome. One of skill in the art can design a rAAV vector to target a desired genomic locus and perform both gross and/or subtle endogenous gene alterations in a cell. rAAV genome editing has the advantage in that it targets a single allele and does not result in any off-target genomic alterations. rAAV genome editing technology is commercially available, for example, the rAAV GENESIS™ system from Horizon™ (Cambridge, UK).

Methods for qualifying efficacy and detecting sequence alteration are well known in the art and include, but not limited to, DNA sequencing, electrophoresis, an enzyme-based mismatch detection assay and a hybridization assay such as PCR, RT-PCR, RNase protection, in-situ hybridization, primer extension, Southern blot, Northern Blot and dot blot analysis.

Sequence alterations in a specific gene can also be determined at the protein level using e.g. chromatography, electrophoretic methods, immunodetection assays such as ELISA and western blot analysis and immunohistochemistry.

In addition, one ordinarily skilled in the art can readily design a knock-in/knock-out construct including positive and/or negative selection markers for efficiently selecting transformed cells that underwent a homologous recombination event with the construct. Positive selection provides a means to enrich the population of clones that have taken up foreign DNA. Non-limiting examples of such positive markers include glutamine synthetase, dihydrofolate reductase (DHFR), markers that confer antibiotic resistance, such as neomycin, hygromycin, puromycin, and blasticidin S resistance cassettes. Negative selection markers are necessary to select against random integrations and/or elimination of a marker sequence (e.g. positive marker). Non-limiting examples of such negative markers include the herpes simplex-thymidine kinase (HSV-TK) which converts ganciclovir (GCV) into a cytotoxic nucleoside analog, hypoxanthine phosphoribosyltransferase (HPRT) and adenine phosphoribosyltransferase (ARPT).

Down-Regulation at the Polypeptide Level

Another agent which can be used along with some embodiments of the invention to downregulate a target is an aptamer. As used herein, the term "aptamer" refers to double stranded or single stranded RNA molecule that binds to specific molecular target, such as a protein. Various methods are known in the art which can be used to design protein specific aptamers. The skilled artisan can employ SELEX (Systematic Evolution of Ligands by Exponential Enrichment) for efficient selection as described in Stoltenburg R, Reinemann C, and Strehlitz B (Biomolecular engineering (2007) 24(4):381-403).

It will be appreciated that a non-functional analogue of at least a catalytic or binding portion of the target can be also used as an agent which downregulates the target (dominant negative).

Alternatively or additionally, small molecule or peptides can be used which interfere with protein function (e.g., catalytic or interaction).

Identification of agents which can be useful in cardiac regeneration is also contemplated according to the present teachings.

Accordingly, the method is performed by:

(a) contacting the agent with post natal cardiomyocytes that do down regulate ErbB-2; and (b) measuring an activity or expression of the ErbB-2 in the cardiomyocytes, wherein an upregulation in the ErbB-2 activity or expression following the contacting is indicative that the agent is useful cardiac tissue regeneration.

According to a specific embodiment, the cardiomyocytes correspond to murine P7.

Methods of determining CM proliferation are well known in the art, and include, but are not limited to, manual cell counting, MTT assay and a thymidine incorporation assay. According to some embodiments both ascertaining the nature of the cells as well as determining their proliferation are done.

For example, in some embodiments, the presence of proliferative cardiomyocytes is validated by confirming expression of at least one cardiomyocyte-specific marker produced by the cell. For example, the cardiomyocytes express cardiac transcription factors, sarcomere proteins, and gap junction proteins. Suitable cardiomyocyte-specific proteins include, but are not limited to, cardiac troponin I, cardiac troponin-C, tropomyosin, caveolin-3, GATA-4, myosin heavy chain, myosin light chain-2a, myosin light chain-2v, ryanodine receptor, and atrial natriuretic factor.

As another example, in some embodiments, cardiomyocytes are ascertained by detecting responsiveness to pharmacological agents such as beta-adrenergic agonists (e.g., isoprenaline), adrenergic beta-antagonists (e.g., esmolol), cholinergic agonists (e.g., carbochol), and the like.

Alternatively or additionally, validating the nature of the CMs is done by detecting electrical activity of the cells. Electrical activity can be measured by various methods, including extracellular recording, intracellular recording (e.g., patch clamping), and use of voltage-sensitive dyes. Such methods are well known to those skilled in the art.

Any of the agents described herein can be used alone or in combination e.g., ErbB-2 activating antibody and neuregulin.

For the sake of simplicity any of the agents are collectively referred to herein as "an agent" or "agents", although it should be appreciated that each possibility of an agent represents a separate embodiment of the present invention.

According to a specific embodiment, the methods described herein for inducing CM proliferation/cardiac regeneration are effected in vivo.

According to a specific embodiment, the methods described herein for inducing CM proliferation/cardiac regeneration are effected in vitro.

According to a specific embodiment, the methods described herein for inducing CM proliferation/cardiac regeneration are effected ex vivo.

According to a specific embodiment the cardiomyocytes are comprised in a tissue (a vascularized tissue).

The ability to induce CM proliferation renders the present teachings particularly suitable for the treatment of heart diseases where there is damage to the cardiac tissue or there is a risk for such damage.

The term "treating" refers to inhibiting, preventing or arresting the development of a pathology (i.e., heart disease, disorder or condition, e.g., ischemic heart disease) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age that suffer from the pathology. Preferably, this term encompasses individuals who are at risk to develop the pathology.

According to a specific embodiment, the heart disease is an ischemic heart disease.

An ischemic heart disease refers to a lack of oxygen flow to the heart or portion thereof, resulting in myocardial ischemic damage. As used herein, the phrase myocardial ischemic damage includes damage caused by reduced blood flow to the myocardium. Non-limiting examples of causes of an ischemic heart disease and myocardial ischemic damage include: decreased aortic diastolic pressure, increased intraventricular pressure and myocardial contraction, coronary artery stenosis (e.g., coronary ligation, fixed coronary stenosis, acute plaque change (e.g., rupture, hemorrhage), coronary artery thrombosis, vasoconstriction), aortic valve stenosis and regurgitation, and increased right atrial pressure. Non-limiting examples of adverse effects of myocardial ischemia and myocardial ischemic damage include myocyte damage (e.g., myocyte cell loss, myocyte hypertrophy, myocyte cellular hyperplasia), angina (e.g., stable angina, variant angina, unstable angina, sudden cardiac death), myocardial infarction, and congestive heart failure. Damage due to myocardial ischemia may be acute or chronic, and consequences may include scar formation, cardiac remodeling, cardiac hypertrophy, wall thinning, dilatation, and associated functional changes. The existence and etiology of acute or chronic myocardial damage and/or myocardial ischemia may be diagnosed using any of a variety of methods and techniques well known in the art including, e.g., non-invasive imaging (e.g., MRI, echocardiography), angiography, stress testing, assays for cardiac-specific proteins such as cardiac troponin, and evaluation of clinical symptoms. These methods and techniques as well as other appropriate techniques may be used to determine which subjects are suitable candidates for the treatment methods described herein.

According to a specific embodiment, the ischemic heart disease in the present invention includes, for example, coronary arteriosclerosis, acute myocardial infarction (AMI), myocardial infarction (MI), old MI, angina pectoris (AP) including stable angina, unstable angina, and effort angina, ischemic cardiomyopathy, heart failure, and other disease which causes necrosis of heart muscle that results from prolonged ischemia. As necrosis of heart muscle progresses, the damaged myocardiac tissue are replaced with fibrous tissue, thickness of the myocardial wall in the infarct zone gets thinner, and the cardiac inner cavity dilates, therefore cardiac function such as contractility deteriorates and results in heart failure.

Coronary arteriosclerosis is characterized by arteriosclerosis in the coronary artery that supplies nutrients to the heart. Angina pectoris is characterized by attacks of chest pain caused by impaired blood flow in the coronary artery. Myocardial infarction is characterized by myocardial necrosis caused by impaired blood flow in the coronary artery and by fatal complications coming therewith such as arrhythmia, cardiac failure, cardiac rupture, and pump failure. Impaired blood flow to the heart, a vital organ, is an essential characteristic of these ischemic heart diseases.

"Post-infarction myocardial remodeling" refers to a series of changes such as the hypertrophy of myocardial cells at non-infarction sites, increase in interstitial tissue (extracellular matrix), and the dilation of cardiac lumens, which occur in compensation for reduced cardiac function caused by thickening at infarction sites after myocardial infarction. Since long-term prognosis after myocardial infarction is correlated with the degree of left ventricular dysfunction, the suppression of myocardial remodeling is important for maintaining and conserving the function of the left ventricle.

The agents of some embodiments of the invention can be administered to an organism (e.g., human being) per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agent accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, intravenous, intraperitoneal, intranasal, or intraocular injections.

Alternately, one may administer the pharmaceutical composition in a local rather than systemic manner, for example, via injection of the pharmaceutical composition directly into a tissue region of a patient. For example by direct intraventricular, intracardiac, e.g., into the right or left ventricular cavity, into the common coronary artery. Also contemplated is administration of the composition directly to the myocardium e.g., either during open heart surgery or endomyocardial catheters guided by imaging e.g., ultrasound.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients effective to prevent, alleviate or ameliorate symptoms of a disorder (e.g., ischemic heart disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide for example, a cardiac tissue levels of the active ingredient that are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

The agent is delivered by an appropriate means to the site of defect (e.g., as described above). The site and subject are observed and tested for regeneration of the defective myocardium to determine that an effective amount of the composition has been delivered, particularly to observe new tissue growth, and also to determine that the new tissue has the contractility necessary for it to function usefully as myocardium. Tissue growth and contractility can be tested and observed by standard means, for example as described in Badylak et al, The Heart Surgery Forum, Extracellular Matrix for Myocardial Repair 6(2) E20-E26 (2003).

Compositions of some embodiments of the invention may, if desired, be presented in a pack or dispenser device, such as an FDA approved kit (e.g., comprising an agent that upragulates activity or expression of ErbB-2 (e.g., ErbB-2 activating antibody or mod-RNA for ErbB-2 in combination with neuregulin), which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The agents as described herein can also be immobilized to an implant (e.g., stent) where they can be slowly released (or sustained released) therefrom.

The agent as described herein be combined with other treatment modalities. These other treatments include medication (e.g., blood pressure medication, calcium channel blockers, digitalis, anti-arrhythmics, ACE inhibitors, anticoagulants, immunosuppressants, pain relievers, vasodilators, etc.), angioplasty, stent placement, coronary artery bypass graft, cardiac assist device (e.g., left ventricular assist device, balloon pump), pacemaker placement, heart transplantation, etc. In certain embodiments, the agent provides a bridge to recover for a subject waiting to undergo heart transplantation.

It is expected that during the life of a patent maturing from this application many relevant agents that upregulate ErbB-2 activity or expression will be developed and the scope of the term agent is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Methods

Mouse Experiments

Experiments were approved by the Animal Care and Use Committee of the Weizmann Institute of Science. To track the cardiac muscle cell lineage, the present inventors intercrossed αMHC-Cre to ROSA26-td Tomato mice. αMHC-Cre mice carry the Cre coding sequence inserted after the alpha myosin heavy chain promoter (αMHC), which can drive high-efficiency gene recombination in CMs[40]. ROSA26-tdTomato indicator mice harbor a conditional red fluorescent protein variant allele that requires CRE-mediated recombination for expression[64]. This system allowed us to clearly visualize RFP-labeled-CMs in culture. ROSA26-tdTomato and αMHC-Cre mice were maintained on a C57BL/6 background.

CM-restricted deletion of Erbb2 (Erbb2-cKO) was generated by crossing Erbb2$^{flox/flox}$ [41] to Erbb2$^{lacZ/+}$; αMHC-Cre mice (see FIG. 2A). The Erbb2$^{lacZ/+}$ mice used in this study carry an allele that encodes a nonfunctional ErbB2-galactosidase fusion protein lacking the tyrosine kinase domain[42]. In some experiments, addition of ROSA26-tdTomato allele to this system has been used to label cardiac muscle cell lineage in Erbb2-cKO mice. Erbb2$^{flox/flox}$ and Erbb2$^{lacZ/+}$ mice were maintained on a C57BL/6 background.

Doxycycline inducible CM restricted overexpression of a constitutively active Erbb2 (caErbb2) was generated by crossing TetRE-caErbb2 mouse line[65] (a B6SJLF1/J transgenic line in which this mutated Erbb2 is placed under the control of a minimal CMV promoter and the tetracycline-responsive element) with αMHC-tTA[66], which expresses the tetracycline-responsive transcriptional activator (tTA) under the control of the human alpha myosin heavy chain promoter (αMHC) promoter (see FIG. 10A). αMHC-tTA strain was created in the FVB background and then the line was backcrossed to C57BL/6. Doxycycline (DOX, Harlan Laboratories) was administered in the food to repress transgene expression.

Oligo sequences for genotyping the above described mouse lines are listed in the Table 2.

Myocardial Infarction

Myocardial infarction at juvenile (P7) or adult stage was induced by ligation of the left anterior descending coronary artery (LAD) as previously described[67]. P7 mice were anesthetized by cooling on an ice bed for 4 minutes, while adult mice were sedated with isofluorane (Abbott Laboratories, Abbot Park, Ill., USA) and, following tracheal intubation, were artificially ventilated. Lateral thoracotomy at the fourth intercostal space was performed by blunt dissection of the intercostal muscles following skin incision. Following LAD ligation thoracic wall incisions were sutured with 6.0 non absorbable silk sutures, and the skin wound closed using skin adhesive. Mice were then warmed for several minutes until recovery. The hearts were harvested for analysis at different time points, as indicated in FIGS. 7A-K.

Histology (Hematoxylin/Eosin and Masson's Trichrome)

Murine hearts were fixed in 4% paraformaldehyde, embedded in paraffin and sectioned. Hematoxylin/Eosin (H&E) and Masson's trichrome (MT) staining were performed according to standard procedures. For analysis of cardiac regeneration following MI procedure, paraffin sections were cut through the entire ventricle from apex to base into serial sections with intervals of 0.4 mm. Masson's Trichrome (MT) staining was used for detection of fibrosis. Scar size was quantified in each section with ImageJ software (National Institutes of Health, MA, USA) based on Masson's trichrome staining. Total scar volume was calculated as sum of scar volumes between serial sections. Scar volume between serial sections was calculated with the formula of a truncated pyramid: $\frac{1}{3}(\alpha 1 + \alpha 2 + \sqrt{\alpha 1 * \alpha 2})$, where a1 and a2 are the scar areas of 2 serial sections and i is the interval (0.4 mm) between them.

Cardiomyocytes Isolation and Culture

Primary cardiomyocytes were isolated from 1-day-old (P1) and 7-days-old (P7) mice using a neonatal dissociation kit (gentleMACS, Germany), according to the manufacturer's instructions, and cultured in gelatin-coated (0.1%, G1393, Sigma, St. Louis, Mo., USA) wells with DMEM/F12 medium supplemented with L-glutamine, Na-pyruvate, Non-essential amino acids, penicillin, streptomycin, 5% Horse serum and 10% FBS (hereafter referred to as "complete-medium") at 37° C. and 5% CO2.

In experiments involving administration of Neuregulin-1b (NRG1, R&D Systems, MN, USA), the cells were allowed to adhere for 48 hours in complete-medium. Subsequently, the medium was replaced with an FBS-deprived complete-medium containing the indicated NRG1 doses for 72 hours. BrdU (10 μM, B5002, Sigma, St. Louis, Mo., USA) was introduced along with NRG1. Cells were fixed in 4% PFA and stained for markers of interest.

In cultures isolated from hearts of P7 ctrl and caErbb2-cOE animals, the cells were seeded in the aforementioned complete-medium for 48 hours, in the presence of the following substances: MEK/MAPKK kinase inhibitor regarded in the text as ERK inhibitor (2 μM, PD0325901, Tocris Bioscience, Bristol, UK), AKT1/2 inhibitor (5 μM, AKT inhibitor VIII, ApexBio, Houston, Tex., USA), GSK3β inhibitor (10 μM, CHIR-99021, Axon Medchem, Netherlands), β-Catenin inhibitor (10 μM, IWR-1, Sigma, St. Louis, Mo., USA), p38 inhibitor (10 μM SB202190, Merck Millipore, Massachusetts, USA), Periostin (500 ng/ml; BioVendor, Brno Czech Republic), FGF1 (100 ng/ml; R&D Systems, MN, USA). The dissolving reagents were added to unstimulated samples. Subsequently, cells were fixed in 4% PFA and stained for markers of interest.

Immunofluorescence Analysis

Heart sections underwent deparaffinization, fixation in 4% PFA (5 minutes) and microwave antigen retrieval in EDTA or citric acid buffer, followed by gradual chilling. Then heart sections and cultured cells were processed in the following manner. Samples were permeabilized with 0.5% Triton X-100 in PBS for 5 minutes and blocked with 5% bovine serum albumin (BSA, Sigma, St. Louis, Mo., USA) in PBS containing 0.1% Triton for 1 hour at room temperature. Then samples were incubated 1 hour at room temperature or overnight at 4° C. with the following antibodies diluted in 3% BSA blocking solution: anti-Troponin T (1:200, ab33589, Abcam, Cambridge, Mass., USA), anti-Troponin I (1:200, ab47003, Abcam, Cambridge, Mass., USA) or anti-NKX2.5 (1:200, ab35842, Abeam, Cambridge, Mass., USA) Abs were used to identify CMs. Anti-Ki67 antibody (1:200, 275R, Cell Marque, Austin, Tex., USA) anti-BRDU antibody (1:100, G3G4, DSHB, Iowa City, Iowa, USA), anti-phosphorylated-Histone3 (pH3) antibody (1:200, SC-8656-R, Santa Cruz Biotechnology Inc., Santa Cruz, Calif., USA) and anti-Aurora B (1:100, 611082, BD Transduction Laboratories, Lexington, Ky., USA) were used to analyze cell cycle re-entry, DNA synthesis, karyokinesis and cytokinesis, respectively. Other Abs used in the study: anti-ErbB2 (1:50, sc-284, Santa Cruz Biotechnology Inc., Santa Cruz, Calif., USA), anti-αSMA (1:50, A5691, Sigma, St. Louis, Mo., USA), RUNX1 (1:200, ab92336, Abcam, Cambridge, Mass., USA), anti-DAB2 (1:200, sc-13982, Santa Cruz Biotechnology Inc., Santa Cruz, Calif., USA), anti-β-Catenin (1:200, ab32572, Abcam, Cambridge, Mass., USA). After three washes with PBS, 10 minutes each, samples were stained for 1 hour at room temperature or overnight at 4° C. with fluorescent secondary antibodies (Abeam, Cambridge, Mass., USA) followed by 10 minutes of DAPI (4,6-diamidino-2-phenylindole dihydrochloride) staining for nuclei visualization. Slides were mounted with Immu-mount (9990412, Thermo scientific, MA, USA) and viewed under a fluorescence microscope (Nikon Intensilight or Nikon eclipse 90i, Nikon, Düsseldorf, Germany) or spinning disk confocal microscope (Carl Zeiss, Thornwood, N.Y., USA) as specified in the figure legends.

For CD34 staining, slides were deparaffinized and treated with pre-chilled (−20° C.) acetone for 7 minutes. Subsequently, the slides underwent antigen retrieval in EDTA buffer in a pressure cooker followed by gradual chilling. After reaching room temperature, slides were washed in PBS, blocked with 20% Horse Serum with 0.2% Triton in PBS, for 1 h. Slide were incubated over-night with anti-CD34 antibody (1:100, CL8927AP, Cedarlane Laboratories, Ontario, Canada) at room temperature. Co-staining with anti-cTnT antibodies was usually performed to simultaneously identify CMs. After washing the slides with PBS, a signal amplification step was performed by adding biotin-sp-conjugated antibody (1:150, 712-065-153, Jackson ImmunoResearch, West Grove, Pa., USA) in 2% horse serum in PBS, for 1.5 h. Subsequently, a cy3-conjugated streptavidin antibody (1:150, 016-160-084, Jackson ImmunoResearch, West Grove, Pa., USA) was added for 45 min in RT. Following DAPI staining the slide were mounted with Immu-mount (9990412, Thermo scientific, MA, USA).

Assessment of Post-MI Neovascularization

Slides of injured hearts were stained for CD34 and visualized under a fluorescence microscope (Nikon Intensilight or Nikon eclipse 90i, Nikon, Düsseldorf, Germany). At least 3 images per heart were photographed at different regions, and images were quantified using the ImageJ software (National Institutes of Health, MA, USA).

Assessment of CM Size

In vitro, the area of the CMs was quantified using ImageJ software (National Institutes of Health, MA, USA) based on Troponin T (cTnT) or Troponin I (cTnI) staining or tdTomato genetic labeling (see "mouse experiments" section above).

In vivo, the cross-sectional area of CMs was assessed based on WGA staining. For that, slides were deparaffinized, rinsed in PBS and then incubated with primary antibody against WGA conjugated to Alexa Fluor 488 (1:200, Invitrogen Corporation, Carlsbad, Calif., USA). Slides were then rinsed 3 times in PBS, mounted with Immu-mount (9990412, Thermo scientific, MA, USA) and imaged by spinning disk confocal microscope (Carl Zeiss, Thornwood, N.Y., USA). Only CMs which were aligned transversely were considered for the quantification of the cross sectional area, while only CMs which were aligned longitudinally were considered for the quantification of the length.

Assessment of CM Number in Adult Mice

Heart weight was multiplied by the known value for specific gravity of muscle tissue (1.06 gm/ml) to obtain heart volume. The calculated heart volume was multiplied by the fraction occupied by CMs (calculated in heart section based on cTnT staining) to determine the total volume of CMs. Average CM volume was calculated utilizing measurements from CM cross-sectional areas multiplied by the average of CM lengths (see "assessment of CM size" section above). The number of CM per heart was calculated as the quotient of total volume of CMs and average CM volume, similarly to previous studies[68, 69].

Transcriptional Analysis RNA was isolated using the NucleoSpin RNA extraction kit (Macherey-Nagel, Düren, Germany), according to the manufacturer's instructions. RNA was quantified using a NanoDrop spectrophotometer. A High Capacity cDNA Archive Kit (Applied Biosystems, Foster City, Calif., USA) was used to reverse transcribe 1 µg of purified RNA according to the manufacturer's instructions. All PCR reactions were performed using Fast SYBR Green PCR Master Mix (Applied Biosystems, Foster City, Calif., USA). Oligo sequences for real-time PCR analysis performed in this study are listed in the Table 3.

Western Blot Analysis

Western blotting was performed with the SDS-PAGE Electrophoresis System. Total tissue extracts were prepared, 50 µg protein of each sample was fractionated by gel electrophoresis, and transferred to nitrocellulose membranes. The following primary antibodies were used: anti-Erbb2 (#4290, Cell Signaling, Massachusetts, USA) anti-Erbb2 (sc-284, Santa Cruz, Santa Cruz, Calif., USA), anti-phospho-Erbb2, #2247, Cell Signaling, Massachusetts, USA), anti-cKIT (sc-5535, Santa Cruz, Calif., USA), anti-beta-catenin (ab32572, Abcam, Cambridge, Mass., USA), anti-ERK2 (sc-154, Santa Cruz, Calif., USA), anti-phospho-ERK (#4370, Cell Signaling, Massachusetts, USA), anti-AKT1 (sc-1618, Santa Cruz, Calif., USA), anti-phospho-AKT (#4060, Cell Signaling, Massachusetts, USA), anti alpha-tubulin (T5168, Sigma-Aldrich, St. Louis, Mo., USA). Horseradish peroxidase anti-mouse, anti-rabbit or anti-goat (Sigma, St. Louis, Mo., USA) were used as secondary antibodies. The signal was detected by the super-signal-enhanced chemiluminescence system (Pierce).

Echocardiography

Heart function was evaluated by transthoracic echocardiography performed on sedated mice (Isoflurane, Abbott Laboratories, Abbot Park, Ill., USA) using a VisualSonics device.

Cardiac Magnetic Resonance Imaging (MRI)

MRI experiments were performed as previously described[70]. Briefly, MRI experiments were performed on 9.4 Tesla BioSpec Magnet 94/20 USR system (Bruker, Germany). During the MRI scanning, mice were anesthetized with Isofluorane (Abbott Laboratories, Abbot Park, Ill., USA; 3% for induction, 1-2% for maintenance) mixed with oxygen (1 liter/min) and delivered through a nasal mask. Once anesthetized, the animals were placed in a supine position in a head-holder to assure reproducible positioning inside the magnet. Respiration rate was monitored and kept throughout the experimental period around 30-45 breaths per min. During imaging, body temperature was maintained using a circulating water system adjusted to maintain the mouse body temperature at 37° C.

A linear RF resonator for excitation and an actively decupled 2 cm surface coil for detection were used. Acquisition of cine images at both long-axis and multiple short-axis orientations was performed using a retrospectively gated fast low angle shot (FLASH) sequence. Specific parameters included 10 frames per cardiac cycle for both short-axis and long-axis images. Imaging parameters for short-axis acquisition were: 6 to 8 slices; slice thickness=1.0 mm; interslice distance=1.0 mm; flip angle=40°; repetition time (TR)=50 ms; echo time (TE)=2.0 ms; number of repetitions=80; matrix=256×128 with zero-filling to 256× 256; field of view (FOV)=30×30 mm$^2$; and acquisition time≈8.5 minutes. Imaging parameters for long-axis acquisition: slice thickness=1.0 mm; flip angle=15°; TR=5.76 ms; TE=3.07 ms; number of repetitions=250; matrix=256×128 zero-filling to 256×256; FOV=35×35 mm$^2$; acquisition time≈3 minutes.

Statistical Analysis

Sample size was chosen empirically following previous experience in the assessment of experimental variability. No statistical method was used to predetermine sample size. Generally all experiments were carried out with n≥3 biological replicates. Used animal numbers or cells per groups are described in the respective figure legends. We ensured that experimental groups were balanced in terms of animal age, sex and weight unless otherwise specified. Animals were genotyped before the experiment and were caged together and treated in the same way. Premature death of animals was a criterion for exclusion.

Variance was comparable between groups throughout the manuscript. We chose the adequate tests according to the data distributions to fulfill test assumptions. The experiments were not randomized. The investigators were not blinded to allocation during experiments and outcome assessment. Whenever normality could be assumed the Student t-test or analysis of variance (ANOVA) followed by Tukey's or Sidak's test was used to compare group means, as specified in the figure legends. Log-rank (Mantel-Cox) test was used to compare survival curves. p value <0.05 was considered to represent a statistically significant difference. In all panels numerical data are presented as mean+S.E.M; results are marked with one asterisk (*) if p<0.05, two () if p<0.01, three (*) if p<0.001 and four (****) if p<0.0001; Statistics source data can be found in Table 1.

Panels in FIGS. 1I, 2C, 3D, 3E, 3F, 5A, 5B, 6A, 6E, 7I and FIGS. 9A, 9B, 9D, 10B, 10C, 10D, 10E, 11C, 11D, 11E, 11F, 11G, 12B, 12C, 13A show a representative image of three independent experiments.

Methods Associated References

64. Madisen, L. et al. A robust and high-throughput Cre reporting and characterization system for the whole mouse brain. *Nat Neurosci* 13, 133-140 (2010).
65. Xie, W., Chow, L. T., Paterson, A. J., Chin, E. & Kudlow, J. E. Conditional expression of the ErbB2 oncogene elicits reversible hyperplasia in stratified epithelia and up-regulation of TGFalpha expression in transgenic mice. *Oncogene* 18, 3593-3607 (1999).
66. Yu, Z., Redfern, C. S. & Fishman, G. I. Conditional transgene expression in the heart. *Circ Res* 79, 691-697 (1996).
67. Mahmoud, A. I., Porrello, E. R., Kimura, W., Olson, E. N. & Sadek, H. A. Surgical models for cardiac regeneration in neonatal mice. *Nat Protoc* 9, 305-311 (2014).
68. Chaudhry, H. W. et al. Cyclin A2 mediates cardiomyocyte mitosis in the postmitotic myocardium. *The Journal of biological chemistry* 279, 35858-35866 (2004).
69. Jackson, T. et al. The c-myc proto-oncogene regulates cardiac development in transgenic mice. *Mol Cell Biol* 10, 3709-3716 (1990).
70. Vandoorne, K. et al. Multimodal imaging reveals a role for Akt1 in fetal cardiac development. *Physiological reports* 1, e00143 (2013).

TABLE 1

| Panel | Test | Error | Data | Mice | Normal | Total | Samples |
|---|---|---|---|---|---|---|---|
| 5d | Two-tailed unpaired Student's t-test | S.E.M | ctrl: 171 NKx2.5+ cells assessed from 54 fields caErbb2: 753 NKx2.5+ cells assessed from 45 fields | 11 mice: 5 for ctrl, 6 caErbb2 | yes | 924 Nkx2.5+ cells | 11 mice |
| 5e | Two-tailed unpaired Student's t-test | S.E.M | ctrl: 270 CMs assessed from 20 fields caErbb2: 328 CMs assessed from 36 fields | 8 mice: 4 for ctrl, 4 caErbb2 | yes | 598 CMs | 8 mice |
| 5f | Two-tailed unpaired Student's t-test | S.E.M | ctrl: 611 CMs assessed from 50 fields caErbb2: 1308 CMs assessed from 98 fields | 11 mice: 5 for ctrl, 6 caErbb2 | yes | 1919 CMs | 11 mice |
| 5g | Two-tailed unpaired Student's t-test | S.E.M | ctrl: 281 CMs assessed from 30 fields caErbb2: 296 CMs assessed from 14 fields | 6 mice: 3 for ctrl, 3 caErbb2 | yes | 577 CMs | 6 mice |
| 6b | One-way ANOVA/ Tukey's test | S.E.M | ctrl - untreated: 1935 CMs assessed from 173 fields ctrl - ERKi: 234 CMs assessed from 15 fields ctrl - AKTi: 233 CMs assessed from 18 fields caErbb2 - untreated: 1279 CMs assessed from 54 fields caErbb2 - ERKi: 513 CMs assessed from 24 fields caErbb2 - AKTi: 1138 | ctrl: 26 samples caErbb2: 28 samples | yes | 5332 CMs | 54 samples |

TABLE 1-continued

| | | | | | | | |
|---|---|---|---|---|---|---|---|
| 6c | One-way ANOVA/ Tukey's test | S.E.M | CMs assessed from 43 fields ctrl - untreated: 431 CMs assessed from 65 fields ctrl - ERKi: 392 CMs assessed from 27 fields ctrl - AKTi: 232 CMs assessed from 45 fields caErbb2 - untreated: 1088 CMs assessed from 114 fields caErbb2 - ERKi: 921 CMs assessed from 40 fields caErbb2 - AKTi: 570 CMs assessed from 94 fields | ctrl: 13 samples caErbb2: 24 samples | yes | 3634 CMs | 37 samples |
| 6d | One-way ANOVA/ Tukey's test | S.E.M | ctrl - untreated: 53 CMs caErbb2 - untreated: 122 CMs caErbb2 - ERKi: 87 CMs caErbb2 - AKTi: 76 CMs | ctrl: 3 samples caErbb2: 12 samples | yes | 338 CMs | 15 samples |
| 6f | One-way ANOVA/ Tukey's test | S.E.M | ctrl - untreated: 1068 CMs assessed from 18 fields ctrl - GSK3bi: 1331 CMs assessed from 22 fields ctrl - beta-catenini: 978 CMs assessed from 6 fields caErbb2 - untreated: 1142 CMs assessed from 19 fields caErbb2 - GSK3bi: 808 CMs assessed from 17 fields caErbb2 - beta-catenini: 480 CMs assessed from 5 fields | ctrl: 26 samples caErbb2: 20 samples | yes | 5807 CMs | 46 samples |
| 6g | One-way ANOVA/ Tukey's test | S.E.M | ctrl - untreated: 620 CMs assessed from 55 fields ctrl - GSK3bi: 716 CMs assessed from 78 fields ctrl - beta-catenini: 391 CMs assessed from 45 fields caErbb2 - untreated: 1079 CMs assessed from 75 fields caErbb2 - GSK3bi: 1017 CMs assessed from 138 fields caErbb2 - beta- | ctrl: 17 samples caErbb2: 27 samples | yes | 4778 CMs | 44 samples |

TABLE 1-continued

| | | | | | | | |
|---|---|---|---|---|---|---|---|
| 6h | One-way ANOVA/ Tukey's test | S.E.M | catenini: 955 CMs assessed from 75 fields ctrl - untreated: 53 CMs caErbb2 - untreated: 122 CMs caErbb2 - GSK3bi: 106 CMs caErbb2 - beta-catenini: 86 CMs | ctrl: 3 samples caErbb2: 11 samples | yes | 367 CMs | 14 samples |
| 7c | Two-tailed unpaired Student's t-test | S.E.M | ctrl: 1789 CMs assessed from 16 fields caErbb2: 2448 CMs assessed from 25 fields | 7 mice: 3 ctrl, 4 caErbb2 | yes | 4237 CMs | 7 mice |
| 7d | Two-tailed unpaired Student's t-test | S.E.M | ctrl: 3164 CMs assessed from 43 fields caErbb2: 2453 CMs assessed from 37 fields | 6 mice: 3 ctrl, 6 caErbb2 | yes | 5617 CMs | 6 mice |
| 7e | Two-tailed unpaired Student's t-test | S.E.M | ctrl: 1716 CMs assessed from 24 fields caErbb2: 2073 CMs assessed from 25 fields | 7 mice: 3 ctrl, 4 caErbb2 | yes | 3789 CMs | 7 mice |
| 7f | Two-tailed unpaired Student's t-test | S.E.M | ctrl: 1607 CMs assessed from 93 fields caErbb2: 1022 CMs assessed from 93 fields | 6 mice: 3 ctrl, 3 caErbb2 | yes | 2629 CMs | 6 mice |
| 7g | Two-way ANOVA/ Sidak's test | S.E.M | n = 18 mice | 18 mice: 6 ctrl, 8 ctrl (MI), 4 transient caErbb2 (MI) | yes | 18 mice | — |
| 7h | Two-way ANOVA/ Sidak's test | S.E.M | n = 13 mice | 13 mice: 4 ctrl, 5 ctrl(MI), 4 transient caErbb2 | yes | 13 mice | — |
| 7j | Two-tailed unpaired Student's t-test | S.E.M | n = 17 mice | 17 mice: 10 ctrl, 7 caErbb2 | yes | 17 mice | — |
| 7k | Two-tailed unpaired Student's t-test | S.E.M | n = 9 mice | 9 mice: 5 ctrl, 4 caErbb2 | yes | 9 mice | — |
| Supplementary 1c | Two-tailed unpaired Student's t-test | S.E.M | n = 22 mice | 22 mice: 12 ctrl and 10 Erbb2-cKO | yes | 22 mice | — |
| Supplementary 1e | Two-tailed unpaired Student's t-test | S.E.M | n = 51 mice | 51 mice: 36 ctrl and 15 Erbb2-cKO | no | 51 mice | — |
| Supplementary 1f | Two-tailed unpaired Student's t-test | — | ctrl: n = 284 CMs assessed from 3 fields Erbb2-cKo: n = 552 CMs assessed from 3 fields | 6 mice: 3 ctrl, 3 Erbb2-cKO | yes | 836 CMs | 6 mice |
| Supplementary 1g | Two-tailed unpaired Student's t-test | S.E.M | n = 8 mice | 8 mice: 4 ctrl and 4 Erbb2-cKO | yes | 8 mice | — |

TABLE 1-continued

| | | | | | | | |
|---|---|---|---|---|---|---|---|
| Supplementary 1h | Two-tailed unpaired Student's t-test | S.E.M | n = 15 mice | 8 mice: 11 ctrl and 4 Erbb2-cKO | yes | 15 mice | — |
| Supplementary 2f | Two-tailed unpaired Student's t-test | S.E.M | n = 14 mice | 14 mice: 8 ctrl and 6 caErbb2 | yes | 14 mice | — |
| Supplementary 2g | Two-tailed unpaired Student's t-test | S.E.M | n = 14 mice | 14 mice: 5 ctrl and 9 caErbb2 | yes | 14 mice | — |
| Supplementary 2h | Two-tailed unpaired Student's t-test | S.E.M | n = 20 mice | 20 mice: 14 ctrl and 6 caErbb2 | yes | 20 mice | — |
| Supplementary 3a | Two-tailed unpaired Student's t-test | — | ctrl: 154 CMs caErbb2: 152 CMs | 6 mice: 3 ctrl and 3 caErbb2 | yes | 306 CMs | 6 mice |
| Supplementary 3b | Two-tailed unpaired Student's t-test | S.E.M | n = 6 mice | 6 mice: 3 ctrl and 3 caErbb2 | yes | 6 mice | — |
| Supplementary 4a | One-way ANOVA/ Tukey's test | S.E.M | ctrl: 99 CMs assessed from 6 fields caErbb2 - untreated: 207 CMs assessed from 22 fields caErbb2 - ERK-i: 82 Cms assessed from 11 fields caErbb2 - AKT-i: 78 CMs assessed from 14 fields | ctrl: 5 samples caErbb2: 19 samples | yes | 466 CMs | 24 samples |
| Supplementary 4d | One-way ANOVA/ Tukey's test | S.E.M | ctrl - untreated: 523 CMs assessed from 43 fields ctrl - P38-i: 383 CMs assessed from 29 fields ctrl - FGF1: 796 CMs assessed from 54 fields ctrl - Periostin: 415 CMs assessed from 49 fields caErbb2 - untreated: 1446 CMs assessed from 69 fields caErbb2 - P38-i: 675 | ctrl: 22 samples caErbb2: 26 samples | yes | 6013 CMs | 48 samples |

TABLE 1-continued

| | | | | | | | |
|---|---|---|---|---|---|---|---|
| | | | CMs assessed from 36 fields caErbb2 - FGF1: 598 CMs assessed from 48 fields caErbb2 - Periostin: 1177 CMs assessed from 78 fields | | | | |
| Supplementary 4e | One-way ANOVA/ Tukey's test | S.E.M | ctrl - untreated: 390 CMs assessed from 66 fields ctrl - P38-i: 300 CMs assessed from 45 fields ctrl-FGF1: 560 CMs assessed from 45 fields ctrl - Periostin: 211 CMs assessed from 30 fields caErbb2 - untreated: 749 CMs assessed from 105 fields caErbb2 - P38-i: 584 CMs assessed from 90 fields caErbb2 - FGF1: 763 CMs assessed from 74 fields caErbb2 - Periostin: 660 CMs assessed from 84 fields | ctrl: 16 samples caErbb2: 27 samples | yes | 4217 CMs | 43 samples |
| Supplementary 4f | One-way ANOVA/ Tukey's test | S.E.M | ctrl - untreated: 53 CMs caErbb2 - untreated: 151 CMs caErbb2 - P38-i: 151 CMs caErbb2 - FGF1: 63 CMs caErbb2 - Periostin: 66 CMs | ctrl: 3 samples caErbb2: 14 samples | yes | 484 CMs | 17 samples |

TABLE 1-continued

| Supplementary 5b | Two-tailed unpaired Student's t-test | S.E.M | ctlr - border zone: 12 fields ctlr - scar zone: 13 fields caErbb2 - border zone: 8 fields caErbb2 - scar zone: 17 fields | 6 mice: 3 ctrl, 6 caErbb2 | yes | 50 fields | 6 mice |
|---|---|---|---|---|---|---|---|

TABLE 2

| Gene | Forward primer | Reverse primer |
|---|---|---|
| Rosa26-tdTomato | GGCATTAAAGCAGCGTATCC/5 | CTGTTCCTGTACGGCATGG/11 |
| aMHC-Cre | GGCCAGCTAAACATGCTTCA/6 | ACACCAGAGACGGAAATCCATC/12 |
| Erbb2$^{Lacz}$ | CCACCCTCTCGCTCCAGCTGGTGGA/7 | CGGGCCTCTTCGCTATTACGGGAGC/13 |
| Erbb2$^{flox}$ | TTTATGTGGGCACGCTTAGAAC/8 | CTAGAAGTCTGATTTGCGGTAT/14 |
| TetRE-caErbb2 | AAGAAGAGCCCAAGCTGGA/9 | GTGTACGGTGGGAGGCCTAT/15 |
| aMHC-tTA | CGCTGTGGGGCATTTTACTTTAG/10 | CATGTCCAGATCGAAATCGTC/16 |

TABLE 3

| Gene | Forward primer | Reverse primer |
|---|---|---|
| Nrg1 | ATCGCCCTGTTGGTGGTCGG/17 | AGCTTCTGCCGCTGTTTCTTGGT/25 |
| Erbb4 | GCCCCAAAGCCAACGTGGAGT | GCGGCATCAGCTGCGTAACC/26 |
| Erbb2 | CGCTGCCCCAGTGGTGTGAAG18 | GCAGCCTCGTTCGTCCAGGT/27 |
| Acta1 | GACATCAAAGAGAAGCTGTG/19 | ACTCCATACCGATAAAGGAAG/28 |
| Nppa | GAGAGAAAGAAACCAGAGTG/20 | GTCTAGCAGGTTCTTGAAATC/29 |
| Nppb | AATTCAAGATGCAGAAGCTG/21 | GAATTTTGAGGTCTCTGCTG/30 |
| aMyHC | AATCCTAATGCAAACAAGGG/22 | CAGAAGGTAGGTCTCTATGTC/31 |
| bMyHC | TTGGGAAATTCATCCGAATC/23 | CCAGAAGGTAGGTCTCTATG/32 |
| hprt | TGGCCGGCAGCGTTTCTGAG24 | GTCGGCTCGCGGCAAAAAGC/33 |

Example 1

ErbB2 is Required for Cardiomyocyte Proliferation and Heart Integrity in Neonates The present inventors first sought to determine the effect of NRG1 on CM proliferation during the transient postnatal regenerative window in mice[12]. In vitro administration of NRG1 promoted a dose-dependent increase in P1 CM proliferation, with profoundly reduced effects at P7, as shown by immunostaining for markers of cell cycle activity, DNA synthesis, mitosis, cytokinesis and by counting newly formed CMs (FIGS. 1A-E). In order to gain insights into the molecular mechanisms that exert distinct NRG1 proliferative responses in P1 vs. P7 CMs, the present inventors analysed the expression of NRG receptors Erbb4 and Erbb2, in total heart samples. Levels of Erbb2 mRNA, and of both total and active phosphorylated (p)-ErbB2 protein, were significantly downregulated at P7, while Erbb4 and Nrg1 mRNA levels were unchanged (FIGS. 1F-H). Immunofluorescence analysis confirmed the sharp reduction in ErbB2 protein expression in P7 CMs, which was further reduced at P28 (FIG. 1I). The reduced ability of NRG1 to stimulate CM cell cycle activity from P1 to P7, and the simultaneous down-regulation of ErbB2 expression, suggest that declining ErbB2 levels might limit the postnatal CM proliferative and regenerative windows.

Next, the present inventors conditionally deleted Erbb2 in CMs by crossing αMHC-Cre[40] with Erbb2$^{LacZ/flox}$ mice[41,42] (FIG. 2A). Analysis of ErbB2 protein expression in Erbb2$^{lacZ/flox}$; αMHC-Cre (Erbb2-cKO) hearts confirmed that the Erbb2$^{flox}$ allele was efficiently recombined in CMs (FIG. 9A). Erbb2-cKO pups were recovered at Mendelian frequency, although ~20% were already dead at birth and the remaining died in the following days (FIG. 2B). At birth, Erbb2-cKO hearts were markedly enlarged, but with only a slight increase in heart weight:body weight ratio (FIGS. 9B-E). Histological examination and echocardiographic analysis confirmed a dilated cardiomyopathy, failing heart, with thin walls showing decreased contractility (FIGS. 2C,D).

Figure 9F:
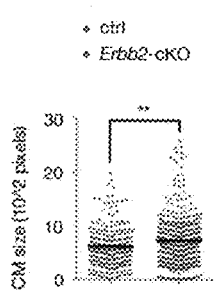
Figure 9G:
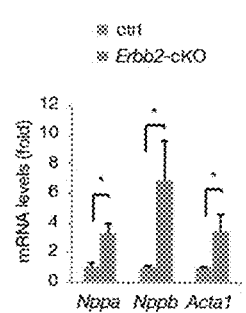
Figure 9H:
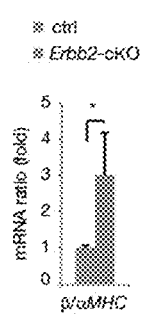

CM number and cell-cycle activity were dramatically reduced in Erbb2-cKO mice at birth (FIGS. 2E,F), despite a compensatory increase in Nrg1 expression (FIG. 2G). Erbb2-cKO CMs also developed compensatory hypertrophy as can be seen in cultured CMs (FIG. 9F). Consistently, mRNA levels for genes encoding atrial natriuretic factor (Nppa), brain natriuretic factor (Nppb), skeletal α-actin (Acta1) and the ratio of mRNAs levels of myosin heavy chain isoform (β/α-MHC ratio), markers of pathological cardiac hypertrophy, were significantly increased in Erbb2-cKO hearts compared with controls (FIGS. 9G, H). These data suggest that despite the proliferative deficit and dilatation, a compensatory hypertrophic response occurs in Erbb2-cKO hearts. Finally, NRG1 was unable to induce CM proliferation in neonatal Erbb2-cKO CMs (FIGS. 2H-J). These findings demonstrate that the proliferative response of neonatal CMs to NRG1 is direct and requires ErbB2. Thus, ErbB2 is necessary for NRG1-induced CM proliferation during embryonic/foetal and neonatal stages.

Example 2

Postnatal Activation of ErbB2 Promotes Cardiomegaly with Extensive Cardiomyocyte Hypertrophy, Dedifferentiation and Proliferation Then the present inventors asked whether induction of ErbB2 signalling after birth could bypass the CM cell cycle exit and differentiation that develops over the first postnatal week, and hence broaden the postnatal CM proliferative window. In the rat NEU oncoprotein, a valine to glutamic acid substitution within the transmembrane domain of ErbB2 is sufficient to confer autologous signalling independently of NRG1-mediated activation[43, 44]. The present inventors generated a "Tet-Off" transgenic mouse model (αMHC-tTA;TetRE-caErbB2) expressing a constitutively active version of Erbb2 (caErbb2) corresponding to the NEU mutation, allowing robust expression of caErbb2 specifically in CMs in defined temporal windows. Induction of the transgene begins after withdrawal of the tetracycline analog doxycycline (DOX), which represses transgene expression (FIG. 10A).

The present inventors induced caErbB2 in CMs at neonate (~P1-P2), juvenile (~P8-P9) and adult (~5-weeks) stages (FIGS. 3A-C). Western blot analysis of control and caErbB2 heart lysates confirmed the present experimental settings (FIG. 10B; note that significant up-regulation of ErbB2 begins ~8-9 days after DOX withdrawal due to the slow clearance of DOX from tissues[45]). With all induction regimes, caErbb2 mice showed cardiomegaly (FIGS. 10C-E) with a marked increase in heart weight/tibia length ratio, and both thickening and elongation of the inter-ventricular septum and free walls (FIGS. 3D-F).

Functional analysis of caErbb2 hearts by echocardiography and by retrospectively gated cardiac MRI showed a significant increase in left ventricular (LV) anterior and posterior wall (LVAW and LVPW) thickness leading to decreased end-diastolic and end-systolic dimensions (LVEDD and LVESD) and dramatically reduced stroke volume compared with control mice, despite elevated ejection fraction and fractional shortening (FIGS. 3G-I; FIGS. 10F-H). These functional parameters are consistent with hypertrophic cardiomyopathy with chamber occlusion. caErbb2 induction shortly after birth (P1 or P7) led to reduced body weight and death, an expected outcome given the severely reduced cardiac output during postnatal growth. Less dramatic changes in body weight were observed in adult caErbb2 induction (~P35) and deaths were observed rarely over the time period tested (4 months), despite clear cardiomegaly at 8 weeks (FIGS. 3J-O).

CM size as well as markers of the hypertrophic response was increased in caErbb2 hearts (FIGS. 4A-D; FIG. 11A). These results are consistent with the marked hypertrophy previously observed in response to cardiac overexpression of wild-type Erbb2[46]. However immunofluorescence analysis revealed a striking increase in cell-cycle activity, mitosis and cytokinesis in caErbb2 CMs (FIGS. 4E-G). To directly visualize cell divisions, the present inventors employed time-lapse imaging of control and caErbb2 P7 CMs labelled with tetramethylrhodamine ethyl ester (TMRE), a fluorescent mitochondrial dye[47]. In control CMs the present inventors didn't observe any CM division or bi-nucleation events during the 12-hour time frame. In contrast, caErbb2-derived mono-nucleated CMs underwent karyokinesis plus cytokinesis (7.6%) or bi-nucleation (karyokinesis only, 0.7%) (FIG. 4H). Thus, caErbb2 preferentially induces complete cell division rather than bi-nucleation in mono-nucleated CMs (FIG. 4I). Strikingly, 3.9% of bi-nucleated caErbb2 CMs divided to form two mono-nucleated daughter cells (FIG. 4J). Accordingly, the ratio of mono- to bi-nucleated CMs was increased in caErbb2 compared to controls (FIG. 4K). In line with these data, calculation of CM number in vivo showed ~45% increase in adult caErbb2 mice compared to controls (FIG. 11B).

Proliferating CMs in zebrafish and mouse regenerative models undergo dedifferentiation characterized by partial disassembly of sarcomeres and loss of cell adhesion[11, 12]. Accordingly, the present inventors observed a disordered arrangement of CMs and increased inter-cellular spaces in caErbb2 hearts compared to controls, suggestive of disrupted CM adhesion (FIG. 5A; FIGS. 11C,D). Disassembly, reduction and even loss of sarcomeric structures were observed in caErbb2 hearts in vitro and in vivo (FIGS. 5B-D and FIGS. 11E,F). This was paralleled by an increase in the percentage of CMs expressing α-smooth muscle actin (αSMA) (FIG. 5E), reflective of an immature foetal state[48]. It has been recently shown that stem/progenitor markers RUNX1, cKIT and DAB2 identify dedifferentiated CMs[48]. Immunofluorescence staining revealed a strong induction of RUNX1 and DAB2 in caErbb2 CMs (FIGS. 5F,G) and cKIT expression levels were increased in lysate of caErbb2 hearts (FIG. 11G). Taken together, the increase CM cell division, disassembly and reduction of sarcomeres, replacement with immature components, and re-expression of progenitor markers strongly indicate that caErbB2 signalling induces robust CM dedifferentiation to an immature and proliferative state.

Example 3

Figure 12A:
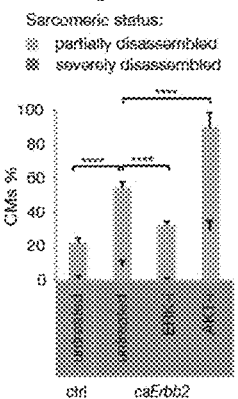

ERK, AKT and GSK3β/β-Catenin Differentially Mediate ErbB2-Induced Cardiomyocyte Proliferation, Dedifferentiation, and Hypertrophy NRG1/ErbB4/ErbB2 activity has been linked to a number of downstream signalling pathways including ERK and AKT[22, 28, 33]. As expected, ERK and AKT were activated in caErbb2 hearts (FIG. 6A). The present inventors asked whether the distinct cellular responses to caErbB2 signalling were differentially affected by known inhibitors of these signalling pathways. Cell cycle activity (Ki67), dedifferentiation (sarcomeric disassembly and RUNX1 expression) and hypertrophy were analysed with and without inhibitors in CMs explanted from caErbb2 and control mice at P7, a time point at which proliferation and RUNX1 expression in control CMs is negligible (see FIGS. 4A-K and 5A-G). ERK inhibition completely suppressed caErbB2-induced CM proliferation and dedifferentiation, and reduced the hypertrophic response (FIGS. 6B-D; FIG. 12A). In contrast, AKT inhibition had a moderate effect on CM proliferation, reduced hypertrophic response, and promoted massive dedifferentiation of caErbb2 CMs (FIGS. 6B-D; FIG. 12A). Thus, caErbB2-induced CM dedifferentiation and proliferation are ERK-dependent, while the hypertrophic response is mediated by both ERK and AKT. These pathways, however, play opposing roles in CM dedifferentiation.

Figure 12B:
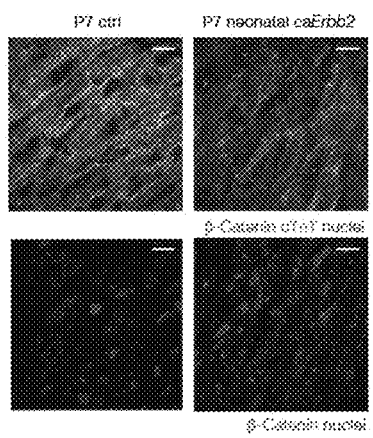
Figure 12C:
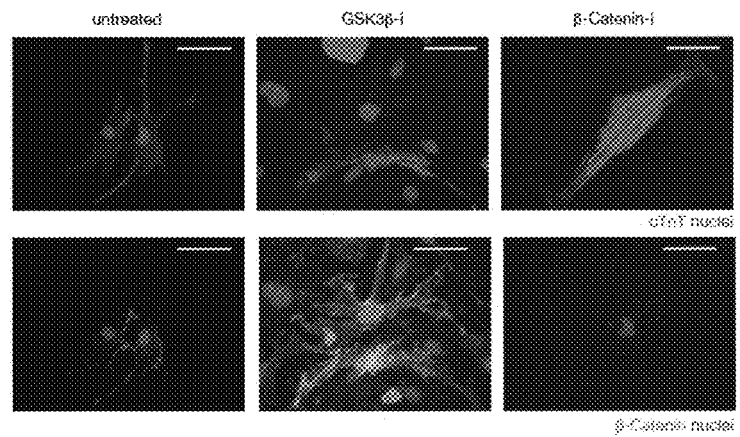
Figure 12D:
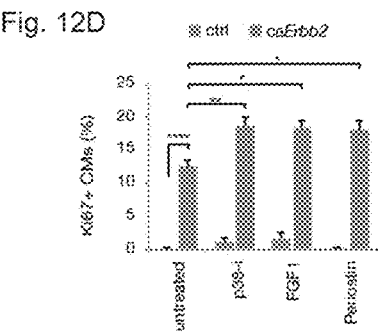
Figure 12E:
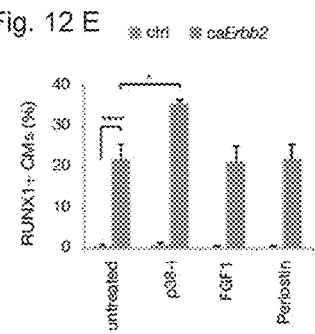
Figure 12F:
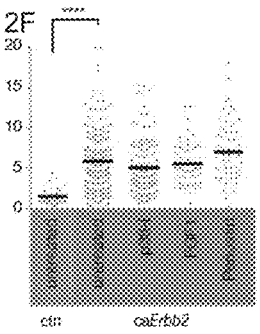

Inhibition of GSK3β has been suggested as a strategy to promote CM proliferation[49, 50]. It has been shown that ErbB2 activation promotes intracellular accumulation of β-Catenin[51] via repression of GSK3β activity[52-54]. Indeed, increased β-Catenin protein levels and its cytoplasmic accumulation were detected in caErbb2 heart lysates and CMs (FIG. 6E; FIG. 12B). β-Catenin inhibition reduced ErbB2-induced RUNX1 expression in CMs without significantly affecting cell cycle re-entry or hypertrophy (FIGS. 6F-H). In contrast, GSK3β inhibition in caErbb2 CMs further increased β-Catenin accumulation (FIG. 12C) and RUNX1 expression, and promoted β-Catenin independent increase in cell cycle activity (FIGS. 6F-H). Finally, the present inventors analysed the additive/synergistic effects of caErbB2 together with inhibition of p38 or administration of Periostin or FGF1, which were demonstrated to induce adult CM proliferation[55-57]. All three treatments enhanced caErbB2-induced CM proliferation (FIG. 12D). Further, p38 inhibition, in contrast to FGF1 and Periostin, increased RUNX1 expression in caErbb2 CMs (FIG. 12E). No obvious effects were observed on hypertrophic CM growth (FIG. 12F). Collectively, these results reveal a signalling network downstream of ErbB2 dominated by ERK, AKT and GSK3β/β-catenin, which can crosstalk with other signalling molecules (e.g., p38) or factors (e.g. Periostin and FGF1) (FIG. 6I). The present assay of signalling inhibitors uncovered surprising uncoupling between CM hypertrophy, dedifferentiation and proliferation, which could be translated to therapeutic purposes.

Example 4

Transient ErbB2 Activation Extends the Cardiac Regenerative Window

The present data thus far suggest that after P7, at which most CMs withdraw from the cell cycle, caErbb2 induction promotes robust CM dedifferentiation and proliferation, albeit leading to cardiomegaly and hypertrophic cardiomyopathy, and even death. The present inventors asked whether induction of cardiac dedifferentiation and proliferation by transient activation of ErbB2 signalling in juvenile and adult stages, for ~10 and ~21 days, respectively, would allow cardiac regeneration following myocardial ischemic injury induced by permanent ligation of the left anterior descending coronary artery (LAD) (FIGS. 7A,B).

Transient caErbB2 induced CM cell cycle activity and cytokinesis in the infarct border zone as well as in remote regions of both juvenile and adult hearts (FIGS. 7C-F). Strikingly, in both injury models, transient caErbb2 induction resulted in significantly improved recovery of cardiac performance after MI (FIGS. 7G,H). Improvement in heart function was evident after caErbb2 expression was shut down by DOX administration, especially in the adult setting (FIG. 7H). Analysis of sarcomeric structures, one month after the MI (~P70) and caErbb2 induction, revealed a robust dedifferentiated cardiac muscle. A month after termination of caErbB2 expression (~P98), tissue morphology and sarcomeric organization were restored, reflecting CM re-differentiation process (FIG. 7I; FIG. 13A). The present inventors also observed increased angiogenesis during caErbB2-induced adult cardiac regeneration process (FIG. 13B). Transient caErbb2 hearts had reduced scar compared to control mice (FIG. 7J,K). Collectively, the present findings indicate that transient re-activation of ErbB2 signalling facilitates heart regeneration after MI as a result of increased CM dedifferentiation and proliferation accompanied by neovascularization and followed by re-differentiation, tissue replacement with reduced scar formation and restoration of LV chamber function (FIG. 8).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Bergmann, O. et al. Evidence for cardiomyocyte renewal in humans. Science 324, 98-102 (2009).
2. Senyo, S. E. et al. Mammalian heart renewal by pre-existing cardiomyocytes. Nature 493, 433-436 (2013).
3. Laflamme, M. A. & Murry, C. E. Regenerating the heart. Nat Biotechnol 23, 845-856 (2005).
4. Poss, K. D. Getting to the heart of regeneration in zebrafish. Semin Cell Dev Biol 18, 36-45 (2007).
5. Ausoni, S. & Sartore, S. From fish to amphibians to mammals: in search of novel strategies to optimize cardiac regeneration. J Cell Biol 184, 357-364 (2009).
6. Mercola, M., Ruiz-Lozano, P. & Schneider, M. D. Cardiac muscle regeneration: lessons from development. Genes Dev 25, 299-309 (2011).
7. Garbern, J. C. & Lee, R. T. Cardiac stem cell therapy and the promise of heart regeneration. Cell stem cell 12, 689-698 (2013).
8. Li, F., Wang, X., Capasso, J. M. & Gerdes, A. M. Rapid transition of cardiac myocytes from hyperplasia to hypertrophy during postnatal development. Journal of molecular and cellular cardiology 28, 1737-1746 (1996).
9. Soonpaa, M. H. & Field, L. J. Survey of studies examining mammalian cardiomyocyte DNA synthesis. Circ Res 83, 15-26 (1998).
10. Naqvi, N. et al. A Proliferative Burst during Preadolescence Establishes the Final Cardiomyocyte Number. Cell 157, 795-807 (2014).

11. Jopling, C. et al. Zebrafish heart regeneration occurs by cardiomyocyte dedifferentiation and proliferation. Nature 464, 606-609 (2010).
12. Porrello, E. R. et al. Transient regenerative potential of the neonatal mouse heart. Science 331, 1078-1080 (2011).
13. van Berlo, J. H. & Molkentin, J. D. An emerging consensus on cardiac regeneration. Nature medicine 20, 1386-1393 (2014).
14. Xin, M., Olson, E. N. & Bassel-Duby, R. Mending broken hearts: cardiac development as a basis for adult heart regeneration and repair. Nature reviews. Molecular cell biology 14, 529-541 (2013).
15. Gassmann, M. et al. Aberrant neural and cardiac development in mice lacking the ErbB4 neuregulin receptor. Nature 378, 390-394 (1995).
16. Lee, K. F. et al. Requirement for neuregulin receptor erbB2 in neural and cardiac development. Nature 378, 394-398 (1995).
17. Meyer, D. & Birchmeier, C. Multiple essential functions of neuregulin in development. Nature 378, 386-390 (1995).
18. Lai, D. et al. Neuregulin 1 sustains the gene regulatory network in both trabecular and nontrabecular myocardium. Circ Res 107, 715-727 (2010).
19. Liu, J. et al. A dual role for ErbB2 signaling in cardiac trabeculation. Development 137, 3867-3875 (2010).
20. Staudt, D. W. et al. High-resolution imaging of cardiomyocyte behavior reveals two distinct steps in ventricular trabeculation. Development 141, 585-593 (2014).
21. Zhao, Y. Y. et al. Neuregulins promote survival and growth of cardiac myocytes. Persistence of ErbB2 and ErbB4 expression in neonatal and adult ventricular myocytes. The Journal of biological chemistry 273, 10261-10269 (1998).
22. Odiete, O., Hill, M. F. & Sawyer, D. B. Neuregulin in cardiovascular development and disease. Circ Res 111, 1376-1385 (2012).
23. Wadugu, B. & Kuhn, B. The role of neuregulin/ErbB2/ErbB4 signaling in the heart with special focus on effects on cardiomyocyte proliferation. American journal of physiology. Heart and circulatory physiology 302, H2139-2147 (2012).
24. Fukazawa, R. et al. Neuregulin-1 protects ventricular myocytes from anthracycline-induced apoptosis via erbB4-dependent activation of PI3-kinase/Akt. Journal of molecular and cellular cardiology 35, 1473-1479 (2003).
25. Liu, X. et al. Neuregulin-1/erbB-activation improves cardiac function and survival in models of ischemic, dilated, and viral cardiomyopathy. J Am Coll Cardiol 48, 1438-1447 (2006).
26. Bersell, K., Arab, S., Haring, B. & Kuhn, B. Neuregulin1/ErbB4 signaling induces cardiomyocyte proliferation and repair of heart injury. Cell 138, 257-270 (2009).
27. Xu, Y., Li, X., Liu, X. & Thou, M. Neuregulin-1/ErbB signaling and chronic heart failure. Adv Pharmacol 59, 31-51 (2010).
28. Pentassuglia, L. & Sawyer, D. B. The role of Neuregulin-1beta/ErbB signaling in the heart. Exp Cell Res 315, 627-637 (2009).
29. Gao, R. et al. A Phase II, randomized, double-blind, multicenter, based on standard therapy, placebo-controlled study of the efficacy and safety of recombinant human neuregulin-1 in patients with chronic heart failure. J Am Coll Cardiol 55, 1907-1914 (2010).
30. Jabbour, A. et al. Parenteral administration of recombinant human neuregulin-1 to patients with stable chronic heart failure produces favourable acute and chronic haemodynamic responses. Eur J Heart Fail 13, 83-92 (2011).
31. Sawyer, D. B. & Caggiano, A. Neuregulin-1beta for the treatment of systolic heart failure. Journal of molecular and cellular cardiology 51, 501-505 (2011).
32. Reuter, S., Soonpaa, M. H., Firulli, A. B., Chang, A. N. & Field, L. J. Recombinant neuregulin 1 does not activate cardiomyocyte DNA synthesis in normal or infarcted adult mice. PloS one 9, e115871 (2014).
33. Yarden, Y. & Sliwkowski, M. X. Untangling the ErbB signalling network. Nature reviews. Molecular cell biology 2, 127-137 (2001).
34. Citri, A. & Yarden, Y. EGF-ErbB signalling: towards the systems level. Nature reviews. Molecular cell biology 7, 505-516 (2006).
35. Pradeep, C. R. et al. Modeling invasive breast cancer: growth factors propel progression of HER2-positive premalignant lesions. Oncogene 31, 3569-3583 (2012).
36. Tzahar, E. et al. A hierarchical network of interreceptor interactions determines signal transduction by Neu differentiation factor/neuregulin and epidermal growth factor. Mol Cell Biol 16, 5276-5287 (1996).
37. Graus-Porta, D., Beerli, R. R., Daly, J. M. & Hynes, N. E. ErbB-2, the preferred heterodimerization partner of all ErbB receptors, is a mediator of lateral signaling. EMBO J 16, 1647-1655 (1997).
38. Olayioye, M. A. et al. ErbB-1 and ErbB-2 acquire distinct signaling properties dependent upon their dimerization partner. Mol Cell Biol 18, 5042-5051 (1998).
39. Garrett, T. P. et al. The crystal structure of a truncated ErbB2 ectodomain reveals an active conformation, poised to interact with other ErbB receptors. Mol Cell 11, 495-505 (2003).
40. Agah, R. et al. Gene recombination in postmitotic cells. Targeted expression of Cre recombinase provokes cardiac-restricted, site-specific rearrangement in adult ventricular muscle in vivo. J Clin Invest 100, 169-179 (1997).
41. Ozcelik, C. et al. Conditional mutation of the ErbB2 (HER2) receptor in cardiomyocytes leads to dilated cardiomyopathy. Proceedings of the National Academy of Sciences of the United States of America 99, 8880-8885 (2002).
42. Britsch, S. et al. The ErbB2 and ErbB3 receptors and their ligand, neuregulin-1, are essential for development of the sympathetic nervous system. Genes Dev 12, 1825-1836 (1998).
43. Bargmann, C. I., Hung, M. C. & Weinberg, R. A. Multiple independent activations of the neu oncogene by a point mutation altering the transmembrane domain of p185. Cell 45, 649-657 (1986).
44. Penuel, E., Akita, R. W. & Sliwkowski, M. X. Identification of a region within the ErbB2/HER2 intracellular domain that is necessary for ligand-independent association. The Journal of biological chemistry 277, 28468-28473 (2002).
45. Ghashghaei, H. T. et al. Reinduction of ErbB2 in astrocytes promotes radial glial progenitor identity in adult cerebral cortex. Genes Dev 21, 3258-3271 (2007).
46. Sysa-Shah, P. et al. Cardiac-specific over-expression of epidermal growth factor receptor 2 (ErbB2) induces pro-survival pathways and hypertrophic cardiomyopathy in mice. PloS one 7, e42805 (2012).
47. Hattori, F. et al. Nongenetic method for purifying stem cell-derived cardiomyocytes. Nature methods 7, 61-66 (2010).

48. Kubin, T. et al. Oncostatin M is a major mediator of cardiomyocyte dedifferentiation and remodeling. Cell stem cell 9, 420-432 (2011).
49. Tseng, A. S., Engel, F. B. & Keating, M. T. The GSK-3 inhibitor BIO promotes proliferation in mammalian cardiomyocytes. Chemistry & biology 13, 957-963 (2006).
50. Uosaki, H. et al. Identification of chemicals inducing cardiomyocyte proliferation in developmental stage-specific manner with pluripotent stem cells. Circulation. Cardiovascular genetics 6, 624-633 (2013).
51. Schade, B. et al. beta-Catenin signaling is a critical event in ErbB2-mediated mammary tumor progression. Cancer Res 73, 4474-4487 (2013).
52. Reya, T. & Clevers, H. Wnt signalling in stem cells and cancer. Nature 434, 843-850 (2005).
53. Plotnikov, A. et al. Oncogene-mediated inhibition of glycogen synthase kinase 3 beta impairs degradation of prolactin receptor. Cancer Res 68, 1354-1361 (2008).
54. Zaoui, K., Benseddik, K., Daou, P., Salaun, D. & Badache, A. ErbB2 receptor controls microtubule capture by recruiting ACF7 to the plasma membrane of migrating cells. Proceedings of the National Academy of Sciences of the United States of America 107, 18517-18522 (2010).
55. Engel, F. B. et al. p38 MAP kinase inhibition enables proliferation of adult mammalian cardiomyocytes. Genes Dev 19, 1175-1187 (2005).
56. Engel, F. B., Hsieh, P. C., Lee, R. T. & Keating, M. T. FGF1/p38 MAP kinase inhibitor therapy induces cardiomyocyte mitosis, reduces scarring, and rescues function after myocardial infarction. Proceedings of the National Academy of Sciences of the United States of America 103, 15546-15551 (2006).
57. Kuhn, B. et al. Periostin induces proliferation of differentiated cardiomyocytes and promotes cardiac repair. Nature medicine 13, 962-969 (2007).
58. Whelan, R. S., Kaplinskiy, V. & Kitsis, R. N. Cell death in the pathogenesis of heart disease: mechanisms and significance. Annu Rev Physiol 72, 19-44 (2010).
59. Krijnen, P. A. et al. Apoptosis in myocardial ischaemia and infarction. Journal of clinical pathology 55, 801-811 (2002).
60. Mahmoud, A. I. et al. Meis1 regulates postnatal cardiomyocyte cell cycle arrest. Nature 497, 249-253 (2013).
61. Puente, B. N. et al. The oxygen-rich postnatal environment induces cardiomyocyte cell-cycle arrest through DNA damage response. Cell 157, 565-579 (2014).
62. Aurora, A. B. et al. Macrophages are required for neonatal heart regeneration. J Clin Invest 124, 1382-1392 (2014).
63. Heallen, T. et al. Hippo signaling impedes adult heart regeneration. Development 140, 4683-4690 (2013).

What is claimed is:

1. A method of regenerating a cardiac tissue in a subject in need thereof, the method comprising administering to the subject a therapeutic effective amount of an agent which upregulates activity or expression of ErbB-2, wherein said agent is a nucleic acid molecule encoding constitutively active ErbB-2, wherein said agent is administered to elicit an upregulation in said activity or expression of said ErbB-2 in a transient manner until appearance of hypertrophic or hyperplastic effects.

2. The method of claim 1, wherein said nucleic acid molecule is modRNA.

3. The method of claim 1, wherein said subject has or at risk of a heart failure selected from the group consisting of a congestive heart failure, myocardial infarction, tachyarrhythmia, familial hypertrophic cardiomyopathy, ischemic heart disease, idiopathic dilated cardiomyopathy and myocarditis.

4. The method of claim 1, wherein said heart failure is caused by a factor selected from the group consisting of an ischemic factor, a congenital factor, a rheumatic factor, a viral factor, a toxic factor and an idiopathic factor.

5. A method of regenerating a cardiac tissue in a subject in need thereof, the method comprising administering to the subject a therapeutic effective amount of neuregulin and an agent which upregulates activity or expression of ErbB-2, wherein said agent is a nucleic acid molecule encoding ErbB-2, wherein said agent is administered to elicit an upregulation in said activity or expression of said ErbB-2 in a transient manner until appearance of hypertrophic or hyperplastic effects, thereby regenerating the cardiac tissue.

6. The method of claim 5, wherein said neuregulin is selected from the group consisting of, neuregulin-1, neuregulin-2, neuregulin-3 and neuregulin-4.

7. The method of claim 5, wherein said nucleic acid molecule is modRNA.

8. The method of claim 5, wherein said subject has or at risk of a heart failure selected from the group consisting of a congestive heart failure, myocardial infarction, tachyarrhythmia, familial hypertrophic cardiomyopathy, ischemic heart disease, idiopathic dilated cardiomyopathy and myocarditis.

9. The method of claim 5, wherein said heart failure is caused by a factor selected from the group consisting of an ischemic factor, a congenital factor, a rheumatic factor, a viral factor, a toxic factor and an idiopathic factor.

10. A method of identifying an agent useful in cardiac regeneration, the method comprising:
(a) contacting the agent with post natal cardiomyocytes that correspond to murine P7;
(b) measuring an activity or expression of said ErbB-2 in said cardiomyocytes, wherein an upregulation in said ErbB-2 activity or expression following said contacting is indicative that the agent is useful cardiac tissue regeneration.

* * * * *